US012723279B2

(12) United States Patent
Cressina et al.

(10) Patent No.: US 12,723,279 B2
(45) Date of Patent: Sep. 1, 2026

(54) LONG STOKES SHIFT CHROMENOQUINOLINE DYES AND USES IN SEQUENCING APPLICATIONS

(71) Applicant: Illumina Cambridge Limited, Cambridge (GB)

(72) Inventors: Elena Cressina, Cambridge (GB); Antoine Francais, Cambridge (GB); Xiaohai Liu, Cambridge (GB)

(73) Assignee: ILLUMINA CAMBRIDGE LIMITED, Cambridge (GB)

(*) Notice: Subject to any disclaimer, the term of this patent is extended or adjusted under 35 U.S.C. 154(b) by 1296 days.

(21) Appl. No.: 17/550,271

(22) Filed: Dec. 14, 2021

(65) Prior Publication Data

US 2022/0195517 A1 Jun. 23, 2022

Related U.S. Application Data

(60) Provisional application No. 63/127,061, filed on Dec. 17, 2020.

(51) Int. Cl.

| | |
|---|---|
| ***C07D 491/147*** | (2006.01) |
| ***C07D 491/22*** | (2006.01) |
| ***C07H 19/14*** | (2006.01) |
| ***C12Q 1/6853*** | (2018.01) |
| ***C12Q 1/6874*** | (2018.01) |
| ***G01N 21/64*** | (2006.01) |

(52) U.S. Cl.

CPC ....... *C12Q 1/6874* (2013.01); *C07D 491/147* (2013.01); *C07D 491/22* (2013.01); *C07H 19/14* (2013.01); *C12Q 1/6853* (2013.01); *G01N 21/6428* (2013.01); *G01N 2021/6439* (2013.01)

(58) Field of Classification Search

None

See application file for complete search history.

(56) References Cited

U.S. PATENT DOCUMENTS 5,171,534 A 12/1992 Smith et al.
5,302,509 A 4/1994 Cheeseman
5,429,807 A 7/1995 Matson et al.
5,436,130 A 7/1995 Mathies et al.
5,436,327 A 7/1995 Southern et al.
5,561,071 A 10/1996 Hollenberg et al.
5,583,211 A 12/1996 Coassin et al.
5,658,734 A 8/1997 Brock et al.
5,837,858 A 11/1998 Brennan
5,874,219 A 2/1999 Rava et al.
5,919,523 A 7/1999 Sundberg et al.
6,136,269 A 10/2000 Winkler et al.
6,172,218 B1 1/2001 Brenner
6,287,768 B1 9/2001 Chenchik et al.
6,287,776 B1 9/2001 Hefti
6,288,220 B1 9/2001 Kambara et al.
6,291,193 B1 9/2001 Khodadoust
6,297,006 B1 10/2001 Drmanac et al.
6,346,413 B1 2/2002 Fodor et al.
6,355,431 B1 3/2002 Chee et al.
6,416,949 B1 7/2002 Dower et al.
6,465,178 B2 10/2002 Chappa et al.
6,482,591 B2 11/2002 Lockhart et al.
6,514,751 B2 2/2003 Johann et al.
6,524,793 B1 2/2003 Chandler et al.
6,610,482 B1 8/2003 Fodor et al.
8,906,320 B1 12/2014 Eltoukhy et al.
9,453,258 B2 9/2016 Kain et al.
9,990,381 B2 6/2018 Eltoukhy et al.
10,214,768 B2 2/2019 Romanov
10,287,629 B2 5/2019 Kain et al.
10,533,211 B2 1/2020 Romanov
10,738,072 B1 8/2020 Graham
10,900,077 B2 1/2021 Kain et al.
10,907,196 B2 2/2021 Romanov
2002/0102578 A1 8/2002 Dickinson
2002/0192697 A1 12/2002 Izmailov
2004/0260093 A1 12/2004 Czerney et al.
2008/0032414 A1 2/2008 Zhuang et al.
2012/0020537 A1 1/2012 Garcia et al.
2013/0079232 A1 3/2013 Kain
2013/0288902 A1 10/2013 Utiramerur et al.
2013/0316914 A1 11/2013 Gordon et al.
2014/0079923 A1 3/2014 George
2014/0255920 A1 9/2014 Romanov et al.
2014/0255943 A1 9/2014 Hoyal-Wrightson et al.
2015/0031560 A1 1/2015 Fabani et al.
2015/0111763 A1 4/2015 Eshoo (Continued)

FOREIGN PATENT DOCUMENTS

CN 1788193 6/2006
CN 201313902 Y 9/2009

(Continued)

OTHER PUBLICATIONS

International search report and written opinion dated May 11, 2022 in International Application No. PCT/EP2021/086344.
Geng et al., An aqueous methylated chromenoquinoline-based fluorescent probe for instantaneous sensing of thiophenol with a red emission and a large Stokes shift, Sensors & Actuators: B. Chemical, 2018, 273:1670-1675.
Liu et al., Methylated chromenoquinoline dyes: synthesis, optical properties, and application for mitochondrial labeling, Chemical Communications,2018, 54, 1509-1512; DOI: 10.1039/C7CC08154E.
Margulies, Sep. 15, 2005, Genome sequencing in microfabricated high-density picolitre reactors, Nature, 437:376-380.
Schendure et al., Sep. 9, 2005, Accurate multiplex polony sequencing of an evolved bacterial genome, Science, 309(5741):1728-1732.
Scheit, K. H. (1980). Nucleotide analogs: Synthesis and biological function. New York: John Wiley & Sons, TOC, 5 pages.

(Continued)

*Primary Examiner* — Traviss C McIntosh, III

(74) *Attorney, Agent, or Firm* — KNOBBE, MARTENS, OLSON & BEAR, LLP

(57) ABSTRACT

The present application relates to long Stokes shift chromenoquinoline dyes and their uses as fluorescent labels. For example, these dyes may be used to label nucleotides for nucleic acid sequencing applications.

42 Claims, 7 Drawing Sheets

(56) References Cited

U.S. PATENT DOCUMENTS

| | | | |
|---|---|---|---|
| 2015/0169824 | A1 | 6/2015 | Kermani et al. |
| 2015/0184238 | A1 | 7/2015 | Eshoo |
| 2016/0040225 | A1 | 2/2016 | Wu et al. |
| 2017/0022559 | A1 | 1/2017 | Kain et al. |
| 2018/0094140 | A1 | 4/2018 | Romanov |
| 2018/0201981 | A1 | 7/2018 | Romanov |
| 2020/0131484 | A1 | 4/2020 | Golynskiy et al. |
| 2020/0181587 | A1 | 6/2020 | Klausing et al. |
| 2020/0216891 | A1 | 7/2020 | Francais et al. |
| 2020/0277529 | A1 | 9/2020 | Romanov et al. |
| 2020/0277670 | A1 | 9/2020 | Romanov et al. |
| 2021/0403500 | A1 | 12/2021 | Francais et al. |
| 2022/0033900 | A1 | 2/2022 | Romanov et al. |
| 2022/0195196 | A1 | 6/2022 | Cressina et al. |
| 2022/0195516 | A1 | 6/2022 | Cressina et al. |
| 2022/0195517 | A1 | 6/2022 | Cressina et al. |

FOREIGN PATENT DOCUMENTS

| | | | |
|---|---|---|---|
| CN | 105504860 | | 4/2016 |
| CN | 205616889 U | | 10/2016 |
| CN | 105504860 B | * | 4/2019 |
| EP | 0 742 287 | | 11/1996 |
| EP | 0 799 897 | | 10/1997 |
| EP | 2 551 665 | | 3/2015 |
| EP | 3 702 474 | | 9/2020 |
| JP | 2004-177290 | | 6/2004 |
| JP | 2009-232871 | | 10/2009 |
| JP | 2011-027706 | | 2/2011 |
| JP | 2012-132923 | | 7/2012 |
| JP | 2015-514218 | | 6/2015 |
| WO | WO 93/17126 | | 9/1993 |
| WO | WO 95/11995 | | 5/1995 |
| WO | WO 95/35505 | | 12/1995 |
| WO | WO 98/44151 | | 10/1998 |
| WO | WO 00/06770 | | 2/2000 |
| WO | WO 00/18957 | | 4/2000 |
| WO | WO 00/31148 | | 6/2000 |
| WO | WO 00/63437 | | 10/2000 |
| WO | WO 01/01143 | | 1/2001 |
| WO | WO 01/57248 | | 8/2001 |
| WO | WO 02/012566 | | 2/2002 |
| WO | WO 02/029003 | | 4/2002 |
| WO | WO 02/095070 | | 11/2002 |
| WO | WO 03/014392 | | 2/2003 |
| WO | WO 03/021212 | | 3/2003 |
| WO | WO 04/018493 | | 3/2004 |
| WO | WO 04/018497 | | 3/2004 |
| WO | WO 04/063731 | | 7/2004 |
| WO | WO 05/024010 | | 3/2005 |
| WO | WO 05/047301 | | 5/2005 |
| WO | WO 05/065814 | | 7/2005 |
| WO | WO 06/120433 | | 11/2006 |
| WO | WO 07/020457 | | 2/2007 |
| WO | WO 12/096703 | | 7/2012 |
| WO | WO 13/041117 | | 3/2013 |
| WO | WO 14/135221 | | 9/2014 |
| WO | WO 2014/139596 | | 9/2014 |
| WO | WO 15/089092 | | 6/2015 |
| WO | WO 15/170102 | | 11/2015 |
| WO | WO 16/189287 | | 12/2016 |
| WO | WO 17/051201 | | 3/2017 |
| WO | WO 18/114710 | | 6/2018 |
| WO | WO 2018/129214 | | 7/2018 |
| WO | WO 18/165099 | | 9/2018 |
| WO | WO 2020/097607 | | 5/2020 |
| WO | WO 00/53812 | | 9/2020 |

OTHER PUBLICATIONS

Uhlman et al., Jun. 1990, Antisense oligonucleotides: a new therapeutic principle, Chemical Reviews, 90(4):543-584.

Illumina Inc., Dec. 31, 2018, Illumina CMOS chip and one-channel SBS chemistry, https://www.illumina.com/contenUdam/illumina-marketing/documents/products/techspolights/cmos-tech-note-770-2013-054.pdf, 4 pp. (Year: 2018).

Wu et al., "Microarray-based Ms-SNuPE: Near-quantitative analysis for a high-throughput DNA methylation" Biosensors and Bioelectronics 23; 1333-1339 (2008).

Anonymous: "ABI PRISM 310 Genetic Analyzer", Applied Biosystems Jul. 31, 2004 (Jul. 31, 2004), XP055483711 Retrieved from the Internet: URL:https://assets.thermofisher.com/TFS-Assets/LSG/Specification-Sheets/cms 040736.pdf [retrieved on Jun. 13, 2018].

Anonymous: 11 DYEnamic ET Terminator Cycle Sequencing Kit, GE Healthcare Dec. 31, 2006 (Dec. 31, 2006), XP055483701, retrieved from the Internet: URL:https://www.gelifesciences.co.jp/tech_support/manual/pdf/us81050pl rev c.pdf [retrieved on Jun. 13, 2018]—p. 8, 9, 11, 19-29.

Drmanac et al., 2010, Human genome sequencing using unchained base reads on self-assembling DNA nanoarrays, Science 327(5961): 78-81.

Illumina Inc., Dec. 31, 2018, Illumina CMOS chip and one-channel SBS chemistry, https://www.illumina.com/content/dam/illumina-marketing/documents/products/techspolights/cmos-tech-note-770-2013-054.pdf, 4 pp.

Illumina, Oct. 2014, Sequencing Analysis Viewer Software, User Guide, https://support.illumina.com/downloads/sequencing-analysis-viewer-software.html, 33 pp.

Lieberwirth, U. et al.: "Multiplex Dye DNA Sequencing in Capillary Gel Electrophoresis by Diode Laser Laser-Based Time-Resolved Fluorescence Detection", Analytical Chemistry, American Chemical Society, US, vol. 70, No. 22, Nov. 15, 1998 (Nov. 15, 1998), pp. 4771-4779.

Schill et al., 2013, 4-trifluoromethyl-substituted coumarins with large stokes shifts: synthesis, bioconjugates, and their use in super-resolution fluorescence microscopy, Chem. Eur. J., 19:16556-16565.

* cited by examiner ffA-sPA-LN3-I-1 ffA-sPA-LN3-I-2 ffA-sPA-LN3-I-3 ffA-sPA-LN3-I-4 ffA-sPA-LN3-I-5

LONG STOKES SHIFT CHROMENOQUINOLINE DYES AND USES IN SEQUENCING APPLICATIONS

INCORPORATION BY REFERENCE TO ANY PRIORITY APPLICATION

The present application claims the benefit of priority to U.S. Ser. No. 63/127,061, filed Dec. 17, 2020, which is incorporated by reference in its entirety.

FIELD

The present disclosure relates to chromenoquinoline dyes and their uses as fluorescent labels. In particular, the compounds may be used as nucleotide labels for nucleic acid sequencing applications.

BACKGROUND

Non-radioactive detection of nucleic acids bearing fluorescent labels is an important technology in molecular biology. Many procedures employed in recombinant DNA technology previously relied on the use of nucleotides or polynucleotides radioactively labeled with, for example $^{32}P$. Radioactive compounds permit sensitive detection of nucleic acids and other molecules of interest. However, there are serious limitations in the use of radioactive isotopes such as their expense, limited shelf life, insufficient sensitivity, and, more importantly, safety considerations. Eliminating the need for radioactive labels reduces both the safety risks and the environmental impact and costs associated with, for example, reagent disposal. Methods amenable to non-radioactive fluorescent detection include by way of non-limiting examples, automated DNA sequencing, hybridization methods, real-time detection of polymerase-chain-reaction products, and immunoassays.

For many applications, it is desirable to employ multiple spectrally-distinguishable fluorescent labels to achieve independent detection of a plurality of spatially-overlapping analytes. In such multiplex methods, the number of reaction vessels may be reduced, simplifying experimental protocols and facilitating the production of application-specific reagent kits. In multi-color automated DNA sequencing systems for example, multiplex fluorescent detection allows for the analysis of multiple nucleotide bases in a single electrophoresis lane, thereby increasing throughput over single-color methods, and reducing uncertainties associated with inter-lane electrophoretic mobility variations.

However, multiplex fluorescent detection can be problematic and there are a number of important factors that constrain selection of appropriate fluorescent labels. First, it may be difficult to find dye compounds with substantially-resolved absorption and emission spectra in a given application. In addition, when several fluorescent dyes are used together, generating fluorescence signals in distinguishable spectral regions by simultaneous excitation may be complicated because absorption bands of the dyes are usually widely separated, so it is difficult to achieve comparable fluorescence excitation efficiencies even for two dyes. Many excitation methods use high power light sources like lasers and therefore the dye must have sufficient photo-stability to withstand such excitation. A final consideration of particular importance to molecular biology methods is the extent to which the fluorescent dyes must be compatible with reagent chemistries such as, for example, DNA synthesis solvents and reagents, buffers, polymerase enzymes, and ligase enzymes.

As sequencing technology advances, a need has developed for further fluorescent dye compounds, their nucleic acid conjugates, and multiple dye sets that satisfy all the above constraints and that are amenable particularly to high throughput molecular methods such as solid phase sequencing and the like.

Fluorescent dye molecules with improved fluorescence properties such as suitable fluorescence intensity, shape, and wavelength maximum of fluorescence band can improve the speed and accuracy of nucleic acid sequencing. Strong fluorescence signals are especially important when measurements are made in water-based biological buffers and at higher temperatures as the fluorescence intensities of most organic dyes are significantly lower under such conditions. Moreover, the nature of the base to which a dye is attached also affects the fluorescence maximum, fluorescence intensity, and others spectral dye properties. The sequence-specific interactions between the nucleobases and the fluorescent dyes can be tailored by specific design of the fluorescent dyes. Optimization of the structure of the fluorescent dyes can improve the efficiency of nucleotide incorporation, reduce the level of sequencing errors, and decrease the usage of reagents in, and therefore the costs of, nucleic acid sequencing.

Some optical and technical developments have already led to greatly improved image quality but were ultimately limited by poor optical resolution. Generally, optical resolution of light microscopy is limited to objects spaced at approximately half of the wavelength of the light used. In practical terms, then, only objects that are laying quite far apart (at least 200 to 350 nm) could be resolved by light microscopy. One way to improve image resolution and increase the number of resolvable objects per unit of surface area is to use excitation light of a shorter wavelength. For example, if light wavelength is shortened by $\Delta\lambda$~100 nm with the same optics, resolution will be better (about $\Delta$50 nm/(about 15%)), less-distorted images will be recorded, and the density of objects on the recognizable area will be increased about 35%.

Certain nucleic acid sequencing methods employ laser light to excite and detect dye-labeled nucleotides. These instruments use longer wavelength light, such as red lasers, along with appropriate dyes that are excitable at 660 nm. To detect more densely packed nucleic acid sequencing clusters while maintaining useful resolution, a shorter wavelength blue light source (450-460 nm) may be used. In this case, optical resolution will be limited not by the emission wavelength of the longer wavelength red fluorescent dyes but rather by the emission of dyes excitable by the next longest wavelength light source, for example, by "green laser" at 532 nm. Thus, there is a need for blue dye labels for use in fluorescence detection in sequencing applications.

Chromenoquinoline dyes have been reported in literature for use as fluorescent probes or mitochondrial labeling. See Geng et al., Sensors & Actuators: B. Chemical 273 (2018) 1670-1675 and Liu et al., Chemical Communications 2018, 54(12): 1509-1512. Nevertheless, most of these chromenoquinoline dyes have red emission and their stability at the aqueous condition for nucleic acid sequencing remains unknown. As such, designing chromenoquinoline dyes with tailor-made adsorption wavelength and fluorescent Stokes shifts with good stability remain the key challengers in the dye development.

SUMMARY

Described herein are chromenoquinoline dyes with long Stokes shift and improved fluorescent intensity and chemical stability suitable for nucleotide labeling and sequencing applications. These chromenoquinoline dyes have strong fluorescence under both blue and green light excitation (for example, these chromenoquinoline dyes may have an absorption wavelength of from about 450 nm to about 530 nm, from about 460 nm to about 520 nm, from about 475 nm to about 510 nm, or from about 490 nm to about 500 nm). Furthermore, these chromenoquinoline dyes have greater stability in high pH buffer compared to the commercially available dyes used for sequencing by synthesis.

Some aspects of the present disclosure relate to a compound of Formula (I), or a salt, or a mesomeric form thereof:

(I)

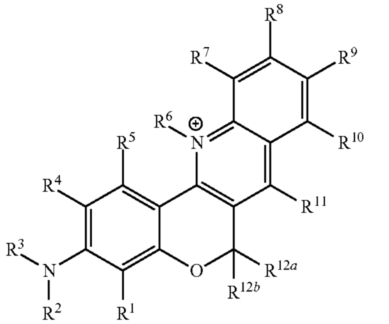

wherein each of $R^1$, $R^4$, $R^5$, $R^7$, $R^8$, $R^9$, $R^{10}$, $R^{11}$, $R^{12a}$ and $R^{12b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy)$C_1$-$C_6$ alkyl, optionally substituted amino, amino($C_1$-$C_6$ alkyl), halo, cyano, hydroxy, hydroxy($C_1$-$C_6$ alkyl), nitro, sulfonyl, sulfo, sulfino, sulfonate, S-sulfonamido, or N-sulfonamido;

each of $R^2$ and $R^3$ is independently H, $C_1$-$C_6$ alkyl, or substituted $C_1$-$C_6$ alkyl; and $R^6$ is $C_1$-$C_6$ alkyl or substituted $C_1$-$C_6$ alkyl;

alternatively, $R^1$ and $R^2$ together with the atoms to which they are attached form an optionally substituted 5-10 membered heteroaryl or an optionally substituted 5-10 membered heterocyclyl; and/or alternatively, $R^3$ and $R^4$ together with the atoms to which they are attached form an optionally substituted 5-10 membered heteroaryl or an optionally substituted 5-10 membered heterocyclyl; and/or alternatively, $R^8$ and $R^9$ together with the atoms to which they are attached form an optionally substituted $C_6$-$C_{10}$ aryl, an optionally substituted 3-10 membered carbocyclyl, an optionally substituted 5-10 membered heteroaryl or an optionally substituted 3-10 membered heterocyclyl. In some embodiments, when each of $R^2$ and $R^3$ is ethyl; each of $R^1$, $R^4$, $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl. In some embodiments, when $R^1$ and $R^2$ together with the atoms to which they are attached form a piperidinyl and $R^3$ and $R^4$ together with the atoms to which they are attached form a piperidinyl such that the compound has the structure

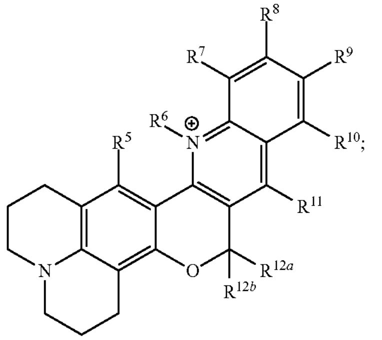

each of $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl.

In some embodiments, the compound of Formula (I) is also represented by Formula (Ia), or a salt or a mesomeric form thereof:

(Ia)

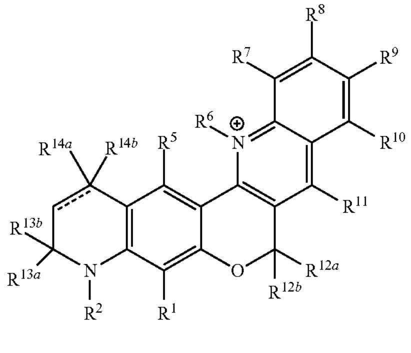

wherein each of $R^{13a}$, $R^{13b}$, $R^{14a}$ and $R^{14b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy)$C_1$-$C_6$ alkyl, optionally substituted amino, amino($C_1$-$C_6$ alkyl), halo, cyano, hydroxy, hydroxy($C_1$-$C_6$ alkyl), nitro, sulfonyl, sulfo, sulfino, sulfonate, S-sulfonamido, or N-sulfonamido; and the bond represented by a solid and dashed line ------ is selected from the group consisting of a single bond and a double bond, provided that when ------ is a double bond, then $R^{14b}$ is absent.

In some embodiments of the compounds of Formula (I) or (Ia), one of $R^6$, $R^7$, $R^8$, $R^9$, $R^{10}$ and $R^{11}$ comprises a carboxyl group (—C(O)OH). In other embodiments, $R^2$ or $R^3$ comprises a carboxyl group.

In some aspect, a compound of the present disclosure is labeled or conjugated with a substrate moiety such as, for example, a nucleoside, nucleotide, polynucleotide, polypeptide, carbohydrate, ligand, particle, cell, semi-solid surface (e.g., gel), or solid surface. The labeling or conjugation may be carried out via a carboxyl group, which can be reacted using methods known in the art with an amino or hydroxyl group on a moiety (such as a nucleotide) or a linker bound thereto, to form an amide or ester.

Some other aspects of the present disclosure relate to dye compounds comprising linker groups to enable, for example, covalent attachment to a substrate moiety. Linking may be carried out at any position of the dye, including at any of the R groups. In some embodiments, linking may be carried out via one of $R^6$, $R^7$, $R^8$, $R^9$, $R^{10}$ and $R^{11}$ or via $R^2$ or $R^3$ of Formula (I). In some further embodiments, linking may be carried out via one of $R^6$, $R^7$, $R^8$, $R^9$, $R^{10}$ and $R^{11}$ or via $R^2$ of Formula (Ia).

Some further aspects of the present disclosure provide a labeled nucleoside or nucleotide compound defined by the formula:

N-L-Dye wherein N is a nucleoside or nucleotide;

L is an optional linker moiety; and

Dye is a moiety of a fluorescent compound of Formula (I) or (Ia) according to the present disclosure, where a functional group of the compound of Formula (I) or (Ia) (e.g., a carboxyl group) reacts with an amino or hydroxyl group of the linker moiety or the nucleoside/nucleotide to form covalent bonding.

Some additional aspects of the present disclosure relate to nucleotide or oligonucleotide, labeled with a compound of Formula (I) or (Ia).

Some additional aspects of the present disclosure relate to a kit comprising a dye compound (free or in labeled form) that may be used in various immunological assays, oligonucleotide or nucleic acid labeling, or for DNA sequencing by synthesis. In yet another aspect, the disclosure provides kits comprising dye "sets" particularly suited to cycles of sequencing by synthesis on an automated instrument platform. In some aspect are kits containing one or more nucleotides where at least one nucleotide is a labeled nucleotide described herein.

A further aspect of the disclosure is a method of determining the sequence of a target polynucleotide, comprising:

(a) contacting a primer polynucleotide/target polynucleotide complex with one or more labeled nucleotides (e.g., A, G, C and T or dATP, dGTP, dCTP and dTTP), wherein at least one of said labeled nucleotide is a nucleotide described herein labeled with a chromenoquinoline dye of Formula (I) or (Ia), and wherein the primer polynucleotide is complementary to at least a portion of the target polynucleotide;

(b) incorporating a labeled nucleotide into the primer polynucleotide to produce an extended primer polynucleotide/target polynucleotide complex; and (c) performing one or more fluorescent measurements of the extended primer polynucleotide/target polynucleotide complex for determining the identity of the incorporated nucleotide.

DETAILED DESCRIPTION

Figure 1:
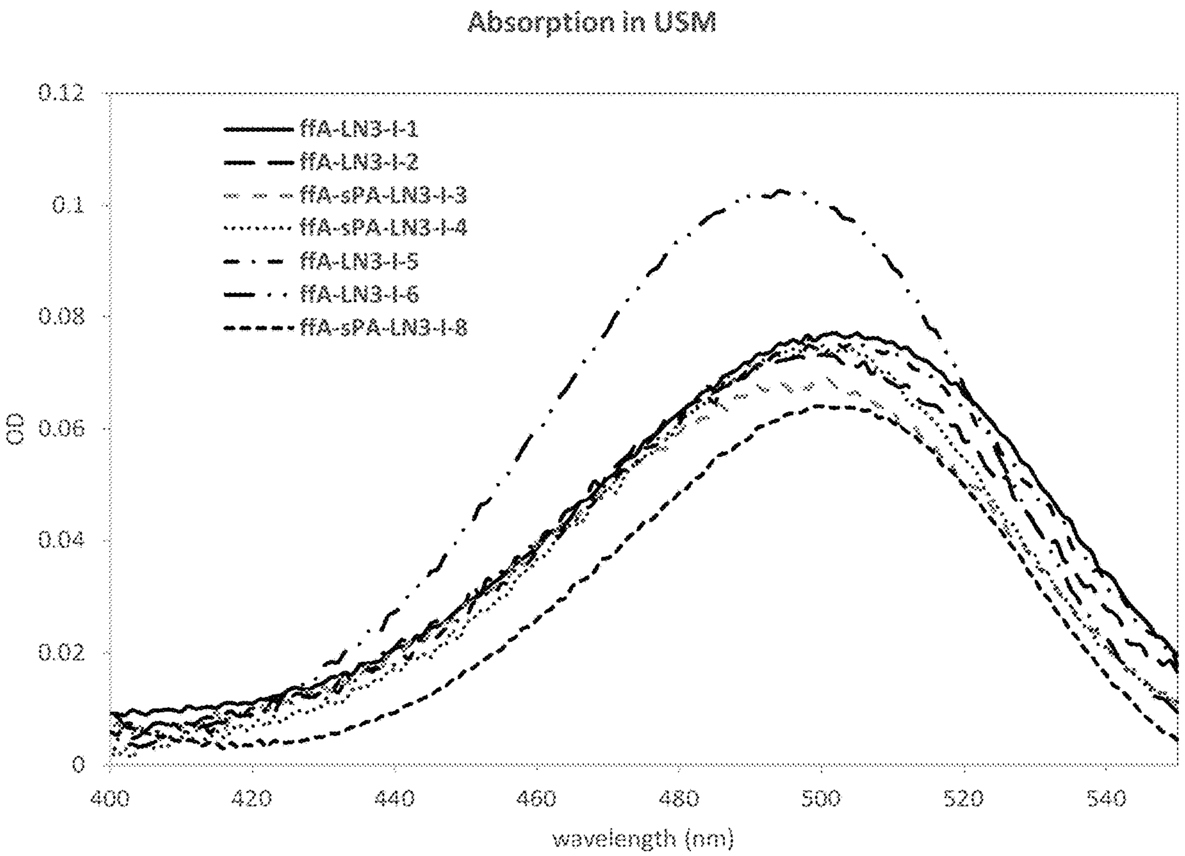
FIG. 1 illustrates the absorption spectra of ffA nucleotides conjugated with chromenoquinoline dyes I-1 through I-6 and I-8 as a 2 μM solution in Universal Scan Mix (USM).
Figure 2A:
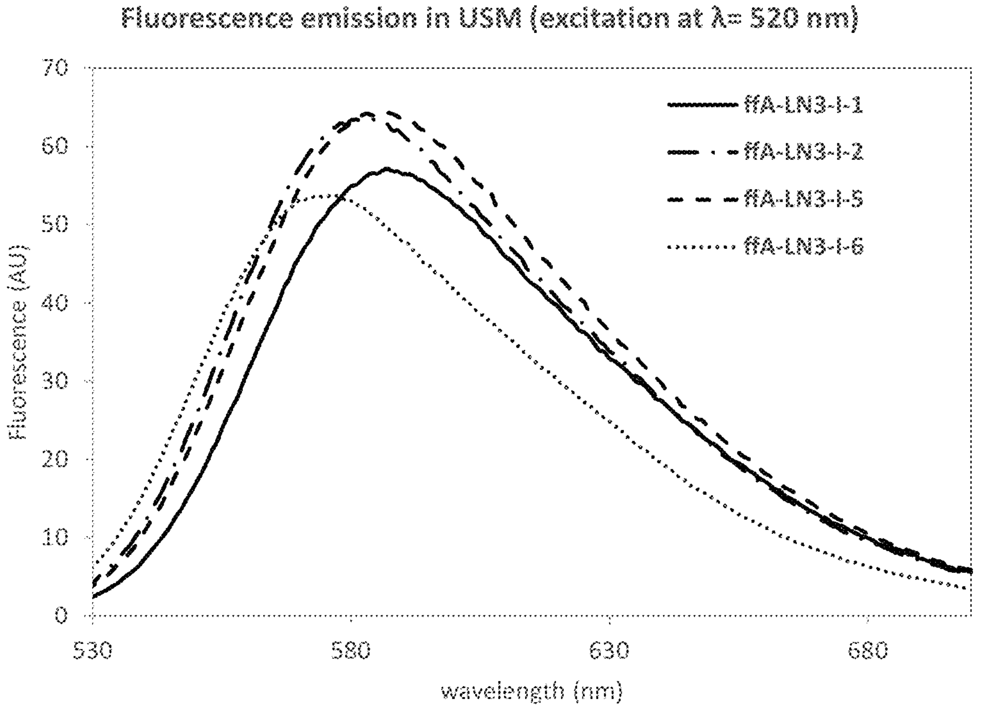
FIGS. 2A-2B show the fluorescence emission spectra of ffA nucleotides conjugated with chromenoquinoline dyes I-1, I-2, I-5 and I-6 acquired in USM using either 520 nm or 450 nm as excitation wavelength respectively.
Figure 2B:
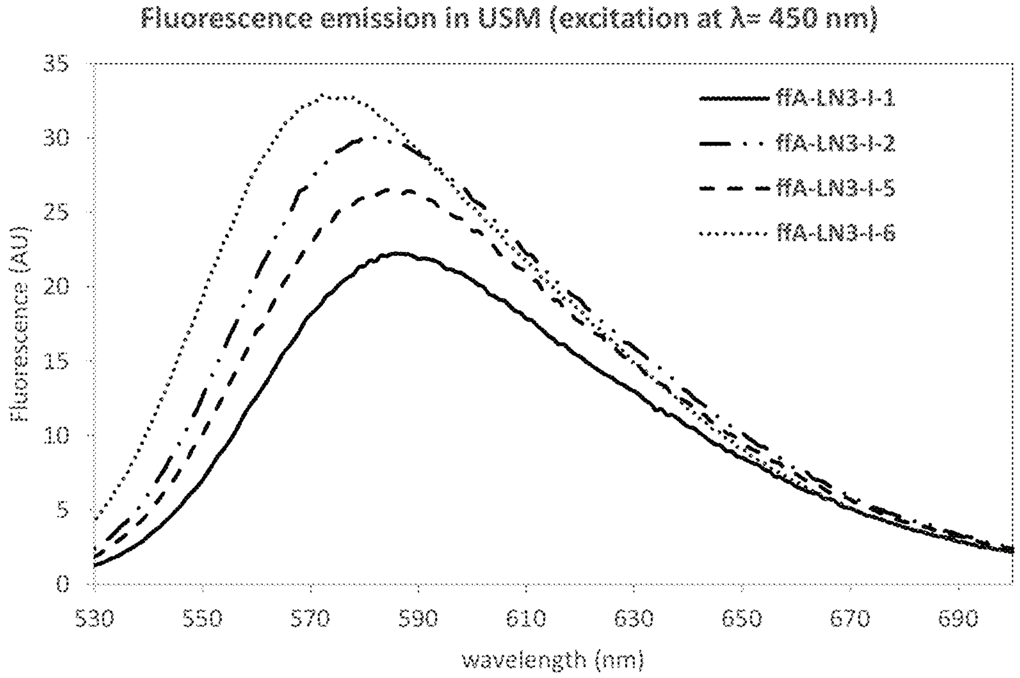
Figure 2C:
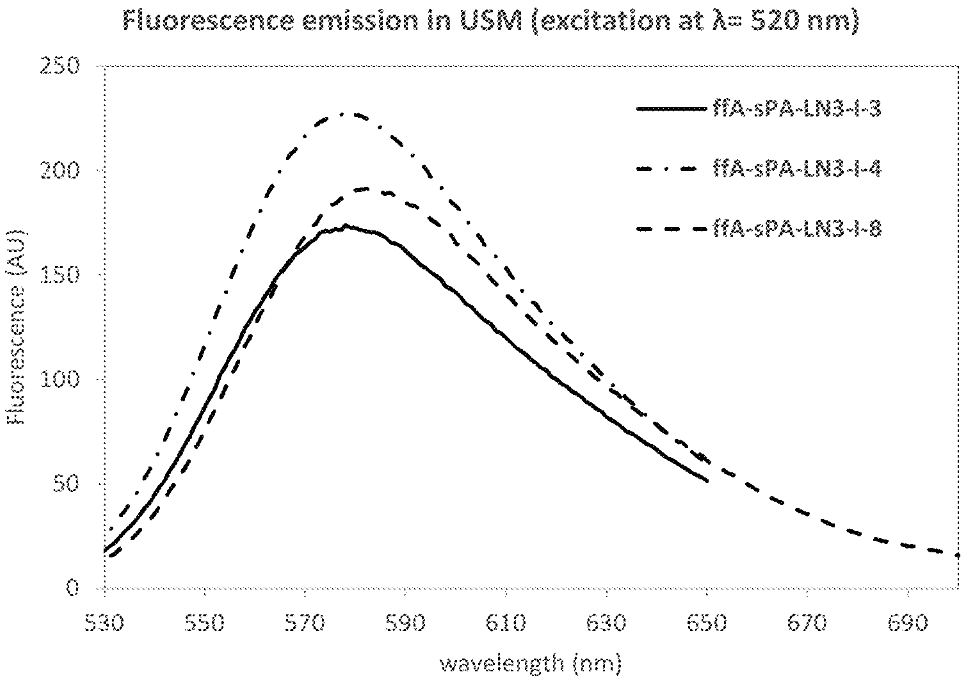
FIGS. 2C-2D show the fluorescence emission spectra of ffA nucleotides conjugated with chromenoquinoline dyes I-3, I-4 and I-8 acquired in USM using either 520 nm or 450 nm as excitation wavelength respectively.
Figure 2D:
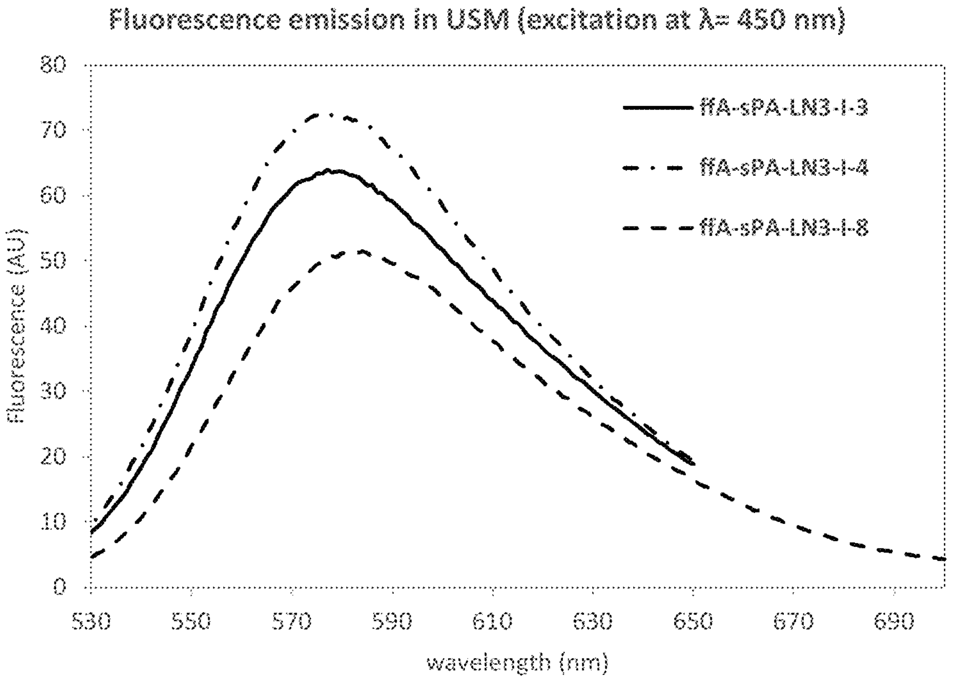

Embodiments of the present disclosure relate to chromenoquinoline dyes with enhanced fluorescent intensity, long Stokes shift and improved chemical stability, particularly in high pH aqueous environment. These chromenoquinoline dyes also have a wide excitation wavelength and may be excited by both blue and green light sources. In some embodiments, the chromenoquinoline dyes described herein may be used in Illumina's iSeg™ platform with two-channel CMOS detection (green light excitation and blue light excitation).

Definitions

The section headings used herein are for organizational purposes only and are not to be construed as limiting the subject matter described.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps but may include additional steps. When used in the context of a compound, composition, or device, the term "comprising" means that the compound, composition, or device includes at least the recited features or components, but may also include additional features or components.

As used herein, common organic abbreviations are defined as follows:

° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP Dideoxynucleotide triphosphate
ffA Fully functionalized A nucleotide
ffC Fully functionalized C nucleotide
ffG Fully functionalized G nucleotide
ffN Fully functionalized nucleotide
ffT Fully functionalized T nucleotide
h Hour(s)
RT Room temperature
SBS Sequencing by Synthesis As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-$C_5$ alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc. $C_3$-$C_8$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. By way of example only, "$C_{1-6}$ alkyl" or "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as ""$C_{1-9}$ alkoxy" or "$C_1$-$C_9$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. By way of example only, "$C_2$-$C_6$ alkenyl" or "$C_{2-6}$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4- yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. By way of example only, "$C_{2-6}$ alkynyl" or "$C_{2}$-$C_6$alkenyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl", "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro [4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "alkoxyalkyl" or "(alkoxy)alkyl" refers to an alkoxy group connected via an alkylene group, such as $C_2$-$C_8$alkoxyalkyl, or ($C_1$-$C_6$ alkoxy)$C_1$-$C_6$ alkyl, for example, $—(CH_2)_{1-3}—OCH_3$.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(═O)OR" group in which R is selected from the group consisting of hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(═O)OH).

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfino" group refers to a "—S(═O)OH" group.

A "sulfo" group refers to a "—S(═O)$_2$OH" or "—$SO_3$H" group.

A "sulfonate" group refers to a "—$SO_3^-$" group.

A "sulfate" group refers to "—$SO_4^-$" group.

A "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—N($R_A$)$SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(═O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—N($R_A$)C(═O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_2$-$C_8$ alkoxyalkyl" and the like.

When a group is described as "optionally substituted" it may be either unsubstituted or substituted. Likewise, when a group is described as being "substituted", the substituent may be selected from one or more of the indicated substituents. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3$H, sulfonate, sulfate, sulfino, —$OSO_2C_1$-$C_4$alkyl, and oxo (═O). Wherever a group is described as "optionally substituted" that group can be substituted with the above substituents. In some embodiments, when an alkyl, alkenyl, alkynyl, aryl, heteroaryl, carbocyclyl or heterocyclyl group is substituted, each is independently substituted with one or more substituents selected from the group consisting of halo, —CN, —$SO_3$, —$OSO_3$, —$SO_3$H, —$SR^A$, —$OR^A$, —$NR^BR^C$, oxo, —$CONR^BR^C$, —$SO_2NR^BR^C$, —COOH, and —$COOR^B$, where $R^A$, $R^B$ and $R^C$ are each independently selected from H, alkyl, substituted alkyl, alkenyl, substituted alkenyl, alkynyl, substituted alkynyl, aryl, and substituted aryl.

As understood by one of ordinary skill in the art, a compound described herein may exist in ionized form, e.g., —$CO_2$, —$SO_3$ or —O—$SO_3^-$. If a compound contains a positively or negatively charged substituent group, for example, —$SO_3$, it may also contain a negatively or positively charged counterion such that the compound as a whole is neutral. In other aspects, the compound may exist in a salt form, where the counterion is provided by a conjugate acid or base.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two "adjacent" R groups are said to form a ring "together with the atom to which they are attached," it is meant that the collective unit of the atoms, intervening bonds, and the two R groups are the recited ring. For example, when the following substructure is present:

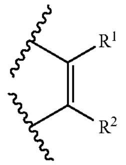

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

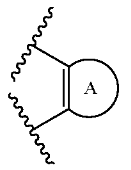

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

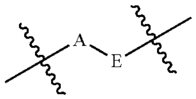

includes the substituent being oriented such that the A is attached at the leftmost attachment point of the molecule as well as the case in which A is attached at the rightmost attachment point of the molecule. In addition, if a group or substituent is depicted as

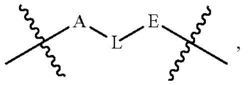

and L is defined an optionally present linker moiety; when L is not present (or absent), such group or substituent is equivalent to

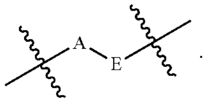

In each instance where a single mesomeric form of a compound described herein is shown, the alternative mesomeric forms are equally contemplated.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine, deazapurine, or pyrimidine base. Purine bases include adenine (A) and guanine (G), and modified derivatives or analogs thereof, such as 7-deaza adenine or 7-deaza guanine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, deazapurine, 7-deaza adenine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, the term "cleavable linker" is not meant to imply that the whole linker is required to be removed. The cleavage site can be located at a position on the linker that ensures that part of the linker remains attached to the detectable label and/or nucleoside or nucleotide moiety after cleavage.

As used herein, "derivative" or "analog" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

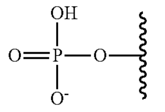 and 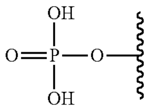 ).

As used herein, the terms "monophosphate," "diphosphate," and "triphosphate" are used in their ordinary sense as understood by those skilled in the art, and include protonated forms.

As used herein, the term "phasing" refers to a phenomenon in SBS that is caused by incomplete removal of the 3' terminators and fluorophores, and/or failure to complete the incorporation of a portion of DNA strands within clusters by polymerases at a given sequencing cycle. Prephasing is caused by the incorporation of nucleotides without effective 3' terminators, wherein the incorporation event goes 1 cycle ahead due to a termination failure. Phasing and prephasing cause the measured signal intensities for a specific cycle to consist of the signal from the current cycle as well as noise from the preceding and following cycles. As the number of cycles increases, the fraction of sequences per cluster affected by phasing and prephasing increases, hampering the identification of the correct base. Prephasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of prephasing is surprising and provides a great advantage in SBS applications over existing nucleotide analogues. For example, the nucleotide analogues provided can result in faster SBS cycle time, lower phasing and prephasing values, and longer sequencing read lengths.

Chromenoquinoline Dyes of Formula (I)

Some aspects of the disclosure relate to chromenoquinoline dyes of Formula (I), and salts and mesomeric forms thereof:

(I)

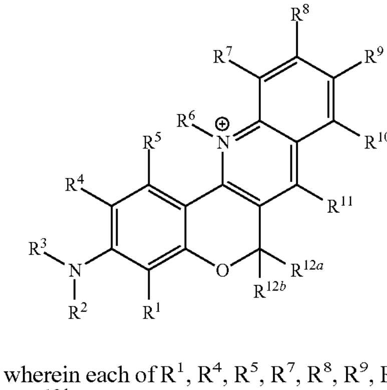

wherein each of $R^1$, $R^4$, $R^5$, $R^7$, $R^8$, $R^9$, $R^{10}$, $R^{11}$, $R^{12a}$ and $R^{12b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy)$C_1$-$C_6$ alkyl, optionally substituted amino, amino($C_1$-$C_6$ alkyl), halo, cyano, hydroxy, hydroxy($C_1$-$C_6$ alkyl), nitro, sulfonyl, sulfo, sulfino, sulfonate, S-sulfonamido, or N-sulfonamido;

each of $R^2$ and $R^3$ is independently H, $C_1$-$C_6$ alkyl, or substituted $C_1$-$C_6$ alkyl; and $R^6$ is $C_1$-$C_6$ alkyl or substituted $C_1$-$C_6$ alkyl;

alternatively, $R^1$ and $R^2$ together with the atoms to which they are attached form an optionally substituted 5-10 membered heteroaryl or an optionally substituted 5-10 membered heterocyclyl; and/or alternatively, $R^3$ and $R^4$ together with the atoms to which they are attached form an optionally substituted 5-10 membered heteroaryl or an optionally substituted 5-10 membered heterocyclyl; and/or alternatively, $R^8$ and $R^9$ together with the atoms to which they are attached form an optionally substituted $C_6$-$C_{10}$ aryl, an optionally substituted 3-10 membered carbocyclyl, an optionally substituted 5-10 membered heteroaryl or an optionally substituted 3-10 membered heterocyclyl;

provided that when each of $R^2$ and $R^3$ is ethyl; each of $R^1$, $R^4$, $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl; and provided that when $R^1$ and $R^2$ together with the atoms to which they are attached form a piperidinyl and $R^3$ and $R^4$ together with the atoms to which they are attached form a piperidinyl such that the compound has the structure

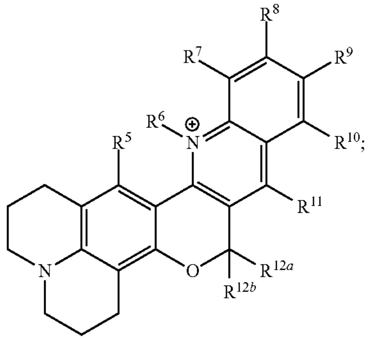

each of $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl.

In any embodiments of the compound of Formula (I), when a group is defined as a substituted $C_1$-$C_6$ alkyl, it may be a $C_1$, $C_2$, $C_3$, $C_4$, $C_5$ or $C_6$ alkyl substituted with carboxyl, carboxylate, sulfo, sulfonate, —C(O)OR$^{15}$ or —C(O)NR$^{16}$R$^{17}$, and wherein each $R^{16}$ and $R^{17}$ is independently H or $C_1$-$C_6$ alkyl substituted with carboxyl, carboxylate, —C(O)OR$^{15}$, sulfo or sulfonate.

In some embodiments of the compound of Formula (I), at least one of $R^2$ and $R^3$ is H. In some further embodiments, both $R^2$ and $R^3$ are H. In other embodiments, $R^2$ is H and $R^3$ is $C_1$-$C_6$ alkyl or substituted $C_1$-$C_6$ alkyl. In other embodiments, each of $R^2$ and $R^3$ is independently $C_1$-$C_6$ alkyl or substituted $C_1$-$C_6$ alkyl. Substituted $C_1$-$C_6$ alkyl include but not limited to methyl, ethyl, isopropyl, n-propyl, n-butyl, 2-butyl, n-pentyl, 2-pentyl, n-hexyl, etc. substituted with one or more substituents such as carboxyl, carboxylate (—C(O)O), sulfo (—$SO_3$H), sulfonate (—$SO_3$), sulfate (—O—$SO_3^-$), an optionally substituted amino (such as a Boc protected amino group), —C(O)OR$^{15}$, or —C(O)NR$^{16}$R$^{17}$, wherein $R^{15}$ is optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl, and wherein each of $R^{16}$ and $R^{17}$ is independently H, optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl. In one embodiment, each of $R^2$ and $R^3$ is ethyl. In another embodiment, $R^2$ is H and $R^3$ is n-propyl substituted with a carboxyl.

In any embodiments of the compound of Formula (I), when a group is defined as a substituted $C_1$-$C_6$ alkyl, it may be a $C_1$, $C_2$, $C_3$, $C_4$, $C_5$ or $C_6$ alkyl substituted with carboxyl, carboxylate, sulfo, sulfonate, —C(O)OR$^{15}$ or —C(O)NR$^{16}$R$^{17}$, and wherein each $R^{16}$ and $R^{17}$ is independently H or $C_1$-$C_6$ alkyl substituted with carboxyl, carboxylate, —C(O)OR$^{15}$, sulfo or sulfonate.

Some embodiments of the compounds of Formula (I) are also represented by Formula (Ia), where $R^3$ and $R^4$ of Formula (I) together with the atoms to which they are attached form optionally substituted 6 membered heterocyclyl of the following structure:

(Ia)

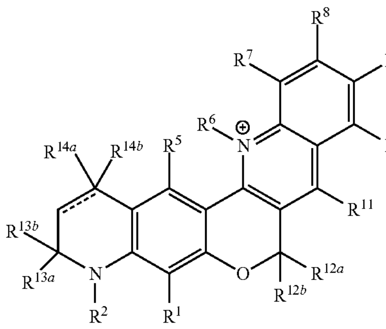

a salt or a mesomeric form thereof:

wherein each of $R^{3a}$, $R^{13b}$, $R^{14a}$ and $R^{14b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy)$C_1$-$C_6$ alkyl, optionally substituted amino, amino($C_1$-$C_6$ alkyl), halo, cyano, hydroxy, hydroxy($C_1$-$C_6$ alkyl), nitro, sulfonyl, sulfo, sulfino, sulfonate, S-sulfonamido, or N-sulfonamido; and the bond represented by a solid and dashed line ⎓ is selected from the group consisting of a single bond and a double bond, provided that when ⎓ is a double bond, then $R^{14b}$ is absent.

In some embodiments of the compounds of Formula (Ia), the bond represented by a solid and dashed line ⎓ is a double bond. In some such embodiments, $R^{14a}$ is H or $C_1$-$C_6$ alkyl (for example, methyl, ethyl, isopropyl, n-propyl, n-butyl, 2-butyl, n-pentyl, 2-pentyl, or n-hexyl, etc). In one embodiment, $R^{14a}$ is methyl. In other embodiments of the compounds of Formula (Ia), the bond represented by a solid and dashed line ⎓ is a single bond. In some such embodiments, $R^{14a}$ is H and $R^{14b}$ is $C_1$-$C_6$ alkyl (for example, methyl, ethyl, isopropyl, n-propyl, n-butyl, 2-butyl, n-pentyl, 2-pentyl, or n-hexyl, etc). In some such embodiments, each of $R^{14a}$ and $R^{14b}$ is H. In some embodiments, each of $R^{13a}$ and $R^{13b}$ is H. In other embodiments, each of $R^{13a}$ and $R^{13b}$ is $C_1$-$C_6$ alkyl. In one embodiment, each of $R^{13a}$ and $R^{13b}$ methyl.

In some embodiments of the compounds of Formula (Ia), $R^2$ is H. In other embodiments, $R^2$ is $C_1$-$C_6$ alkyl or substituted $C_1$-$C_6$ alkyl (for example, methyl, ethyl, isopropyl, n-propyl, n-butyl, 2-butyl, n-pentyl, 2-pentyl, or n-hexyl, etc). In some further embodiments, $R^2$ is $C_1$-$C_6$ alkyl substituted with one or more substituents selected from the group consisting of carboxyl (—C(O)OH), carboxylate (—C(O)O$^-$), sulfo (—$SO_3$H), sulfonate (—$SO_3^-$), —C(O)OR$^{15}$, and —C(O)NR$^{16}$R$^{17}$, wherein $R^{15}$ is optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl, and wherein each of $R^{16}$ and $R^{17}$ is independently H, optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl. In some further embodiments, $R^2$ is $C_1$-$C_6$ alkyl substituted with carboxyl or —C(O)NR$^{16}$R$^{17}$, and wherein each $R^{16}$ and $R^{17}$ is independently $C_1$-$C_6$ alkyl substituted with carboxyl, carboxylate, —C(O)OR$^{15}$, sulfo or sulfonate. In some embodiments, the substitution is at the terminal of the straight chain $C_2$, $C_3$, $C_5$, $C_6$, or $C_6$ alkyl. In one embodiment, $R^3$ is n-propyl substituted with carboxyl.

In some embodiments of the compounds of Formula (I) or (Ia), $R^1$ is H. In other embodiments, $R^1$ and $R^2$ are joined together with the atoms to which they are attached to form an optionally substituted 5, 6 or 7 membered heterocyclyl. In some such embodiments, $R^1$ and $R^2$ are joined together with the atoms to which they are attached to form a 6 membered heterocyclyl substituted with one or more $C_1$-$C_6$ alkyl.

In some embodiments of the compounds of Formula (I) or (Ia), $R^6$ is $C_1$-$C_6$ alkyl. In one embodiment, $R^6$ is methyl. In other embodiments, $R^6$ is $C_1$-$C_6$ alkyl substituted with carboxyl or —C(O)NR$^{16}$R$^{17}$, and wherein each $R^{16}$ and $R^{17}$ is independently $C_1$-$C_6$ alkyl substituted with carboxyl, carboxylate, —C(O)OR$^{15}$, sulfo or sulfonate.

In some embodiments of the compounds of Formula (I) or (Ia), $R^5$ is H. In some further embodiments, $R^{11}$ is H. In some further embodiments, each of $R^{12a}$ and $R^{12b}$ is H.

In some embodiments of the compounds of Formula (I) or (Ia), at least one of $R^7$, $R^8$, $R^9$ and $R^{10}$ is H. In one such embodiment, each of $R^7$, $R^8$, $R^9$ and $R^{10}$ is H. In another such embodiment, each of $R^7$, $R^8$, and $R^{10}$ is H. In another such embodiment, each of $R^7$ and $R^{10}$ is H. In other embodiments, at least one of $R^7$, $R^8$, $R^9$ and $R^{10}$ is independently $C_1$-$C_6$ alkyl (for example, methyl, ethyl, isopropyl, n-propyl, n-butyl, 2-butyl, n-pentyl, 2-pentyl, or n-hexyl, etc) or $C_1$-$C_6$ alkoxy (for example, methoxy, ethoxy, n-propoxy, isopropxy, n-butoxy, 2-butoxy, n-pentoxy, 2-pentoxy, n-hexoxy, etc.). In one such embodiment, $R^9$ is methyl or methoxy. In another such embodiment, each of $R^8$ and $R^9$ is methyl or methoxy. In yet another embodiment, each of $R^8$, $R^9$ and $R^{10}$ is methyl or methoxy. In other embodiments, at least one of $R^7$, $R^8$, $R^9$ and $R^{10}$ is $C_1$-$C_6$ alkyl substituted carboxyl, carboxylate, sulfo, sulfonate —C(O)OR$^{15}$ or —C(O)NR$^{16}$R$^{17}$, wherein each $R^{16}$ and $R^{17}$ is independently H or $C_1$-$C_6$ alkyl substituted with carboxyl, carboxylate, —C(O)OR$^{15}$, sulfo or sulfonate. In other embodiments, $R^8$ and $R^9$ together with the atoms to which they are attached form an optionally substituted 5 or 6 membered heterocyclyl, for example, those with the structure such as:

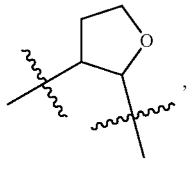

,

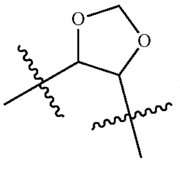

,

-continued
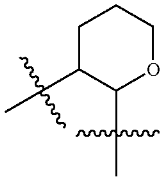 or 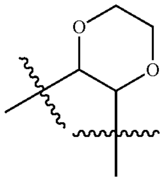 .
Additional embodiments of the compound of Formula (I) or (Ia) include the following:
(I-1)
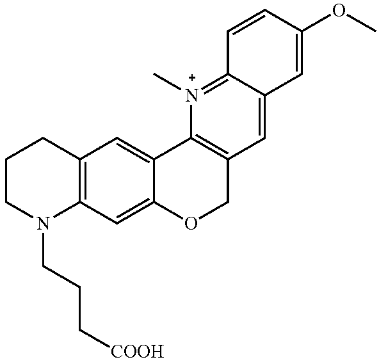
,
(I-2)
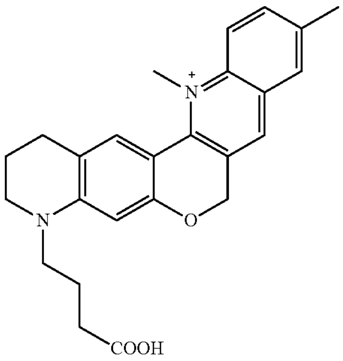
,
(I-3)
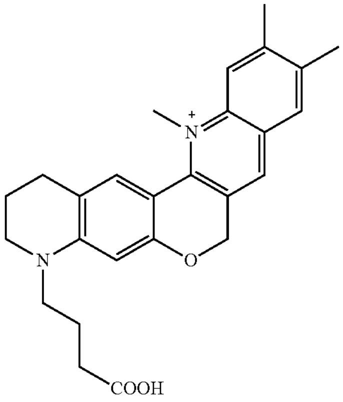
,
-continued
(I-4)
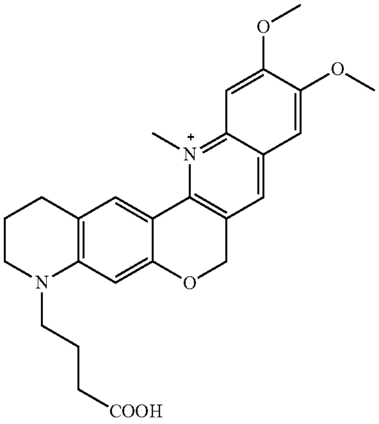
,
(I-5)
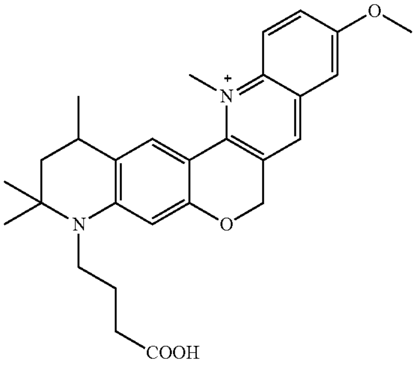
,
(I-6)
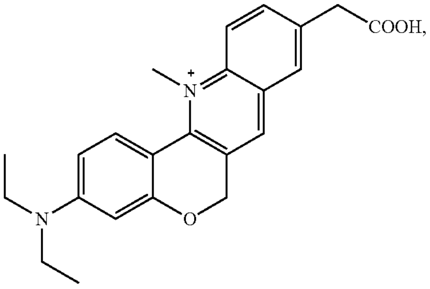
(I-7)
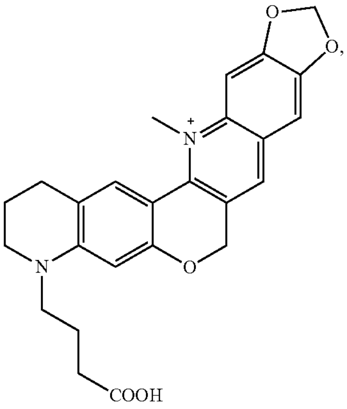

-continued (I-8)

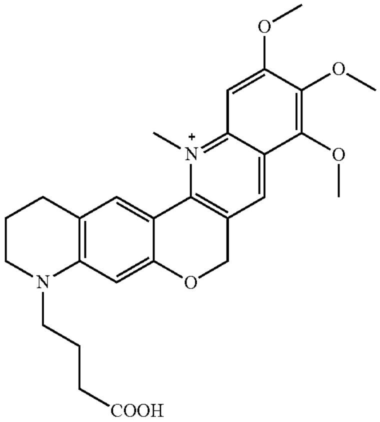

, (I-9)

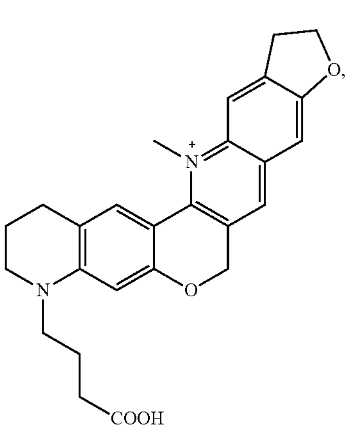

and (I-10)

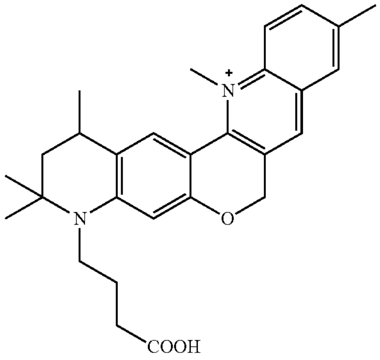

, and salts and mesomeric forms thereof. Non-limiting examples corresponding $C_1$-$C_6$ alkyl carboxylic esters (such as methyl esters, ethyl esters isopropyl esters, and t-butyl esters formed from the carboxylic group of the compounds).

Cyclooctatetraene (COT) Photo-Protecting Moieties

In some embodiments, the fluorescent compounds described herein (Formula (I) or (Ia)) may be further modified to introduce a photo-protecting moiety covalently bonded thereto, for example, a cyclooctatetraene moiety comprises the structure:

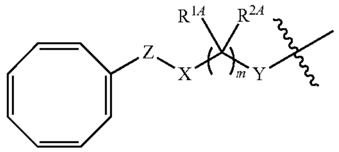

, wherein each of $R^{1A}$ and $R^{2A}$ is independently H, hydroxyl, halogen, azido, thiol, nitro, cyano, optionally substituted amino, carboxyl, —C(O)OR$^{5A}$, —C(O)NR$^{6A}$R$^{7A}$, optionally substituted $C_{1-6}$ alkyl, optionally substituted $C_{1-6}$ alkoxy, optionally substituted $C_{1-6}$ haloalkyl, optionally substituted $C_{1-6}$ haloalkoxy, optionally substituted $C_{2-6}$ alkenyl, optionally substituted $C_{2-6}$ alkynyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

$X^1$ and $Y^1$ are each independently a bond, —O—, —S—, —NR$^{3A}$—, —C(═O)—, —C(═O)—O—, —C(═O)—NR$^{4A}$—, —S(O)$_2$—, —NR$^{3A}$—C(═O)—NR$^{4A}$, —NR$^{3A}$—C(═S)—NR$^{4A}$—, optionally substituted $C_{1-6}$ alkylene, or optionally substituted heteroalkylene where at least one carbon atom is replaced with O, S, or N;

Z is absent, optionally substituted $C_{2-6}$ alkenylene, or optionally substituted $C_{2-6}$ alkynylene;

each of $R^{3A}$ and $R^{4A}$ is independently H, optionally substituted $C_{1-6}$ alkyl, or optionally substituted $C_{6-10}$ aryl;

$R^{5A}$ is optionally substituted $C_{1-6}$ alkyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

each of $R^{6A}$ and $R^{7A}$ is independently H, optionally substituted $C_{1-6}$ alkyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

the carbon atom to which $R^{1A}$ and $R^{2A}$ are attached in

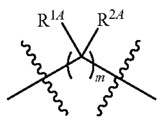

is optionally replaced with O, S, or N, provided that when said carbon atom is replaced with O or S, then $R^{1A}$ and $R^{2A}$ are both absent; when said carbon atom is replaced with N, then $R^{2A}$ is absent; and m is an integral number between 0 and 10. In some embodiments, X and Y are not both a bond.

In some embodiments, the cyclooctatetraene moiety comprises the structure

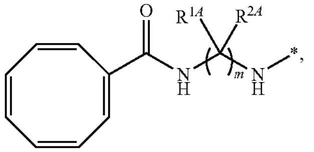

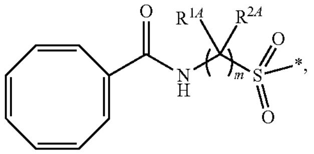

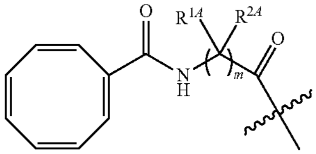

or

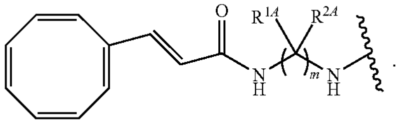

In some such embodiments, at least one of $R^{1A}$ and $R^{2A}$ is hydrogen. In some further embodiments, both $R^{1A}$ and $R^{2A}$ are hydrogen. In some other embodiments, $R^{1A}$ is H and $R^{2A}$ is an optionally substituted amino, carboxyl or —C(O)NR$^{6A}$R$^{7A}$. In some embodiments, m is 1, 2, 3, 4, 5, or 6, and each of $R^{1A}$ and $R^{2A}$ is independently hydrogen, optionally substituted amino, carboxyl, —C(O)NR$^{6A}$R$^{7A}$, or combinations thereof. In some further embodiments, when m is 2, 3, 4, 5, or 6, one $R^{1A}$ is amino, carboxyl, or —C(O)NR$^{6A}$R$^{7A}$, and the remaining $R^{1A}$ and $R^{2A}$ are hydrogen. In some embodiments, at least one carbon atom to which $R^{1A}$ and $R^{2A}$ are attached in

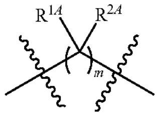

is replaced with O, S, or N. In some such embodiments, one carbon atom in

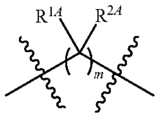

is replaced by an oxygen atom, and both $R^{1A}$ and $R^{2A}$ attached to said replaced carbon atom are absent. In some other embodiments, when one carbon atom in

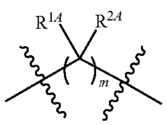

is replaced by a nitrogen atom, $R^{2A}$ attached to said replaced carbon atom is absent, and $R^{1A}$ attached to said replaced carbon atom is hydrogen, or $C_{1-6}$ alkyl. In any embodiments of $R^{1A}$ and $R^{2A}$, when $R^{1A}$ or $R^{2A}$ is —C(O)NR$^{6A}$R$^{7A}$, $R^{6A}$ and $R^{7A}$ may be independently H, $C_{1-6}$ alkyl or substituted $C_{1-6}$ alkyl (e.g., $C_{1-6}$ alkyl substituted with —$CO_2H$, —$NH_2$, —$SO_3H$, or —$SO_3^-$).

In some further embodiments, the fluorescent dyes described herein comprises a cyclooctatetraene moiety of the following structures:

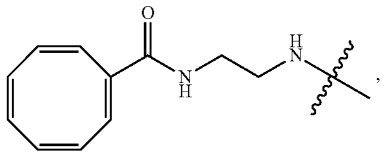

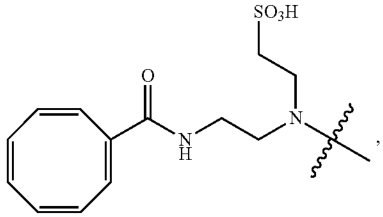

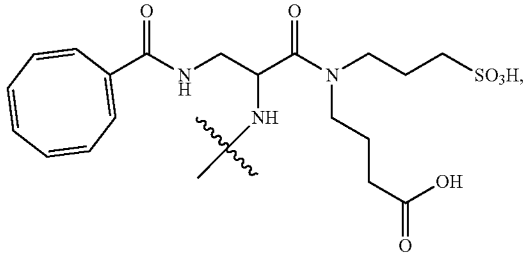

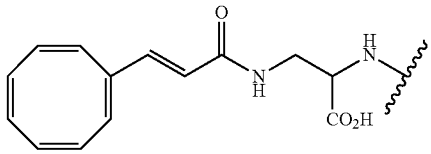

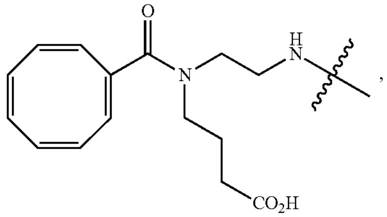

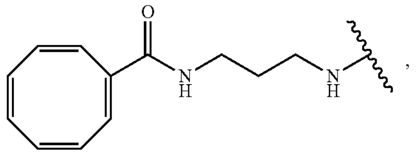

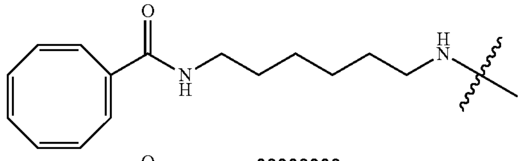

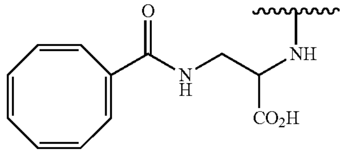

or

-continued

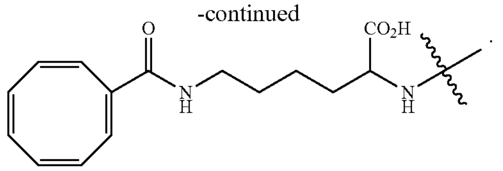

The COT moiety described herein may result from the reaction between a functional group of the fluorescent dye described herein (e.g., a carboxyl group) and an amino group of a COT derivative to form an amide bond (where the carbonyl group of the amide bond is not shown).

Labeled Nucleotides or Oligonucleotides

According to an aspect of the disclosure, dye compounds described herein are suitable for attachment to substrate moieties, particularly comprising linker groups to enable attachment to substrate moieties. Substrate moieties can be virtually any molecule or substance to which the dyes of the disclosure can be conjugated, and, by way of non-limiting example, may include nucleosides, nucleotides, polynucleotides, carbohydrates, ligands, particles, solid surfaces, organic and inorganic polymers, chromosomes, nuclei, living cells, and combinations or assemblages thereof. The dyes can be conjugated by an optional linker by a variety of means including hydrophobic attraction, ionic attraction, and covalent attachment. In some aspect, the dyes are conjugated to the substrate by covalent attachment. More particularly, the covalent attachment is by means of a linker group. In some instances, such labeled nucleotides are also referred to as “modified nucleotides.”

Some aspects of the present disclosure relate to a nucleotide or oligonucleotide labeled with a dye of Formula (I) or (Ia), or a salt of mesomeric form thereof as described herein, or a derivative thereof containing a photo-protecting moiety COT described herein. The labeled nucleotide or oligonucleotide may be attached to the dye compound disclosed herein via a carboxyl (—$CO_2H$) or an alkyl-carboxyl group to form an amide or alkyl-amide bond. In some further embodiments, the carboxyl group may be in the form of an activated form of carboxyl group, for example, an amide or ester, which may be used for attachment to an amino or hydroxyl group of the nucleotide or oligonucleotide. The term “activated ester” as used herein, refers to a carboxyl group derivative which is capable of reacting in mild conditions, for example, with a compound containing an amino group. Non-limiting examples of activated esters include but not limited to p-nitrophenyl, pentafluorophenyl and succinimido esters.

For example, the dye compound of Formula (I) may be attached to the nucleotide or oligonucleotide via one of $R^6$, $R^7$, $R^8$, $R^9$, $R^{10}$ and $R^{11}$ or one of $R^2$/$R^3$ of Formula (I). In some such embodiments, $R^9$ of Formula (I) comprises a —$CO_2H$ or —$(CH_2)_{1-6}$—$CO_2H$ and the attachment forms an amide moiety between the carboxyl functional group of $R^9$ and the amino functional group of a nucleotide or a nucleotide linker. As one example, the labeled nucleotide or oligonucleotide may comprise the dye moiety of the following structure:

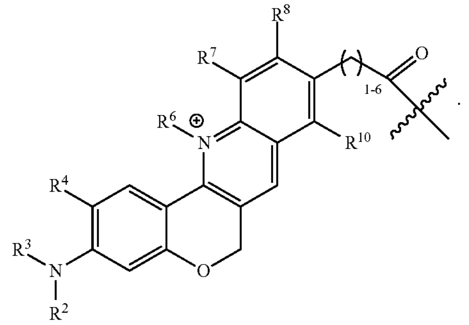

In other embodiments, $R^2$ or $R^3$ of Formula (I) comprises a —$CO_2H$ or —$(CH_2)_{1-6}$—$CO_2H$ and the attachment forms an amide using the —$CO_2H$ group. For example, the labeled nucleotide or oligonucleotide may comprise the following dye moiety:

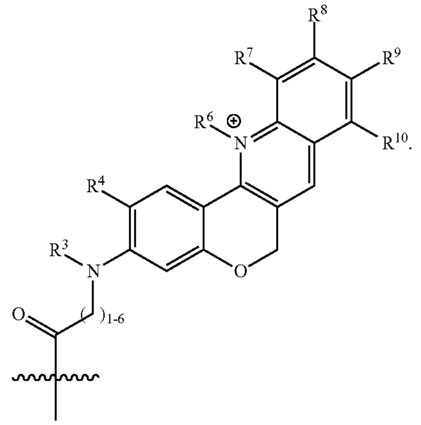

Similarly, the dye compound of Formula (Ia) may be attached to the nucleotide or oligonucleotide via one of $R^6$, $R^7$, $R^8$, $R^9$, $R^{10}$ and $R^{11}$ (e.g., $R^9$), or $R^2$ of Formula (Ia) by forming an amide moiety between the carboxyl functional group of the compound and an amino functional group of a nucleotide or a nucleotide linker. For example, the labeled nucleotide or oligonucleotide may comprise the following dye moiety:

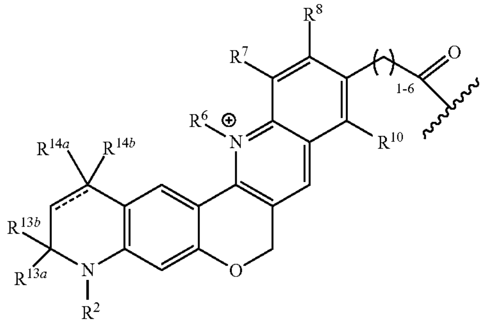

or

-continued

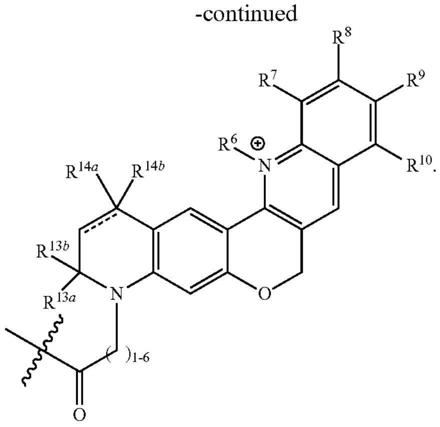

In other embodiments, $R^6$ of Formula (I) or (Ia) comprises a $-CO_2H$ or $-(CH_2)_{1-6}-CO_2H$ and the attachment forms an amide using the $-CO_2H$ group.

In some embodiments, the dye compounds may be covalently attached to oligonucleotides or nucleotides via the nucleotide base. In some such embodiments, the labeled nucleotide or oligonucleotide may have the dye attached to the C5 position of a pyrimidine base or the C7 position of a 7-deaza purine base, optionally through a linker moiety. For example, the nucleobase may be 7-deaza adenine, and the dye is attached to the 7-deaza adenine at the C7 position, optionally through a linker. The nucleobase may be 7-deaza guanine, and the dye is attached to the 7-deaza guanine at the C7 position, optionally through a linker. The nucleobase may be cytosine and the dye is attached to the cytosine at the C5 position, optionally through a linker. As another example, the nucleobase may be thymine or uracil and the dye is attached to the thymine or uracil at the C5 position, optionally through a linker.

3' Hydroxyl Blocking Groups

The labeled nucleotide or oligonucleotide may also have a blocking group covalently attached to the ribose or deoxyribose sugar of the nucleotide. The blocking group may be attached at any position on the ribose or deoxyribose sugar. In particular embodiments, the blocking group is at the 3' OH position of the ribose or deoxyribose sugar of the nucleotide. Various 3' OH blocking group are disclosed in WO2004/018497 and WO2014/139596, which are hereby incorporated by references. For example, the blocking group may be azidomethyl ($-CH_2N_3$) or substituted azidomethyl (e.g., $-CH(CHF_2)N_3$ or $CH(CH_2F)N_3$), or allyl connecting to the 3' oxygen atom of the ribose or deoxyribose moiety. In some embodiments, the 3' blocking group is azidomethyl, forming $3'-OCH_2N_3$ with the 3' carbon of the ribose or deoxyribose.

In some other embodiments, the 3' blocking group and the 3' oxygen atoms form an acetal group of the structure

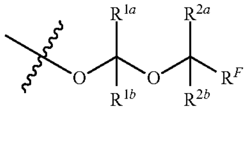

covalent attached to the 3' carbon of the ribose or deoxyribose, wherein:

each $R^{1a}$ and $R^{1b}$ is independently H, $C_1$-$C_6$ alkyl, $C_1$-$C_6$ haloalkyl, $C_1$-$C_6$ alkoxy, $C_1$-$C_6$ haloalkoxy, cyano, halogen, optionally substituted phenyl, or optionally substituted aralkyl;

each $R^{2a}$ and $R^{2b}$ is independently H, $C_1$-$C_6$ alkyl, $C_1$-$C_6$ haloalkyl, cyano, or halogen;

alternatively, $R^{1a}$ and $R^{2a}$ a together with the atoms to which they are attached form an optionally substituted five to eight membered heterocyclyl group;

$R^F$ is H, optionally substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)$Si(R^{3a})_3$; and each $R^{3a}$ is independently H, $C_1$-$C_6$ alkyl, or optionally substituted $C_6$-$C_{10}$ aryl.

Additional 3' OH blocking groups are disclosed in U.S. Publication No. 2020/0216891 A1, which is incorporated by reference in its entirety. Non-limiting examples of the acetal blocking group

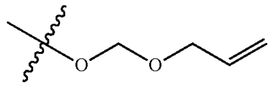, (AOM)

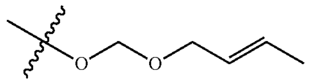,

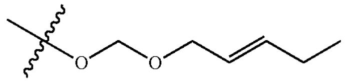,

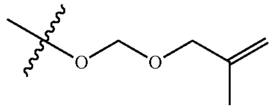,

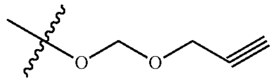,

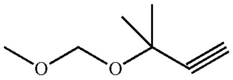, 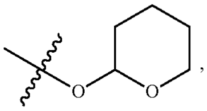, and

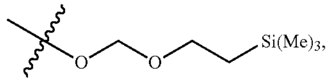, each covalently attached to the 3' carbon of the ribose or deoxyribose.

Deprotection of the 3' Hydroxyl Blocking Groups

In some embodiments, the azidomethyl 3'hydroxyl protecting group may be removed or deprotected by using a water soluble phosphine reagent. Non-limiting examples include tris(hydroxymethyl)phosphine (THMP), tris(hydroxyethyl)phosphine (THEP) or tris(hydroxylpropyl)phosphine (THP or THPP). 3'-acetal blocking groups described herein may be removed or cleaved under various chemical conditions. For acetal blocking groups

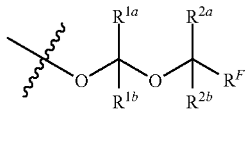

that contain a vinyl or alkenyl moiety, non-limiting cleaving condition includes a Pd(II) complex, such as $Pd(OAc)_2$ or allylPd(II) chloride dimer, in the presence of a phosphine ligand, for example tris(hydroxymethyl)phosphine (THMP), or tris(hydroxylpropyl)phosphine (THP or THPP). For those blocking groups containing an alkynyl group (e.g., an ethynyl), they may also be removed by a Pd(II) complex (e.g., $Pd(OAc)_2$ or allyl Pd(II) chloride dimer) in the presence of a phosphine ligand (e.g., THP or THMP).

Palladium Cleavage Reagents

In some embodiments, the 3' hydroxyl blocking group described herein may be cleaved by a palladium catalyst. In some such embodiments, the Pd catalyst is water soluble. In some such embodiments, is a Pd(0) complex (e.g., Tris(3,3',3"-phosphinidynetris(benzenesulfonato)palladium(0) nonasodium salt nonahydrate). In some instances, the Pd(0) complex may be generated in situ from reduction of a Pd(II) complex by reagents such as alkenes, alcohols, amines, phosphines, or metal hydrides. Suitable palladium sources include $Na_2PdCl_4$, $Pd(CH_3CN)_2Cl_2$, $(PdCl(C_3H_5))_2$, $[Pd(C_3H_5)(THP)]Cl$, $[Pd(C_3H_5)(THP)_2]Cl$, $Pd(OAc)_2$, $Pd(Ph_3)_4$, $Pd(dba)_2$, $Pd(Acac)_2$, $PdCl_2(COD)$, and $Pd(TFA)_2$. In one such embodiment, the Pd(0) complex is generated in situ from $Na_2PdCl_4$. In another embodiment, the palladium source is allyl palladium(II) chloride dimer $[(PdCl(C_3H_5))_2]$. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THMP), 1,3,5-triaza-7-phosphaadamantane (PTA), bis(ε-sulfonatophenyl)phenylphosphine dihydrate potassium salt, tris(carboxyethyl)phosphine (TCEP), and triphenylphosphine-3,3',3"-trisulfonic acid trisodium salt.

In some embodiments, the Pd(0) is prepared by mixing a Pd(II) complex $[(PdCl(C_3H_5))_2]$ with THP in situ. The molar ratio of the Pd(II) complex and the THP may be about 1:2, 1:3, 1:4, 1:5, 1:6, 1:7, 1:8, 1:9, or 1:10. In some further embodiments, one or more reducing agents may be added, such as ascorbic acid or a salt thereof (e.g., sodium ascorbate). In some embodiments, the cleavage mixture may contain additional buffer reagents, such as a primary amine, a secondary amine, a tertiary amine, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, 2-dimethylethanolamine (DMEA), 2-diethylethanolamine (DEEA), N,N,N',N'-tetramethylethylenediamine (TEMED), or N,N,N',N'-tetraethylethylenediamine (TEEDA), or combinations thereof. In one embodiment, the buffer reagent is DEEA. In another embodiment, the buffer reagent contains one or more inorganic salts such as a carbonate salt, a phosphate salt, or a borate salt, or combinations thereof. In one embodiment, the inorganic salt is a sodium salt.

Linkers

The dye compounds as disclosed herein may include a reactive linker group at one of the substituent positions for covalent attachment of the compound to a substrate or another molecule. Reactive linking groups are moieties capable of forming a bond (e.g., a covalent or non-covalent bond), in particular a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

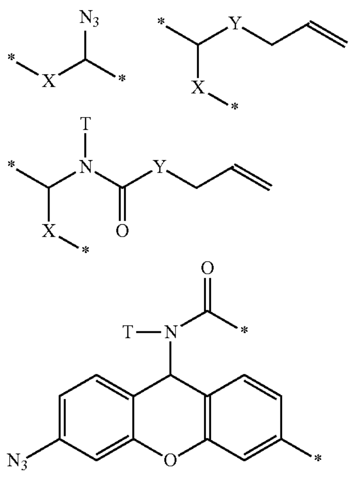

(wherein X is selected from the group comprising O, S, NH and NQ wherein Q is a C1-10 substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspect, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

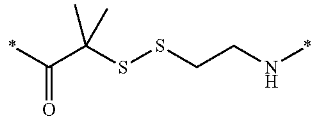

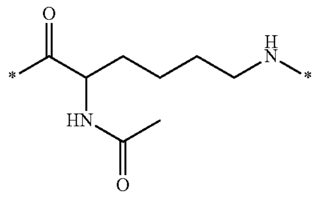

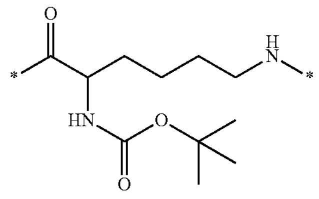

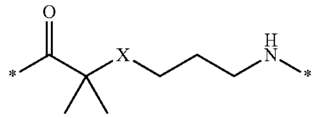

$X = CH_2, O, S$

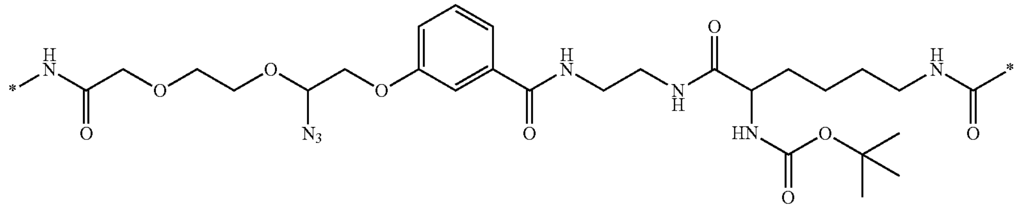

(wherein * indicates where the moiety is connected to the remainder of the nucleotide or nucleoside). The linker moieties illustrated herein may comprise the whole or partial linker structure between the nucleotides/nucleosides and the labels. The linker moieties illustrated herein may comprise the whole or partial linker structure between the nucleotides/nucleosides and the labels.

Additional examples of linkers include moieties of the formula:

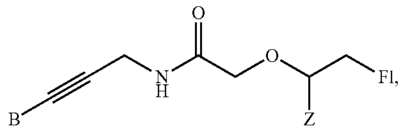

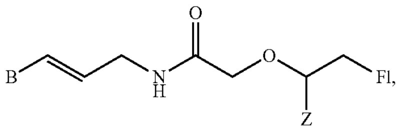

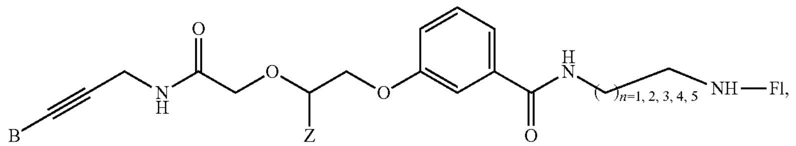

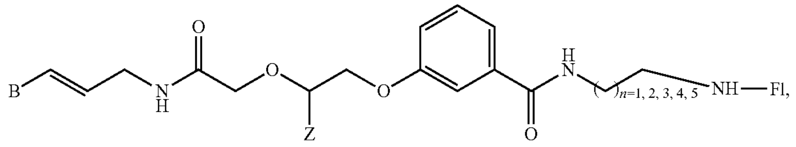

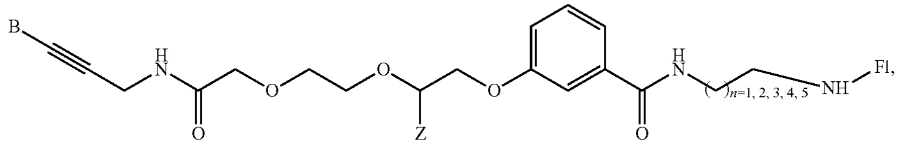

or

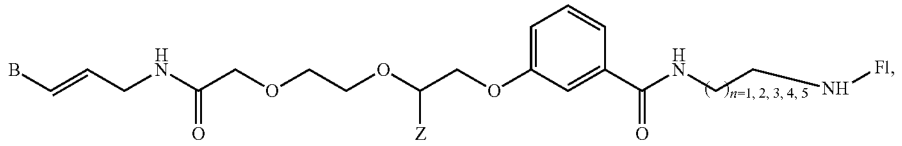

wherein B is a nucleobase; Z is —$N_3$ (azido), —O—$C_1$-$C_6$ alkyl, —O—$C_2$-$C_6$ alkenyl, or —O—$C_2$-$C_6$ alkynyl; and Fl comprises a dye moiety, which may contain additional linker structure. One of ordinary skill in the art understands that the dye compound described herein is covalently bounded to the linker by reacting a functional group of the dye compound (e.g., carboxyl) with a functional group of the linker (e.g., amino). In one embodiment, the cleavable linker comprises

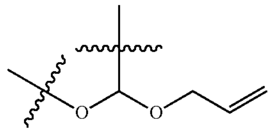 [SMILES: *OC(*)OCC=C]

("AOL" linker moiety) where Z is —O-allyl.

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula $-((CH_2)_2O)_n-$, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleotide or oligonucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the dyes described herein may have the formula:

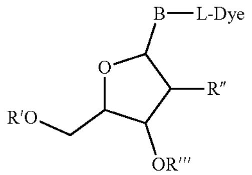

where Dye is a chromenoquinoline dye compound (label) moiety described herein (after covalent bonding between a functional group of the dye and a functional group of the linker "L"); B is a nucleobase, such as, for example uracil, thymine, cytosine, adenine, 7-deaza adenine, guanine, 7-deaza guanine, and the like; L is an optional linker which may or may not be present; R' can be H, or —OR' is monophosphate, diphosphate, triphosphate, thiophosphate, a phosphate ester analog, —O— attached to a reactive phosphorous containing group, or —O— protected by a blocking group; R" is H or OH; and R'" is H, a 3' OH blocking group described herein, or —OR'" forms a phosphoramidite. Where —OR'" is phosphoramidite, R' is an acid-cleavable hydroxyl protecting group which allows subsequent monomer coupling under automated synthesis conditions. In some further embodiments, B comprises

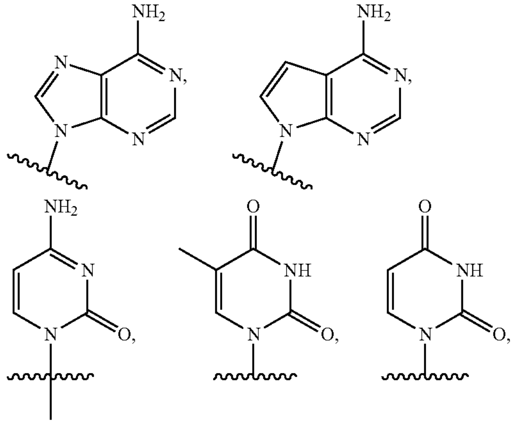

-continued

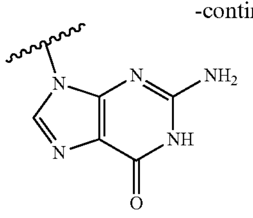

or

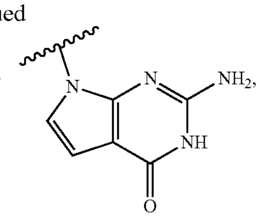

or optionally substituted derivatives and analogs thereof. In some further embodiments, the labeled nucleobase comprises the structure

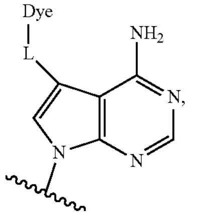

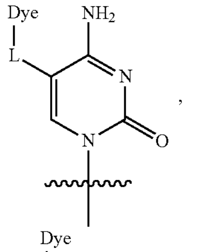

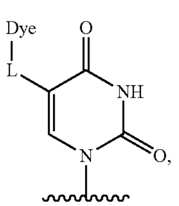

or

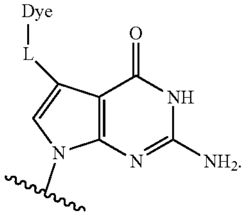

In a particular embodiment, the blocking group is separate and independent of the dye compound, i.e., not attached to it. Alternatively, the dye may comprise all or part of the 3'-OH blocking group. Thus R''' can be a 3' OH blocking group which may or may not comprise the dye compound.

In yet another alternative embodiment, there is no blocking group on the 3' carbon of the pentose sugar and the dye (or dye and linker construct) attached to the base, for example, can be of a size or structure sufficient to act as a block to the incorporation of a further nucleotide. Thus, the block can be due to steric hindrance or can be due to a combination of size, charge and structure, whether or not the dye is attached to the 3' position of the sugar.

In still yet another alternative embodiment, the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a labeled nucleotide is incorporated. If the blocking effect is reversible, for example, by way of non-limiting example by changing chemical conditions or by removal of a chemical block, extension can be stopped at certain points and then allowed to continue.

In a particular embodiment, the linker (between dye and nucleotide) and blocking group are both present and are separate moieties. In particular embodiments, the linker and blocking group are both cleavable under the same or substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

A

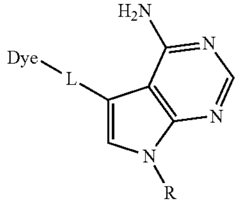

C

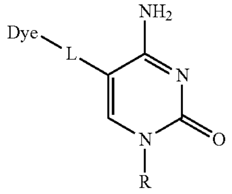

T

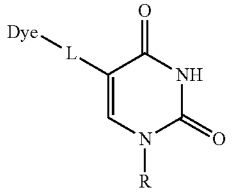

G

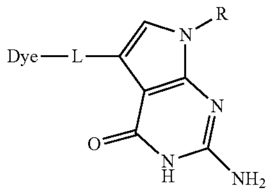

A

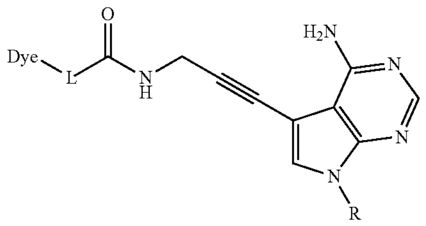

-continued
C
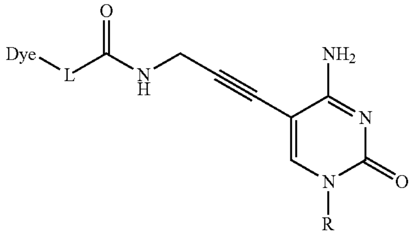
T
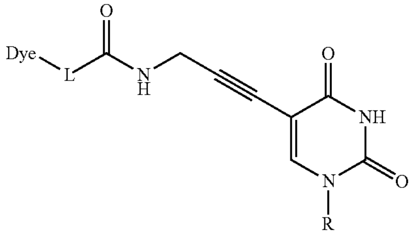
G
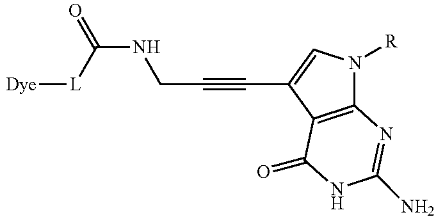
A
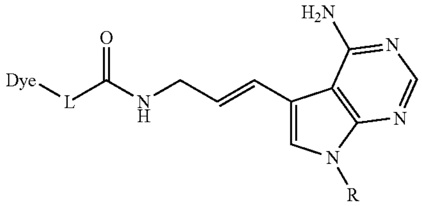
-continued
C
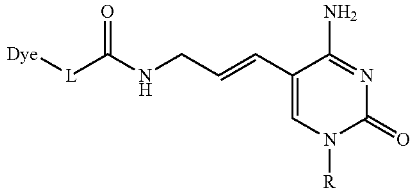
T
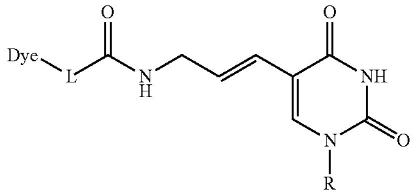
G
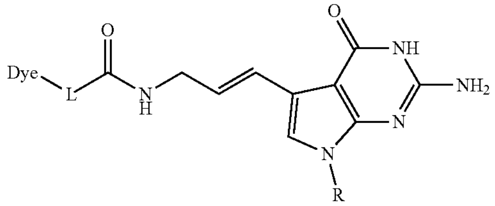
wherein L represents a linker and R represents a ribose or deoxyribose moiety as described above, or a ribose or deoxyribose moiety with the 5' position substituted with mono-, di- or triphosphates.
In some embodiments, non-limiting exemplary fluorescent dye conjugates are shown below:
ffA-LN3-Dye
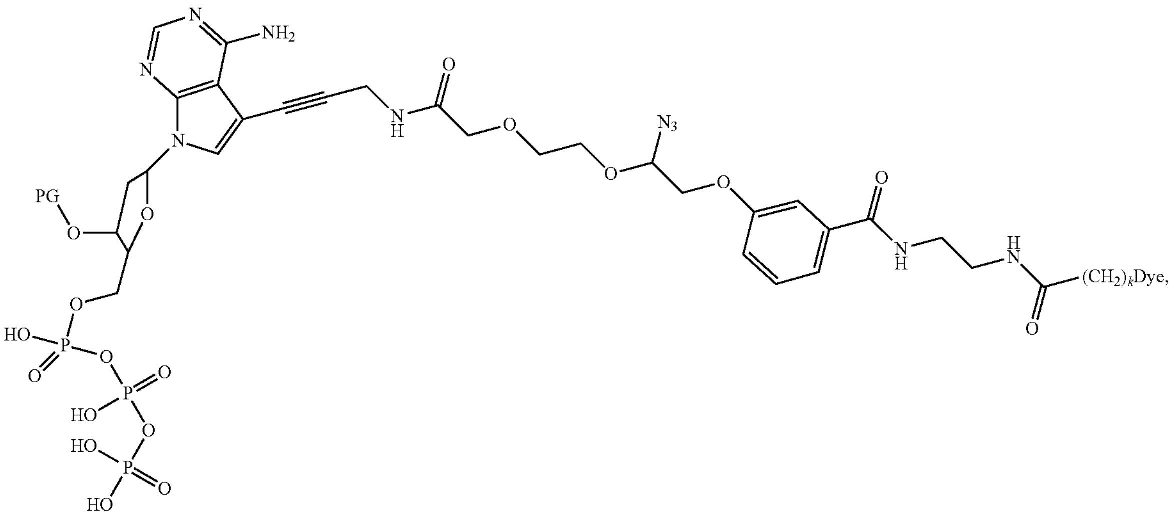

-continued
ffC-LN3-Dye
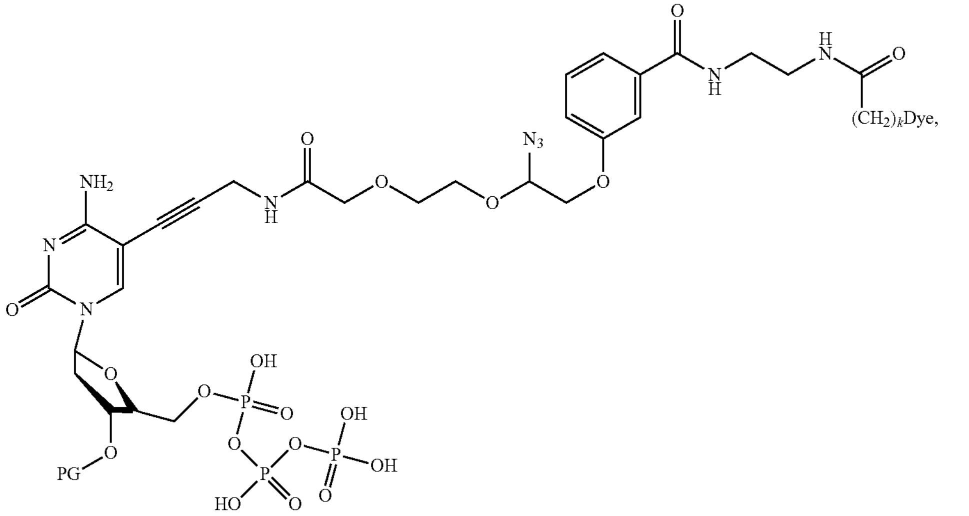
ffA-sPA-LN3-Dye
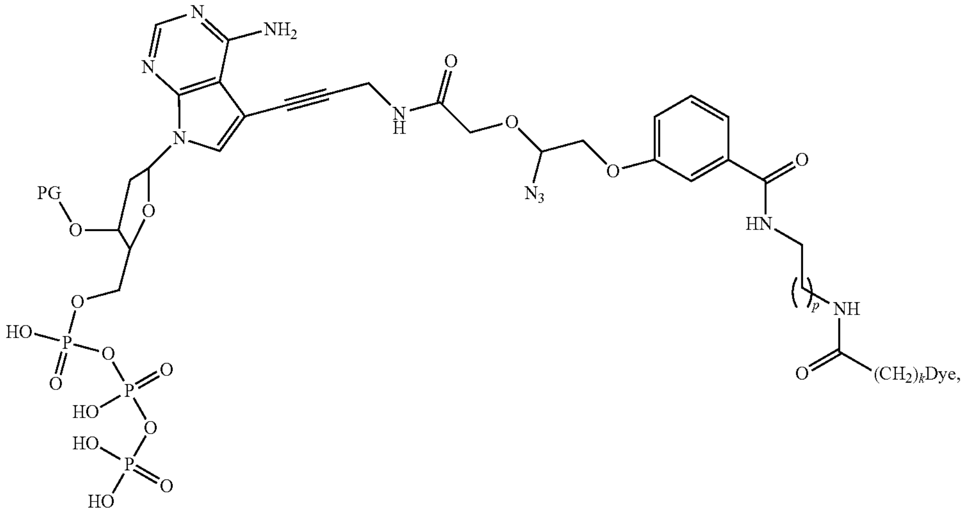
ffC-sPA-LN3-Dye
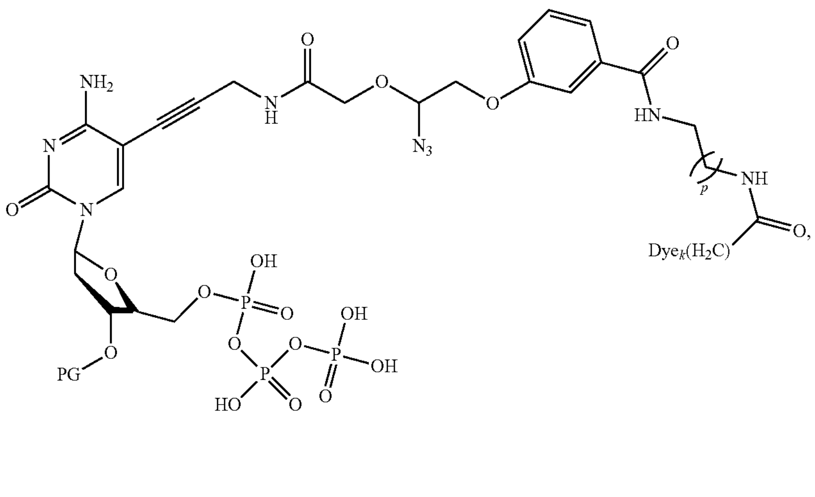

-continued
ffA-AOL-Dye
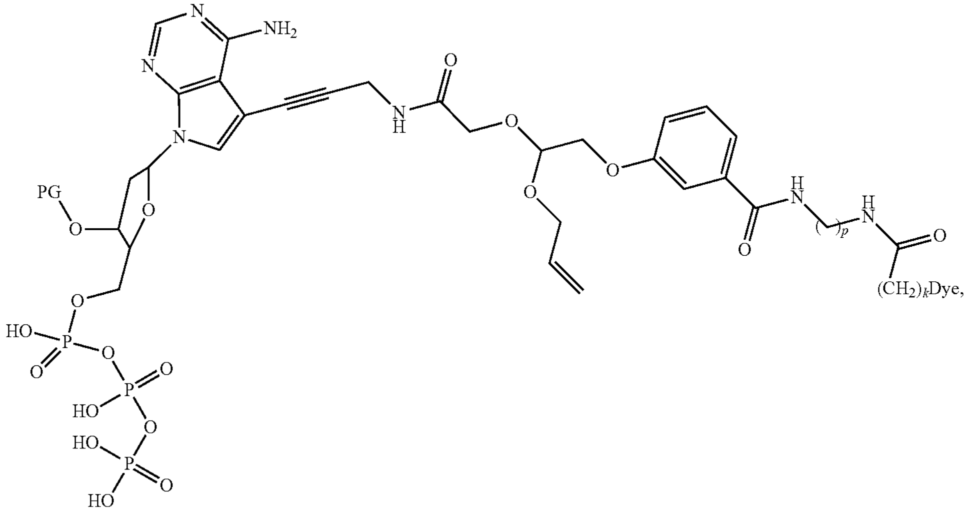
ffA-AOL-BL-Dye
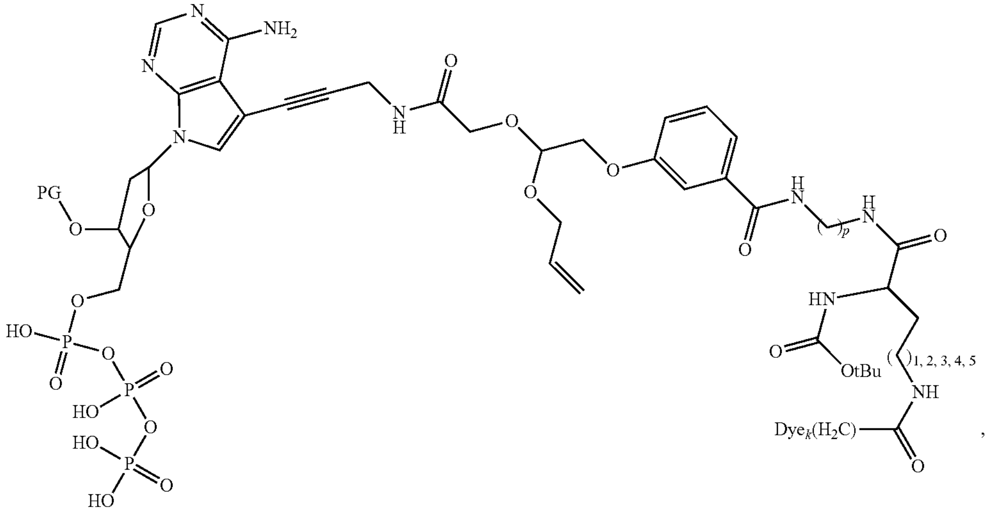
ffT-DB-AOL-Dye
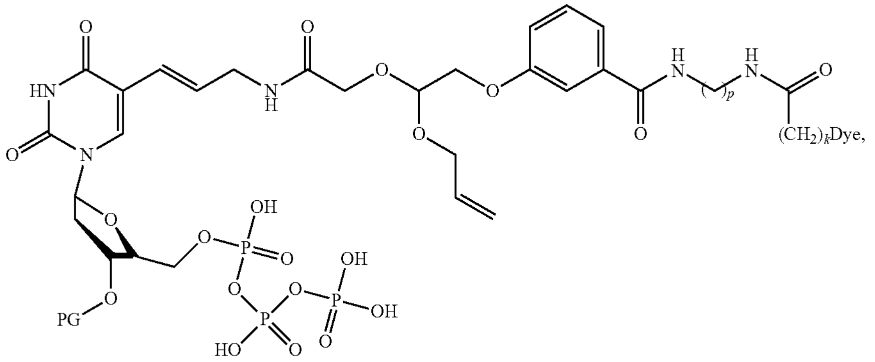

-continued ffC-AOL-Dye

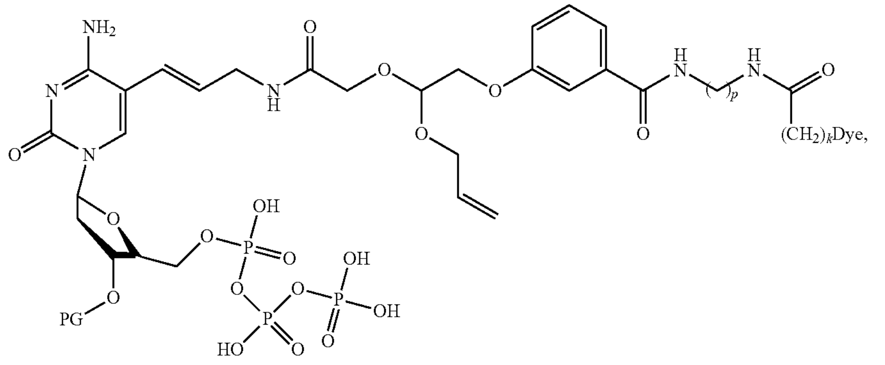

ffC-LN3-Dye

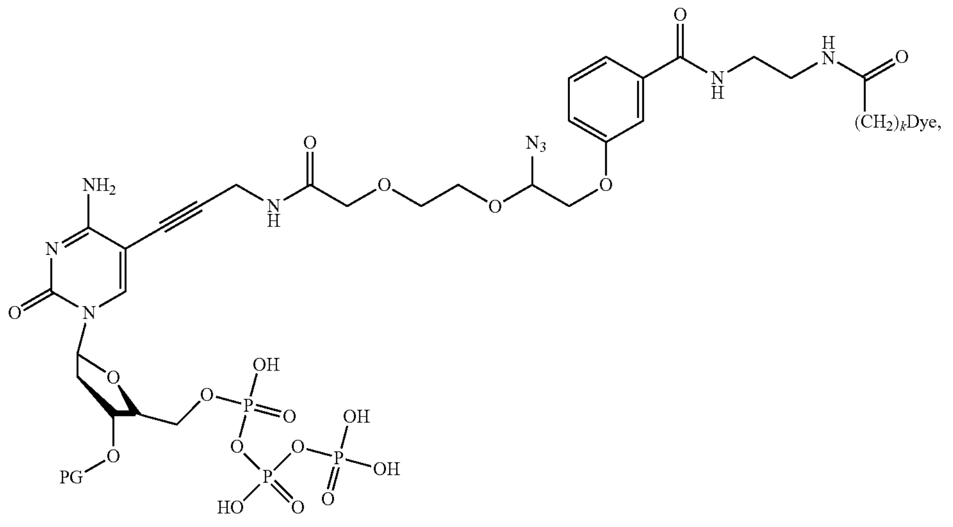

wherein PG stands for the 3' OH blocking groups described herein; p is an integer of 1, 2, 3, 4, 5, 6, 7, 8, 9, or 10; and k is 0, 1, 2, 3, 4, or 5. In one embodiment, —O—PG is AOM. In another embodiment, —O—PG is —O-azidomethyl. In one embodiment, k is 5. In some further embodiments, p is 1, 2 or 3; and k is 5.

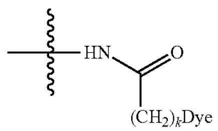

refers to the connection point of the Dye with the cleavable linker as a result of a reaction between an amino group of the linker moiety and the carboxyl group of the Dye. In any embodiments of the labeled nucleotide described herein, the nucleotide is a nucleotide triphosphate.

Additional aspects of the present disclosure relate to an oligonucleotide comprising a labeled nucleotide described herein. In some embodiments, the oligonucleotide is hybridized to at least a portion of a target polynucleotide. In some embodiments, the target polynucleotide is immobilized on a solid support. In some further embodiments, the solid support comprises an array of a plurality of immobilized target polynucleotides. In further embodiments, the solid support comprises a patterned flow cell. In further embodiments, the patterned flow cell is fabricated over a CMOS chip. In further embodiments, the patterned flow cell comprises a plurality of nanowells. In still further embodiments, the plurality of nanowells are aligned directly over each CMOS photodiode (pixel).

Kits

Provided herein are kits including a first nucleotide labeled with a chromenoquinoline compound of the present disclosure (i.e., a first label). In some embodiments, the kit also comprises a second labeled nucleotide, which is labeled with a second compound that is different than the chromenoquinoline in the first labeled nucleotide (i.e., a second label). In some embodiments, the first and second labeled nucleotides are excitable using a single excitation source, which may be a first light source having a first excitation wavelength. For example, the excitation bands for the first and the second labels may be at least partially overlapping such that excitation in the overlap region of the spectrum causes both labels to emit fluorescence. In some further embodiments, the kit may include a third nucleotide, wherein the third nucleotide is labeled with a third compound that is different from the first and the second labels (i.e., a third label). In some such embodiments, the first and third labeled nucleotides are excitable using a second excitation source, which may be a second light source having a second excitation wavelength that is different from the first excitation wavelength. For example, the excitation bands for the first and the third labels may be at least partially overlapping such that excitation in the overlap region of the spectrum causes both labels to emit fluorescence. In some further embodiments, the kit may further comprise a fourth nucleotide. In some such embodiments, the fourth nucleotide is unlabeled (dark). In other embodiments, the fourth nucleotide is labeled with a different compound than the first, second and the third nucleotide, and each label has a distinct absorbance maximum that is distinguishable from the other labels. In still other embodiments, the fourth nucleotide is unlabeled. In some embodiments, the first excitation light source has a wavelength from about 500 nm to about 550 nm, from about 510 to about 540 nm, or from about 520 to about 530 nm (e.g., 520 nm). The second light source has an excitation wavelength from about 400 nm to about 480 nm, from about 420 nm to about 470 nm, or from 450 nm to about 460 nm (e.g., 450 nm). In alternative embodiments, the first light source has an excitation wavelength from about 400 nm to about 480 nm, from about 420 nm to about 470 nm, or from 450 nm to about 460 nm (e.g., 450 nm). The second excitation light source has a wavelength from about 500 nm to about 550 nm, from about 510 to about 540 nm, or from about 520 to about 530 nm (e.g., 520 nm). The second light source has an excitation wavelength from about 400 nm to about 480 nm, from about 420 nm to about 470 nm, or from 450 nm to about 460 nm (e.g., 450 nm). In further embodiments, each of the first label, the second label, and the third label has an emission spectrum that can be collected in a single emission collection filter or channel.

In some embodiments, the kit may contain four labeled nucleotides (A, C, G and T or U), where the first of the four nucleotides is labeled with a compound as disclosed herein. In such a kit, each of the four nucleotides can be labeled with a compound that is the same or different from the label on the other three nucleotides. Alternatively, a first of the four nucleotides is a labeled nucleotide describe herein, a second of the four nucleotides carries a second label, a third nucleotide carries a third label, and a fourth nucleotide is unlabeled (dark). As another example, a first of the four nucleotides is a labeled nucleotide described herein, a second of the four nucleotides carries a second label, a third nucleotide carries a mixture of two labels, and a fourth nucleotide is unlabeled (dark). Thus, one or more of the label compounds can have a distinct absorbance maximum and/or emission maximum such that the compound(s) is(are) distinguishable from other compounds. For example, each compound can have a distinct absorbance maximum and/or emission maximum such that each of the compounds is spectrally distinguishable from the other three compounds (or two compounds if the fourth nucleotide is unlabeled). It will be understood that parts of the absorbance spectrum and/or emission spectrum other than the maxima can differ and these differences can be exploited to distinguish the compounds. The kit may be such that two or more of the compounds have a distinct absorbance maximum. The chromenoquinoline dyes described herein typically absorb light in the region below 500 nm. For example, these chromenoquinoline dyes may have an absorption wavelength of from about 450 nm to about 530 nm, from about 460 nm to about 520 nm, from about 475 nm to about 510 nm, or from about 490 nm to about 500 nm.

The compounds, nucleotides, or kits that are set forth herein may be used to detect, measure, or identify a biological system (including, for example, processes or components thereof). Exemplary techniques that can employ the compounds, nucleotides or kits include sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain two light sources operating at different wavelengths.

In a particular embodiment, the labeled nucleotide(s) described herein may be supplied in combination with unlabeled or native nucleotides, or any combination thereof. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, nucleotides, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two nucleotides labeled with fluorescent dye compounds are supplied in kit form, it is a feature of some embodiments that the spectrally distinguishable fluorescent dyes can be excited at the same wavelength, such as, for example by the same light source. When four nucleotides labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths for the dyes are between 450-460 nm, 490-500 nm, or 520 nm or above (e.g., 532 nm).

In some embodiments, a kit includes a first nucleotide labeled with a chromenoquinoline dye of the present disclosure and a second nucleotide labeled with a second dye wherein the dyes have a difference in absorbance maximum of at least 10 nm, particularly 20 nm to 50 nm, or 30 nm to 40 nm. More particularly, the first label may have a Stokes shift of above 50 nm above 60 nm, above 70 nm, or above 80 nm. The second label may have a Stokes shift of about 80 nm, above 90 nm or above 100 nm (where "Stokes shift" is the distance between the peak absorption and peak emission wavelengths). Furthermore, the first label may have an absorption maximum from about 460 nm to about 520 nm, from about 475 nm to about 510 nm, or from about 490 nm to about 500 nm. The second label may have an absorption maximum from about 400 nm to about 470 nm, or from about 450 nm to about 460 nm. In a further embodiment, a kit can further a third labeled nucleotide where the third label has an absorption maximum of above 520 nm. The third label may have a Stokes shift of above 20 nm, above 30 nm or above 40 nm, or a Stokes shift of between 20-40 nm. The kit may further include a fourth nucleotide which is not labeled. In further embodiments, each of the first label, the second label, and the third label has an emission maximum over greater than 540 nm, greater than 550 nm, greater than 560 nm, greater than 570 nm, greater than 580 nm, greater than 590 nm, or greater than 600 nm. In some embodiments, the emission spectra of the first label, the second label and the third label may be detected or collected in a single emission collection channel or filter (e.g., a collection region from about 580 to about 700 nm).

In an alternative embodiment, the kits of the disclosure may contain nucleotides where the same base is labeled with two different compounds. A first nucleotide may be labeled with a compound of the disclosure. A second nucleotide may be labeled with a spectrally distinct compound, for example a 'green' dye absorbing at less than 600 nm. A third nucleotide may be labeled as a mixture of the compound of the disclosure and the spectrally distinct compound, and the fourth nucleotide may be 'dark' and contain no label. In simple terms, therefore, the nucleotides 1-4 may be labeled 'blue', 'green', 'blue/green', and dark. To simplify the instrumentation further, four nucleotides can be labeled with two dyes excited with a single light source, and thus the labeling of nucleotides 1-4 may be 'blue 1', 'blue 2', 'blue 1/blue 2', and dark.

Although kits are exemplified herein in regard to configurations having different nucleotides that are labeled with different dye compounds, it will be understood that kits can include 2, 3, 4 or more different nucleotides that have the same dye compound.

In addition to the labeled nucleotides, the kit may comprise together at least one additional component. The further component(s) may be one or more of the components identified in a method set forth herein or in the Examples section below. Some non-limiting examples of components that can be combined into a kit of the present disclosure are set forth below. In some embodiments, the kit further comprises a DNA polymerase (such as a mutant DNA polymerase) and one or more buffer compositions. One buffer composition may comprise antioxidants such as ascorbic acid or sodium ascorbate, which can be used to protect the dye compounds from photo damage during detection. Additional buffer composition may comprise a reagent can may be used to cleave the 3' blocking group and/or the cleavable linker. For example, a water-soluble phosphines or water-soluble transition metal catalysts formed from a transition metal and at least partially water-soluble ligands, such as a palladium complex. Various components of the kit may be provided in a concentrated form to be diluted prior to use. In such embodiments a suitable dilution buffer may also be included. Again, one or more of the components identified in a method set forth herein can be included in a kit of the present disclosure. In any embodiments of the nucleotide or labeled nucleotide described herein, the nucleotide contains a 3' hydroxyl blocking group.

Methods of Sequencing

Nucleotides comprising a dye compound according to the present disclosure may be used in any method of analysis such as method that include detection of a fluorescent label attached to such nucleotide, whether on its own or incorporated into or associated with a larger molecular structure or conjugate. In this context the term "incorporated into a polynucleotide" can mean that the 5' phosphate is joined in phosphodiester linkage to the 3' hydroxyl group of a second nucleotide, which may itself form part of a longer polynucleotide chain. The 3' end of a nucleotide set forth herein may or may not be joined in phosphodiester linkage to the 5' phosphate of a further nucleotide. Thus, in one non-limiting embodiment, the disclosure provides a method of detecting a labeled nucleotide incorporated into a polynucleotide which comprises: (a) incorporating at least one labeled nucleotide of the disclosure into a polynucleotide and (b) determining the identity of the nucleotide(s) incorporated into the polynucleotide by detecting the fluorescent signal from the dye compound attached to said nucleotide(s).

This method can include: a synthetic step (a) in which one or more labeled nucleotides according to the disclosure are incorporated into a polynucleotide and a detection step (b) in which one or more labeled nucleotide(s) incorporated into the polynucleotide are detected by detecting or quantitatively measuring their fluorescence.

Some embodiments of the present application are directed to a method of determining the sequence of a target polynucleotide (e.g., a single-stranded target polynucleotide), comprising: (a) contacting a primer polynucleotide with one or more labeled nucleotides (such as nucleoside triphosphates A, G, C and T), wherein at least one of said labeled nucleotide is a labeled nucleotide described herein, and wherein the primer polynucleotide is complementary to at least a portion of the target polynucleotide; (b) incorporating a labeled nucleotide into the primer polynucleotide; and (c) performing one or more fluorescent measurements to determine the identify of the incorporated nucleotide. In some such embodiments, the primer polynucleotide/target polynucleotide complex is formed by contacting the target polynucleotide with a primer polynucleotide complementary to at least a portion of the target polynucleotide. In some embodiments, the method further comprises (d) removing the label moiety and the 3' hydroxyl blocking group from the nucleotide incorporated into the primer polynucleotide. In some further embodiments, the method may also comprises (e) washing the removed label moiety and the 3' blocking group away from the primer polynucleotide strand. In some embodiments, steps (a) through (d) or steps (a) through (e) are repeated until a sequence of at least a portion of the target polynucleotide strand is determined. In some instances, steps (a) through (d) or steps (a) through (e) are repeated at least at least 30, 40, 50, 60, 70, 80, 90, 100, 110, 120, 130, 140, 150, 160, 170, 180, 190, 200, 250, or 300 cycles. In some embodiments, the label moiety and the 3' blocking group from the nucleotide incorporated into the primer polynucleotide strand are removed in a single chemical reaction. In some further embodiments, the method is performed on an automated sequencing instrument, and wherein the automated sequencing instrument comprises two light sources operating at different wavelengths. In some embodiments, the sequence determination is conducted after the completion of repeated cycles of the sequencing steps described herein.

Some embodiments of the present disclosure relate to a method for determining the sequence of a target polynucleotide (e.g., a single stranded target polynucleotide), comprising: (a) contacting a primer polynucleotide with an incorporation mixture comprising one or more of four different types of nucleotide conjugates, wherein a first type of nucleotide conjugate comprises a first label, a second type of nucleotide conjugate comprises a second label, and a third type of nucleotide conjugate comprises a third label, wherein each of the first label, the second label, and the third label is spectrally distinct from one another, and wherein the primer polynucleotide is complementary to at least a portion of the target polynucleotide; (b) incorporating one nucleotide conjugate from the mixture to the primer polynucleotide to produce an extended primer polynucleotide; (c) performing a first imaging event using a first excitation light source and detecting a first emission signal from the extended polynucleotide; and (d) performing a second imaging event using a second excitation light source and detecting a second emission signal from the extended polynucleotide; wherein the first excitation light source and the second excitation light source have different wavelengths; and wherein first emission signal and the second emission signal are detected or collected in a single emission detection channel. In some embodiments, the chromenoquinoline dyes described herein may be used as any one of the first, the second or the third label described in the method. In some embodiments, the method does not comprise a chemical modification of any nucleotide conjugates in the mixture after the first imaging event and prior to the second imaging event. In some further embodiments, the incorporation mixture further comprises a fourth type of nucleotide, wherein the fourth type of nucleotide is unlabeled of is labeled with a fluorescent moiety that does not emit a signal from either the first or the second imaging event. In this sequencing method, the identity of each incorporated nucleotide conjugate is determined based on the detection patterns of the first imaging event and the second imaging event. For example, the incorporation of the first type of the nucleotide conjugate is determined by a signal state in the first imaging event and a dark state in the second imaging event. The incorporation of the second type of the nucleotide conjugates is determined by a dark state in the first imaging event and a signal state in the second imaging event. The incorporation of the third type of the nucleotide conjugates is determined by a signal state in both the first imaging event and the second imaging event. The incorporation of the fourth type of the nucleotide conjugates is determined by a dark state in both the first imaging event and the second imaging event. In further embodiments, steps (a) through (d) are performed in repeated cycles (e.g., at least 30, 50, 100, 150, 200, 250, 300, 400, or 500 times) and the method further comprises sequentially determining the sequence of at least a portion of the single-stranded target polynucleotide based on the identity of each sequentially incorporated nucleotide conjugates. In some embodiments, the first excitation light source has a shorter wavelength than the second excitation light source. In some such embodiments, the first excitation light source has a wavelength of about 400 nm to about 480 nm, about 420 nm to about 470 nm, or about 450 nm to about 460 nm (i.e., "blue light"). In one embodiment, the first excitation light source has a wavelength of about 450 nm. The second excitation light source has a wavelength of about 500 nm to about 550 nm, about 510 nm to about 540 nm, or about 520 nm to about 530 nm (i.e., "green light"). In one embodiment, the second excitation light source has a wavelength of about 520 nm. In other embodiments, the first excitation light source has a longer wavelength than the second excitation light source. In some such embodiments, the first excitation light source has a wavelength of about 500 nm to about 550 nm, about 510 nm to about 540 nm, or about 520 nm to about 530 nm (i.e., "green light"). In one embodiment, the second excitation light source has a wavelength of about 520 nm. The second excitation light source has a wavelength of about 400 nm to about 480 nm, about 420 nm to about 470 nm, or about 450 nm to about 460 nm (i.e., "blue light"). In one embodiment, the second excitation light source has a wavelength of about 450 nm.

In some embodiments, at least one nucleotide is incorporated into a polynucleotide (such as a single stranded primer polynucleotide described herein) in the synthetic step by the action of a polymerase enzyme. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template or target polynucleotide strand with a reaction mixture comprising fluorescently labeled nucleotides of the disclosure. A polymerase can also be provided under conditions which permit formation of a phosphodiester linkage between a free 3' hydroxyl group on a polynucleotide strand annealed to the template or target polynucleotide strand and a 5' phosphate group on the labeled nucleotide. Thus, a synthetic step can include formation of a polynucleotide strand as directed by complementary base pairing of nucleotides to a template/target strand.

In all embodiments of the methods, the detection step may be carried out while the polynucleotide strand into which the labeled nucleotides are incorporated is annealed to a template/target strand, or after a denaturation step in which the two strands are separated. Further steps, for example chemical or enzymatic reaction steps or purification steps, may be included between the synthetic step and the detection step. In particular, the polynucleotide strand incorporating the labeled nucleotide(s) may be isolated or purified and then processed further or used in a subsequent analysis. By way of example, polynucleotide strand incorporating the labeled nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including the labeled nucleotides as described herein, to form an extended polynucleotide strand (primer polynucleotide strand) complementary to the template/target strand in the presence of a suitable polymerase enzyme. In other embodiments, the synthetic step may itself form part of an amplification reaction producing a labeled double stranded amplification product comprised of annealed complementary strands derived from copying of the primer and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of the labeled nucleotides as set forth herein. A variety of naturally occurring or mutant/modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the labeled nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the modified nucleotide or nucleoside labeled with dyes set forth herein when incorporated into a polynucleotide.

A particular embodiment of the disclosure provides use of labeled nucleotides comprising dye moiety according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template/target nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the nucleotides labeled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template/target polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template/target polynucleotide, and the blocking group prevents further incorporation of nucleotides. Any unincorporated nucleotides can be washed away and the fluorescent signal from each incorporated nucleotide can be "read" optically by suitable means, such as a charge-coupled device using light source excitation and suitable emission filters. The 3' blocking group and fluorescent dye compounds can then be removed (deprotected) (simultaneously or sequentially) to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group that serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxyl group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to a support (for example, silica-based supports such as those disclosed in WO00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature, 437, 376-380 (2005); Science, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Nucleotides labeled with dye compounds of the present disclosure may be used for sequencing templates on essentially any type of array, including but not limited to those formed by immobilization of nucleic acid molecules on a solid support.

However, nucleotides labeled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using nucleotides labeled with dye compounds of the disclosure.

Nucleotides labeled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO00/06770 and WO 01/57248, each of which is incorporated herein by reference. Although one use of the labeled nucleotides of the disclosure is in sequencing-by-synthesis reactions, the utility of the such nucleotides is not limited to such methods. In fact, the labeled nucleotides described herein may be used advantageously in any sequencing methodology which requires detection of fluorescent labels attached to nucleotides incorporated into a polynucleotide.

In particular, nucleotides labeled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses nucleotides labeled with dye compounds which are dideoxynucleotides lacking hydroxyl groups at both of the 3' and 2' positions, such modified dideoxynucleotides being suitable for use in Sanger type sequencing methods and the like.

Nucleotides labeled with dye compounds of the present disclosure incorporating 3' blocking groups, it will be recognized, may also be of utility in Sanger methods and related protocols since the same effect achieved by using dideoxy nucleotides may be achieved by using nucleotides having 3' OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

Alternatively, the sequencing methods described herein may also be carried out using unlabeled nucleotides and affinity reagents containing a fluorescent dye described herein. For example, one, two, three or each of the four different types of nucleotides (e.g., dATP, dCTP, dGTP and dTTP or dUTP) in the incorporation mixture of step (a) may be unlabeled. Each of the four types of nucleotides (e.g., dNTPs) has a 3' hydroxyl blocking group to ensure that only a single base can be added by a polymerase to the 3' end of the primer polynucleotide. After incorporation of an unlabeled nucleotide in step (b), the remaining unincorporated nucleotides are washed away. An affinity reagent is then introduced that specifically recognizes and binds to the incorporated dNTP to provide a labeled extension product comprising the incorporated dNTP. Uses of unlabeled nucleotides and affinity reagents in sequencing by synthesis have been disclosed in WO 2018/129214 and WO 2020/097607. A modified sequencing method of the present disclosure using unlabeled nucleotides may include the following steps:

(a') contacting a primer polynucleotide/target polynucleotide complex with one or more unlabeled nucleotides (e.g., dATP, dCTP, dGTP, and dTTP or dUTP), wherein the primer polynucleotide is complementary to at least a portion of the target polynucleotide;

(b') incorporating a nucleotide into the primer polynucleotide to produce an extended primer polynucleotide;

(c') contacting the extended primer polynucleotide with a set of affinity reagents under conditions wherein one affinity reagent binds specifically to the incorporated unlabeled nucleotide to provide a labeled extended primer polynucleotide/target polynucleotide complex;

(d') performing one or more fluorescent measurements of the labeled extended primer polynucleotide/target polynucleotide complex to determine the identity of the incorporated nucleotide.

In some embodiments of the modified sequencing method described herein, each of the unlabeled nucleotides in the incorporation mixture contains a 3' hydroxyl blocking group. In further embodiments, the 3' hydroxyl blocking group of the incorporated nucleotide is removed prior to the next incorporation cycle. In still further embodiments, the method further comprises removing the affinity reagent from the incorporated nucleotide. In still further embodiments, the 3' hydroxyl blocking group and the affinity reagent are removed in the same reaction. In some embodiments, the set of affinity reagents may comprise a first affinity reagent that binds specifically to the first type of nucleotide, a second affinity reagent that binds specifically to the second type of nucleotide, and a third affinity reagent that binds specifically to the third type of nucleotide. In some further embodiments, each of the first, second and the third affinity reagents comprises a detectable labeled that is spectrally distinguishable. In some embodiments, the affinity reagents may include protein tags, antibodies (including but not limited to binding fragments of antibodies, single chain antibodies, bispecific antibodies, and the like), aptamers, knottins, affimers, or any other known agent that binds an incorporated nucleotide with a suitable specificity and affinity. In one embodiment, at least one affinity reagent is an antibody or a protein tag. In another embodiment, at least one of the first type, the second type, and the third type of affinity reagents is an antibody or a protein tag comprising one or more detectable labels (e.g., multiple copies of the same detectable label), wherein the detectable label is or comprises a chromenoquinoline dye moiety described herein.

EXAMPLES

Additional embodiments are disclosed in further detail in the following examples, which are not in any way intended to limit the scope of the claims.

Example 1. Synthesis of Chromenoquinoline Dyes

Synthesis of Chromenoquinoline Dye Intermediates

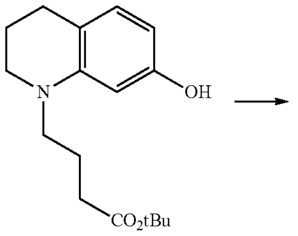

1

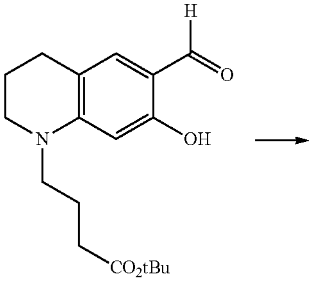

2

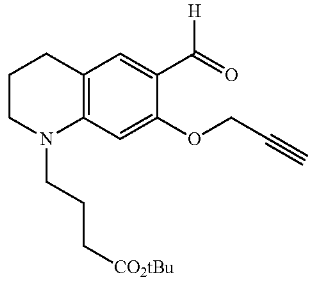

3

γ-(7-hydroxy-1,2,3,4-tetrahydroquinol-1-yl)butyric acid tert-butyl ester (1) (3.94 g, 13.5 mmol) was coevaporated with anhydrous N,N'-dimethylformamide (DMF) (3×10 mL). Phosphorus oxychloride (1.9 mL, 20 mmol) was added to 30 mL of anhydrous DMF at 0° C. After 15 minutes the solution turned pale pink and a solution on 1 in 10 mL of DMF was added. The reaction was stirred at RT for 3 hours, then quenched with 10 mL of sat. aq. $NaHCO_3$. After 5 minutes, the volatiles were removed under reduced pressure to leave a deep green oil. 300 mL of sat. aq. $NaHCO_3$ were added, and the solution was extracted with 5×200 mL of ethyl acetate. The pooled organic phases were dried over $MgSO_4$, filtered and evaporated to dryness under reduced pressure. The residue was purified by flash chromatography on silica gel to afford compound 2. Yield: 3.656 g, green oil (11.4 mmol, 84%). LC-MS (ES and CI): (positive ion) m/z 320 ($M+H^+$); (negative ion) m/z 318 ($M-H^+$).

γ-(6-formyl-7-hydroxy-1,2,3,4-tetrahydroquinol-1-yl)butyric acid tert-butyl ester (2) (2.46 g, 7.72 mmol) was dissolved in anhydrous DMF then $K_2CO_3$ (2.13 g, 15.4 mmol), tetrabutylammonium iodide (258 mg, 0.70 mmol) and propargyl bromide (80 wt. % in toluene, 1.28 mL, 11.6 mmol) were added. The reaction was stirred overnight at RT, then quenched with 150 mL of water, then extracted with 200 mL of ethyl acetate. The aqueous phase was separated and extracted with 2×100 mL of ethyl acetate. The combined organic phases were then extracted again with 2×100 mL of water. The organic phases were dried over $MgSO_4$, filtered and evaporated to dryness under reduced pressure. The residue was purified by flash chromatography on silica gel to afford compound 3. Yield: 2.01 g, yellow solid (5.65 mmol, 73%). LC-MS (ESI): (positive ion) m/z 358 ($M+H^+$), 380 ($M+Na^+$).

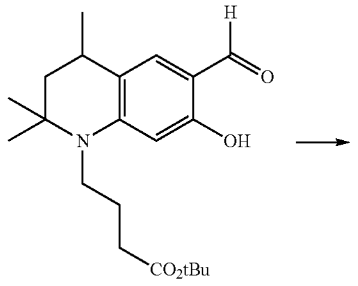

4

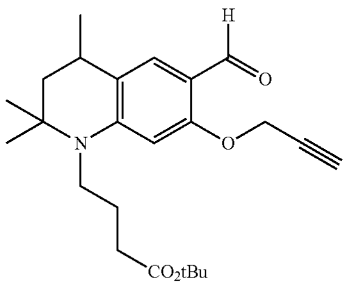

5

Compound 5 was synthesized from γ-(1-dimethyl-3-methyl-6-formyl-7-hydroxy-1,2,3,4-tetrahydroquinol-1-yl) butyric acid tert-butyl ester (4) as an off-white solid, according to the procedure described for compound 3. Yield: 351 mg (0.86 mmol, 86%). LC-MS (ES and CI): (positive ion) m/z 400 ($M+H^+$).

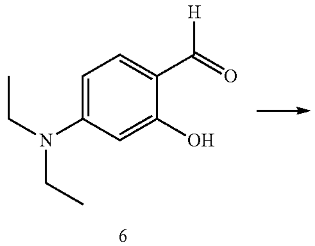

6

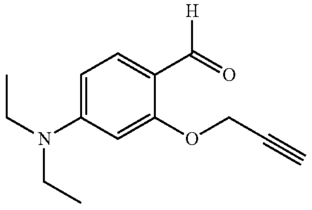

7

Compound 7 was synthesized from 4-(diethylamino)salicylaldehyde (6) as a pale pink solid, according to the procedure described for compound 3. Yield: 2.263 mg (9.97 mmol, 95%). LC-MS (ES and CI): (positive ion) m/z 232 ($M+H^+$).

General Synthesis of Chromenoquinoline Dyes

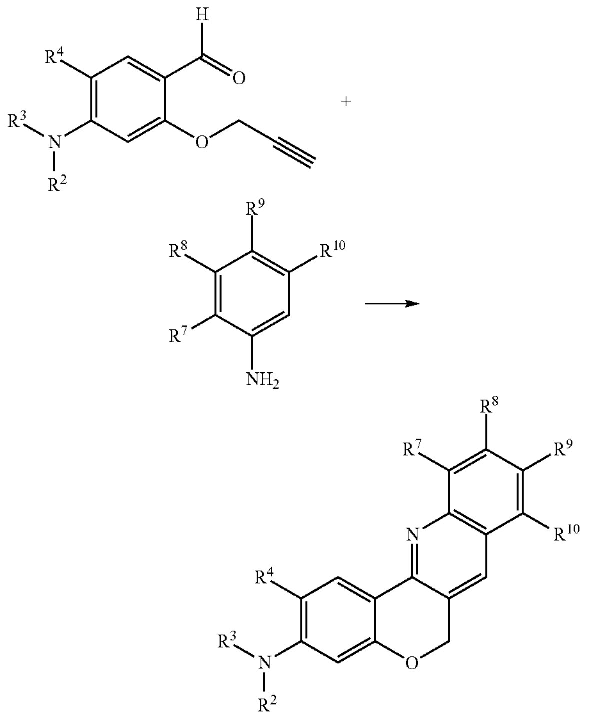

A substituted 4-amino-2-propargyloxy-benzaldehyde (0.336 mmol) and a substituted aniline (0.37 mmol) were dissolved in anhydrous DMF under $N_2$, then acetic acid (10 μL, 0.16 mmol) was added and the solution was heated to 60 C for 1 hour. TLC (petroleum ether/ethyl acetate 1:1) showed the formation of a yellow intermediate. Then, CuI (13 mg, 0.067 mmol) was added, and the reaction was stirred at 60-100° C. until completion. The reaction was diluted with 30 mL of ethyl acetate, filtered on a plug of silica gel, then purified by flash chromatography.

Compound 8a: Starting from intermediate 3 and p-anisidine, compound 8a was obtained in 31% yield, as a yellow solid. LC-MS (ESI): (positive ion) m/z 461 ($M+H^+$).

Compound 8b: Starting from intermediate 3 and 4-methylaniline, compound 8b was obtained in 35% yield, as a yellow solid (89 mg, 0.20 mmol). LC-MS (ESI): (positive ion) m/z 445 ($M+H^+$).

Compound 8c: Starting from intermediate 3 and 3,4-dimethylaniline, compound 8c was obtained as a 6:4 mixture of two regioisomers, in 21% yield, as a yellow solid (32 mg, 0.07 mmol). LC-MS (ESI): (positive ion) m/z 459 ($M+H^+$).

Compound 8d: Starting from intermediate 3 and 3,4-dimethoxyaniline, compound 8d was obtained in 48% yield, as a yellow solid (68 mg, 0.138 mmol). LC-MS (ESI): (positive ion) m/z 491 ($M+H^+$).

Compound 8e: Starting from intermediate 5 and p-anisidine, compound 8e was obtained in 40% yield, as a yellow solid (76 mg, 0.151 mmol). LC-MS (ESI): (positive ion) m/z 503 ($M+H^+$).

Compound 8f: Starting from intermediate 7 and methyl-(4-aminophenyl)-acetate, compound 8f was obtained in 39% yield, as a yellow solid (321 mg, 0.85 mmol). LC-MS (ESI): (positive ion) m/z 377 ($M+H^+$).

Compound 8g: Starting from intermediate 3 and 3,4-(methylenedioxy)aniline, compound 8g was obtained in 40% yield, as a yellow solid (65 mg, 0.137 mmol). LC-MS (ESI): (positive ion) m/z 475 ($M+H^+$).

Compound 8h: Starting from intermediate 3 and 3,4,5-trimethoxyaniline, compound 8h was obtained in 35% yield, as a yellow solid (65 mg, 0.117 mmol). LC-MS (ESI): (positive ion) m/z 521 ($M+H^+$).

Compound 8i: Starting from intermediate 3 and 5-amino-2,3-dihydrobenzofuran, compound 8i was obtained in 31% yield, as a yellow solid (50 mg, 0.117 mmol). LC-MS (ESI): (positive ion) m/z 473 ($M+H^+$).

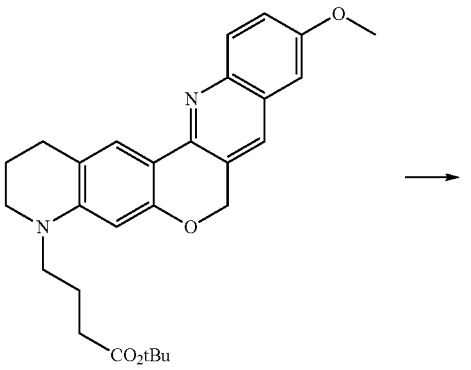

8a

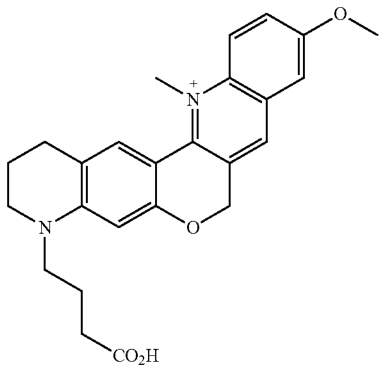

I-1

Compound 8a (82 mg, 0.178 mmol) was dissolved in dry 1,4-dioxane (2 mL) in a pressure tube. Iodomethane (0.5 mL, 8 mmol) was added, and the reaction was heated at 100° C. After 2 hours, it was cooled down, the volatiles were removed under reduced pressure and the crude was purified by flash column chromatography. The intermediate was then dissolved in dry DCM (1 mL) and 0.5 mL of trifluoroacetic acid were added and the reaction was stirred at RT for 1.5 hours. Then the volatiles were removed under reduced pressure and the crude was purified by flash column chromatography to afford compound I-1 as a red solid. Yield: 28 mg (0.067, 37%). $^1H$ NMR (400 MHz, MeOD): δ (ppm) 8.38 (s, 1H, Ar—CH), 7.64 (dd, J=9.5, 2.9 Hz, 1H, Ar—CH), 7.57 (s, 1H, Ar—CH), 7.51 (d, J=2.9 Hz, 1H, Ar—CH), 6.52 (s, 1H, Ar—CH), 5.18 (s, 2H, $CH_2$—O), 4.46 (s, 3H, $NCH_3$), 3.99 (s, 3H, $OCH_3$), 3.55-3.45 (m, 4H, $CH_2$—N), 2.86 (t, J=6.2 Hz, 2H, $CH_2$—Ar), 2.41 (t, J=6.9 Hz, 2H, $CH_2$—COO), 2.07-1.90 (m, 4H, $CH_2$—$CH_2$—N). LC-MS (ESI): (positive ion) m/z 419 ($M+H^+$).

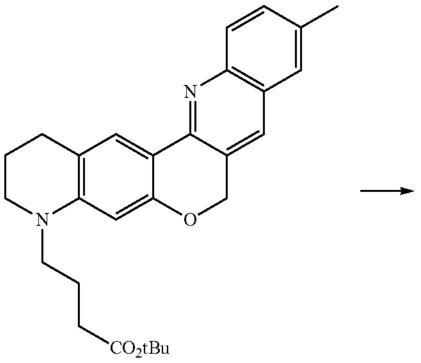

8b

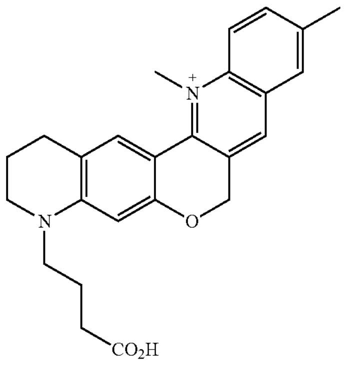

I-2

Compound 8b (89 mg, 0.20 mmol) was dissolved in dry 1,2-dichloroethane (2 mL) in a pressure tube. Methyl trifluoromethanesulfonate (0.45 mL, 4 mmol) and $K_2CO_3$ (138 mg, 1 mmol) were added, and the reaction was heated at 110° C. After 18 hours, the reaction was cooled down, the volatiles were removed under reduced pressure and the crude was purified by flash column chromatography. The intermediate was then dissolved in methanol (10 mL) and 0.5 mL of a 4M solution of NaOH in water were added. The reaction was stirred at RT for 18 hours. Then, the solution was neutralized with 1 N HCl, the volatiles were removed under reduced pressure and the crude was purified by preparative scale RP-HPLC on a C18 column to afford compound I-2 as a red solid. Yield: 30 μmol (15%). $^1H$ NMR (400 MHz, MeOD): δ (ppm) 8.33 (s, 1H, Ar—CH), 8.10 (d, J=8.8 Hz, 1H, Ar—CH), 7.92-7.84 (m, 2H, Ar—CH), 7.57 (s, 1H, Ar—CH), 6.53 (s, 1H, Ar—CH), 5.16 (s, 2H, $CH_2$—O), 4.44 (s, 3H, $NCH_3$), 3.56-3.52 (m, 2H, $CH_2$—N), 3.50-3.43 (m, 2H, $CH_2$—N), 2.85 (t, J=6.2 Hz, 2H, $CH_2$—Ar), 2.59 (s, 3H, $CH_3$), 2.25 (t, J=7.2 Hz, 2H, $CH_2$—COO), 2.06-1.89 (m, 4H, $CH_2$—$CH_2$—N). LC-MS (ESI): (positive ion) m/z 403 ($M+H^+$).

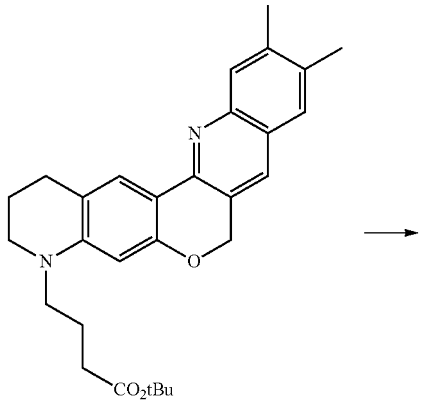

8c

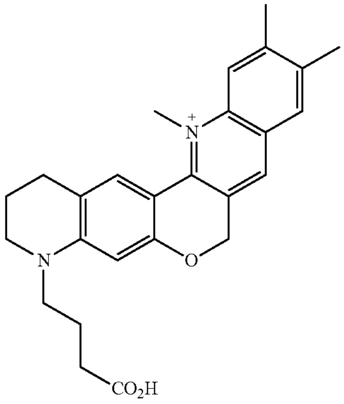

I-3

Compound 8c (30 mg, 0.065 mmol) was dissolved in dry 1,2-dichloroethane (1 mL) in a pressure tube. Methyl trifluoromethanesulfonate (1 mL) and diisopropylethylamine (0.5 mL) were added. After 1 hour at RT, the mixture was diluted with DCM (20 mL) and extracted with 20 mL of sat. $NaHCO_3$. The organic phase was dried over $MgSO_4$, filtered and evaporated to dryness under reduced pressure. The red residue was purified by flash column chromatography. The intermediate was then dissolved in methanol (10 mL) and 0.15 mL of a 4 M solution of NaOH in water were added. The reaction was stirred at RT for 18 hours. Then, the solution was neutralized with 1 N HCl (0.6 mL), the volatiles were removed under reduced pressure and the crude was purified by RP chromatography on a C18 column to afford compound I-3 as a red solid in a 6:4 mixture of two regioisomers. Yield: 15 μmol (35%). $^1H$ NMR (400 MHz, MeOD): δ (ppm) 8.71 (s, 0.4H, Ar—CH, isom B), 8.32 (s, 0.6H, isom A), 8.00 (s, 0.6H, Ar—CH, isom A), 7.96 (d, J=9.0 Hz, 0.4H, Ar—CH, isom B), 7.85 (d, J=9.0 Hz, 0.4H, Ar—CH, isom B), 7.82 (s, 0.6H, Ar—CH, isom A), 7.56 (s, 1H, Ar—CH), 6.54 (s, 0.4H, Ar—CH, isom B), 6.53 (s, 1H, 0.6H, Ar—CH, isom A), 5.21 (s, 0.8H, $CH_2$—O, isom B), 5.15 (s, 1.2H, $CH_2$—O, isom A), 4.44 (s, 3H, $CH_3$—N), 3.71-3.57 (m, TEAB), 3.57-3.51 (m, 2H, $CH_2$—N), 3.50-3.43 (m, 2H, $CH_2$—N), 2.85 (t, J=6.2 Hz, 2H, Ar—$CH_2$), 2.69 (s, 1H, $CH_3$ isom B), 2.63 (s, 2H, $CH_3$ isom A), 2.56 (s, 1H, $CH_3$ isom B), 2.51 (s, 2H, $CH_3$ isom A), 2.27 (t, J=7.2, 2H, $CH_2$—COO), 2.06-1.91 (m, 4H, $CH_2$—$CH_2$—N), 1.20 (t, J=7.0 Hz, TEAB). LC-MS (ESI): (positive ion) m/z 417 ($M+H^+$).

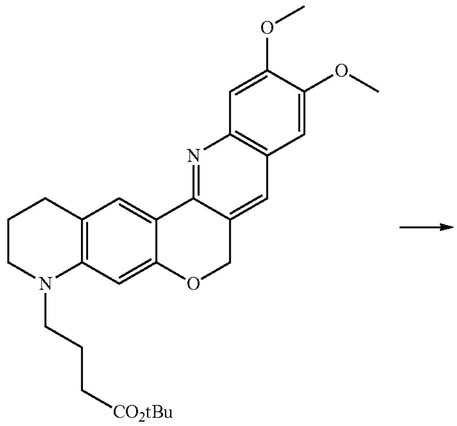

8d

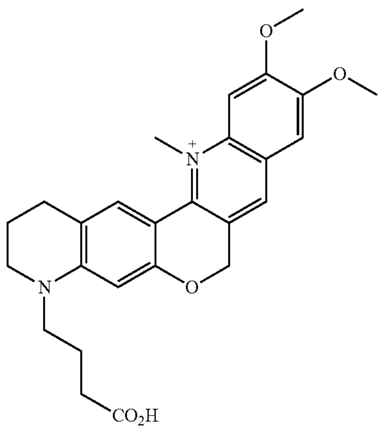

I-4

Compound 8d (65 mg, 0.132 mmol) was dissolved in dry dichloromethane (1 mL). Diisopropylethylamine (114 μL, 0.66 mmol) and methyl trifluoromethanesulfonate (300 μL, 2.65 mmol) and were added under $N_2$ atmosphere. After 1 hour, the volatiles were removed under reduced pressure. The crude was then dissolved in methanol (10 mL) and 0.5 mL of a 4M solution of NaOH in water were added. The reaction was stirred at RT for 18 hours. Then, the solution was neutralized with acetic acid (0.15 mL), the volatiles were removed under reduced pressure. The residue was purified firstly by flash column chromatography and then by RP chromatography on a C18 column to afford compound I-4 as a red solid. Yield: 92 μmol (69%). $^1H$ NMR (400 MHz, MeOD/$CDCl_3$): δ (ppm) 8.26 (s, 1H, Ar—CH), 7.71 (s, 1H, Ar—CH), 7.43 (s, 1H, Ar—CH), 7.42 (s, 1H, Ar—CH), 6.48 (s, 1H, Ar—CH), 5.12 (s, 2H, $CH_2$—O), 4.44 (s, 3H, $CH_3$—N), 4.15 (s, 3H, $CH_3$—O), 4.03 (s, 3H, $CH_3$—O), 3.70-3.55 (m, 1H, TEAB), 3.50 (d, J=5.6 Hz, 2H, $CH_2$—N), 3.44 (d, J=7.7 Hz, 2H, $CH_2$—N), 2.82 (t, J=6.2 Hz, 2H, Ar—$CH_2$), 2.25 (t, J=7.2 Hz, 2H, $CH_2$—COO), 2.06-1.85 (m, 4H, $CH_2$—$CH_2$—N), 1.17 (t, J=7.0 Hz, 1H, TEAB). LC-MS (ESI): (positive ion) m/z 449 ($M+H^+$).

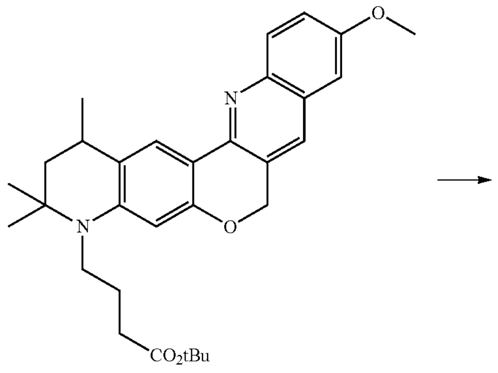

8e

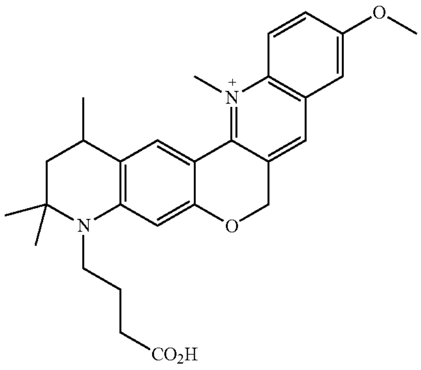

I-5

Compound 8e (80 mg, 0.159 mmol) was dissolved in dry 1,2-dichloroethane (2 mL) in a pressure tube. Methyl trifluoromethanesulfonate (360 μL, 3.18 mmol) and $K_2CO_3$ (109 mg, 0.795 mmol) were added under $N_2$ atmosphere and the reaction was heated to 110° C. for 24 hours. The volatiles were removed under reduced pressure and the red residue was purified by flash column chromatography. The intermediate was then dissolved in methanol (5 mL) and 0.35 mL of a 4M solution of NaOH in water were added. The reaction was stirred at RT for 18 hours. Then, the solution was neutralized with 1N HCl (0.15 mL). The volatiles were removed under reduced pressure and the crude was purified firstly by flash column chromatography then by RP chromatography on a C18 column to afford compound I-5 as a red solid. Yield: 69 μmol (43%). $^1$H NMR (400 MHz, MeOD/$CDCl_3$): δ (ppm) 8.36 (s, 1H, Ar—CH), 8.16 (d, J=9.5 Hz, 1H, Ar—CH), 7.69-7.63 (m, 2H, Ar—CH), 7.51 (d, J=2.9 Hz, 1H, Ar—CH), 6.54 (s, 1H, Ar—CH), 5.19 (d, J=13.7 Hz, 1H, O—CHH), 5.12 (d, J=13.7 Hz, 1H, O—CHH), 4.47 (s, 3H, $CH_3$—N), 4.00 (s, 3H, $CH_3$—O), 3.63 (q, J=7.1 Hz, 1H, TEAB), 3.58-3.47 (m, 1H, CHH—N), 3.36-3.29 (m, CHH—N under MeOH), 3.03-2.89 (m, 1H, Ar—CH), 2.27 (d, J=7.1 Hz, 2H, $CH_2$—COO), 2.04-1.84 (m, 4H, $CH_2$—$CH_2$—N), 1.47 (s, 3H, $CH_3$), 1.46 (d, J=6.5 Hz, 3H, $CH_3$), 1.35 (s, 3H, $CH_3$), 1.20 (t, J=7.0 Hz, 2H, TEAB). LC-MS (ESI): (positive ion) m/z 461 (M+H$^+$).

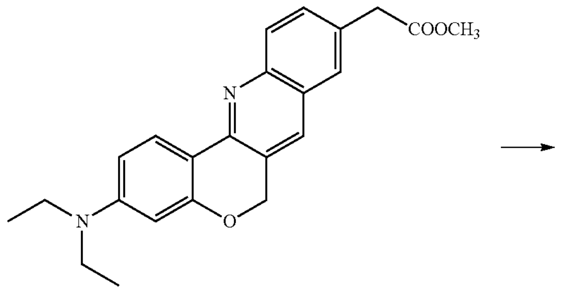

8f

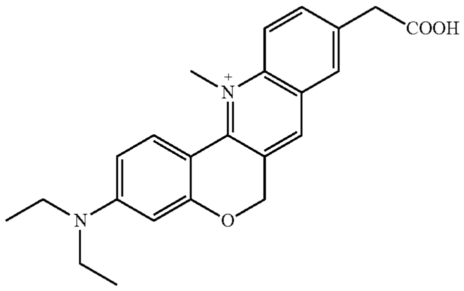

I-6

Compound 8f (310 mg, 0.182 mmol) was dissolved in dry 1,4-dioxane (2 mL) in a pressure tube. Iodomethane (0.5 mL, 8 mmol) was added, and the reaction was heated at 100° C. in the dark. After 2 days, the volatiles were removed under reduced pressure and the intermediate was then dissolved in methanol (5 mL) and 1 mL of a 4 M solution of NaOH in water was added. The reaction was stirred at RT for 18 hours. Then, the solution was neutralized with 1 N HCl (0.15 mL). The volatiles were removed under reduced pressure and the crude was purified by preparative scale RP-HPLC on a C18 column to afford compound I-6 as a red solid. Yield: 28 μmol (15%). $^1$H NMR (400 MHz, MeOD): δ (ppm) 8.47 (s, 1H, Ar—CH), 8.15 (d, J=9.0 Hz, 1H, Ar—CH), 8.02 (dd, J=9.0, 2.0 Hz, 1H, Ar—CH), 7.98 (d, J=2.0 Hz, 1H, Ar—CH), 7.91 (d, J=9.4 Hz, 1H, Ar—CH), 6.80 (dd, J=9.4, 2.6 Hz, 1H, Ar—CH), 6.51 (d, J=2.7 Hz, 1H, Ar—CH), 5.25 (s, 2H, $CH_2$—O), 4.49 (s, 3H, $NCH_3$), 3.73 (s, 3H, $OCH_3$), 3.59 (q, J=7.1 Hz, 4H, $CH_2$—N), 2.65 (q, J=7.2 Hz, 6H, TEAB), 1.29 (t, J=7.1 Hz, 6H, $CH_3$ Et), 1.10 (t, J=7.2 Hz, 9H, TEAB). LC-MS (ESI): (positive ion) m/z 377 (M+H$^+$).

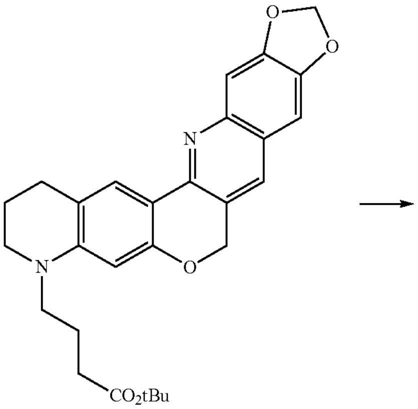

8g

-continued

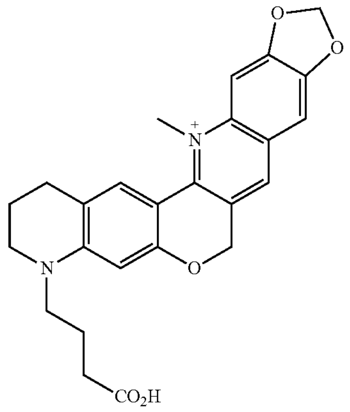

I-7

-continued

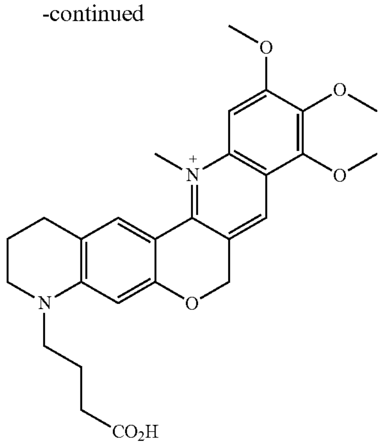

I-8

Compound 8g (65 mg, 0.137 mmol) was dissolved in dry dichloromethane (2 mL). Methyl trifluoromethanesulfonate (77 μL, 0.68 mmol) and N,N-diisopropylethylamine (118 μL, 0.68 mmol) were added at 0° C. under $N_2$ atmosphere, then reaction was stirred at RT for 4 hours. Another portion of methyl trifluoromethanesulfonate (77 μL, 0.68 mmol) and N,N-diisopropylethylamine (118 μL, 0.68 mmol) and 2 mL of dry DCM were added. After further 2 hours the volatiles were removed under reduced pressure. The red residue was purified by flash column chromatography. The intermediate was then dissolved in methanol (10 mL) and 0.375 mL of a 4 M solution of NaOH in water were added. The reaction was stirred at 60° C. for 2 hours. Then, the solution was neutralized with acetic acid (0.09 mL). The volatiles were removed under reduced pressure and the crude was purified by RP chromatography on a C18 column to afford compound I-7 as a red solid. Yield: 9.8 μmol (7%). $^1$H NMR (400 MHz, MeOD): δ (ppm) 8.24 (s, 1H, Ar—CH), 7.62 (s, 1H, Ar—H), 7.47 (s, 1H, Ar—CH), 7.34 (s, 1H, Ar—CH), 6.48 (s, 1H, Ar—CH), 6.29 (s, 2H, O—$CH_2$—O), 5.08 (s, 2H, $CH_2$—O), 4.38-4.31 (m, 3H, $CH_3$—N), 3.50 (t, J=5.4 Hz, 2H, $CH_2$—N), 3.44 (t, J=7.8 Hz, 2H, $CH_2$—N), 2.81 (m, 2H, Ar—$CH_2$), 2.25 (m, 2H, $CH_2$—COO), 2.02-1.87 (m, 4H, $CH_2$—$CH_2$—N), 1.20 (t, J=7.0 Hz, 2H, TEAB). LC-MS (ESI): (positive ion) m/z 433 (M+$H^+$).

Compound 8h (65 mg, 0.117 mmol) was dissolved in dry dichloromethane (2 mL). Methyl trifluoromethanesulfonate (27 μL, 0.234 mmol) and N,N-diisopropylethylamine (41 μL, 0.234 mmol) were added at 0° C. under $N_2$ atmosphere, then reaction was stirred at RT for 2 hours. Then further methyltrifluoromethanesulfonate (54 μL, 0.46 mmol) and N,N-diisopropylethylamine (82 μL, 0.46 mmol) were added, and the reaction was stirred at RT for 2 hours. Then, further methyltrifluoromethanesulfonate (100 μLt, 0.88 mmol) and N,N-diisopropylethylamine (82 μL, 0.46 mmol) were added, and the reaction was stirred at RT for 1 hour, then the volatiles were removed under reduced pressure. The intermediate was dissolved in methanol (2 mL) and 0.5 mL of a 4M solution of NaOH in water were added. The reaction was stirred at RT for overnight. Then, the solution was neutralized with acetic acid (0.24 mL). The volatiles were removed under reduced pressure and the crude was purified by RP chromatography on a C18 column to afford compound I-8 as a red solid. Yield: 70 μmol (60%). $^1$H NMR (400 MHz, MeOD/$CDCl_3$): δ (ppm) 8.49 (s, 1H, Ar—CH), 7.51 (s, 1H, Ar—CH), 7.23 (s, 1H, Ar—CH), 6.49 (s, 1H, Ar—CH), 5.09 (s, 2H, $CH_2$—O), 4.40 (s, 3H, $CH_3$—N), 4.16 (s, 3H, $CH_3$—O), 4.15 (s, 3H, $CH_3$—O), 3.98 (s, 3H, $CH_3$—O), 3.54-3.50 (m, 2H, $CH_2$—N), 3.47-3.41 (m, 2H, $CH_2$—N), 2.84 (t, J=6.2 Hz, 2H, Ar—$CH_2$), 2.24 (t, J=7.2 Hz, 2H, $CH_2$—COO), 2.04-1.89 (m, 4H, $CH_2$—$CH_2$—N). LC-MS (ESI): (positive ion) m/z 479 (M+$H^+$).

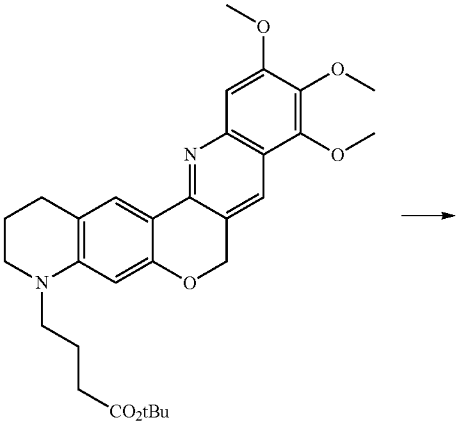

8h

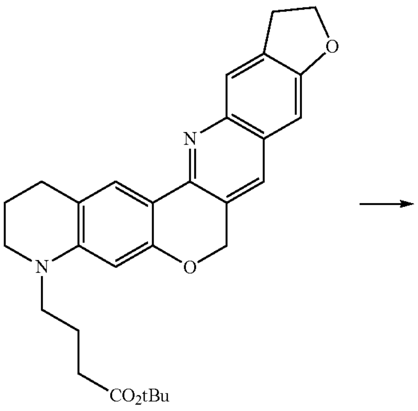

8i

-continued

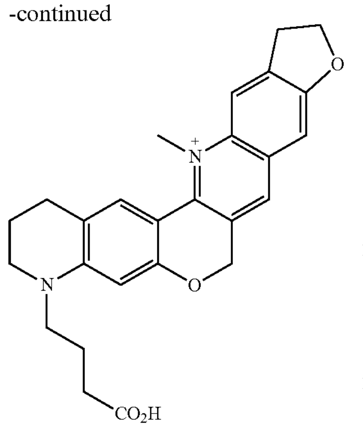

I-9

Compound 8i (50 mg, 0.1 mmol) was dissolved in dry dichloromethane (1 mL). N,N-diisopropylethylamine (208 μL, 1.2 mmol) and methyl trifluoromethanesulfonate (600 μL, 5 mmol) were added at 0° C. under $N_2$ atmosphere, then reaction was stirred at RT for 2 hours. Then further methyl trifluoromethanesulfonate (600 μL, 5 mmol) and N,N-diisopropylethylamine (208 μL, 1.2 mmol) were added, and the reaction was stirred at RT for 2 hours. Then, the volatiles were removed under reduced pressure. The red residue was purified by flash column chromatography. The intermediate was dissolved in methanol (5 mL) and 0.25 mL of a 4M solution of NaOH in water were added. The reaction was stirred at RT overnight. Then, the solution was neutralized with acetic acid (0.06 mL). The volatiles were removed under reduced pressure and the crude was purified by RP chromatography on a C18 column to afford compound I-9 as a red solid. Yield: 4.1 μmol (4%), as a red solid. $^1H$ NMR (400 MHz, MeOD/$CDCl_3$): δ (ppm) 8.30 (s, 1H, Ar—CH), 8.13 (s, 1H, Ar—CH), 7.54 (s, 1H, Ar—CH), 7.28 (s, 1H, Ar—CH), 6.54 (s, 1H, Ar—CH), 5.17-5.14 (m, 2H, $CH_2$—O), 4.80 (t, J=8.4 Hz, 2H, $CH_2$—$CH_2$—O), 4.49-4.40 (m, 3H, $CH_3$—N), 3.70-3.44 (m, 6H, $CH_2$—N, $CH_2$—$CH_2$—O), 2.85 (t, J=6.2 Hz, 2H, Ar—$CH_2$), 2.27 (t, J=7.2 Hz, 2H, $CH_2$—COO), 2.04-1.93 (m, 4H, $CH_2$—$CH_2$—N). LC-MS (ESI): (positive ion) m/z 431 (M+$H^+$).

Example 2. General Synthesis of Chromenoquinoline Dyes Labeled Nucleotides

The chromenoquinoline dye of Formula (I) (0.020 mmol) was coevaporated with 2×2 mL of anhydrous N,N'-dimethylformamide (DMF), then dissolved in 2 mL of anhydrous N,N'-dimethylacetamide (DMA). N,N-diisopropylethylamine (28.4 μL, 0.163 mmol) was added, followed by N,N,N',N'-tetramethyl-O—(N-succinimidyl)uronium tetrafluoroborate as 0.1 M solution in anhydrous DMA (TSTU, 232 μL, 0.023 mmol). The reaction was stirred under nitrogen at RT for 30 minutes. In the meantime, an aqueous solution of the 2'-deoxyadenosine triphosphates-linker (0.01 mmol) was evaporated to dryness under reduced pressure and resuspended in 200 μL, of 0.1 M triethylammonium bicarbonate (TEAB) solution in water. The activated chromenoquinoline dye solution was added to the triphosphate and the reaction was stirred at RT for 18 hours. The crude product was purified firstly by ion-exchange chromatography on DEAE-Sephadex A25 (25 g). The fractions containing the triphosphate were pooled and the solvent was evaporated to dryness under reduced pressure. The crude material was further purified by preparative scale RP-HPLC using a YMC-Pack-Pro C18 column. The final compound was characterized by LC-MS, analytical RP-HPLC and UV-Vis spectroscopy.

ffA-LN3-I-1

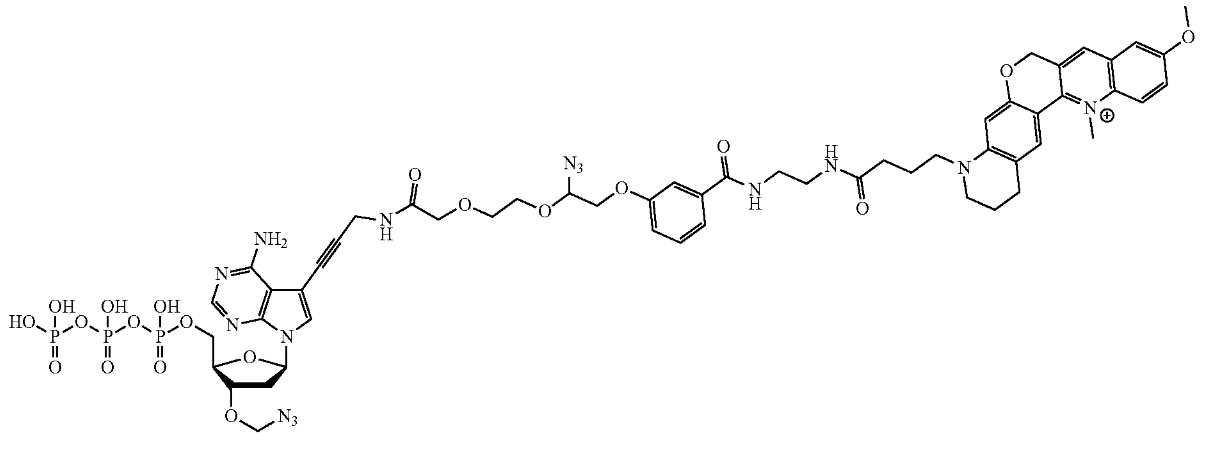

Compound ffA-LN3-I-1: Yield: 2.7 μmol, (54%). LC-MS (ES): (negative ion) m/z 1346 (M-$H^+$), 673 (M-2$H^+$). UV-VIS $\lambda_{max}$=503 nm. Fluorescence em. $\lambda_{max}$=590 nm.

ffA-LN3-I-2
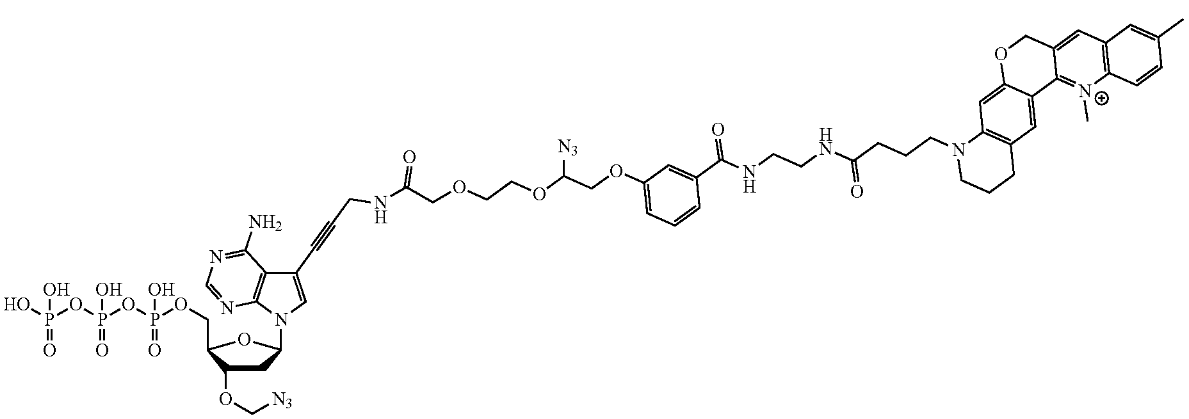
Compound ffA-LN3-I-2: Yield: 6.8 μmol (68%). LC-MS (ES): (negative ion) m/z 1330 ($M-H^+$), 665 ($M-2H^+$). UV-VIS $\lambda_{max}$=500 nm. Fluorescence em. $\lambda_{max}$=582 nm.
ffA-sPA-LN3-I-3
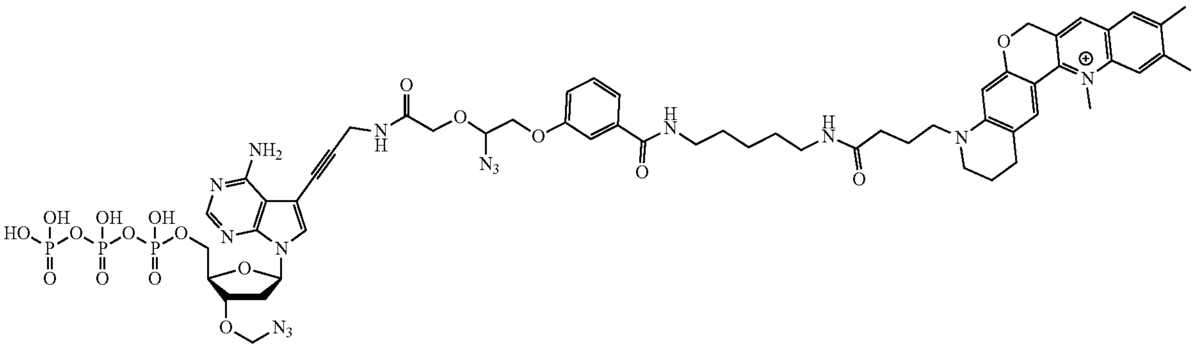
Compound ffA-sPA-LN3-I-3: Yield: 6.3 μmol (63%). LC-MS (ES): (negative ion) m/z 1343 ($M-H^+$), 671 ($M-2H^+$). UV-VIS $\lambda_{max}$=500 nm. Fluorescence em. $\lambda_{max}$=578 nm.
ffA-sPA-LN3-I-4
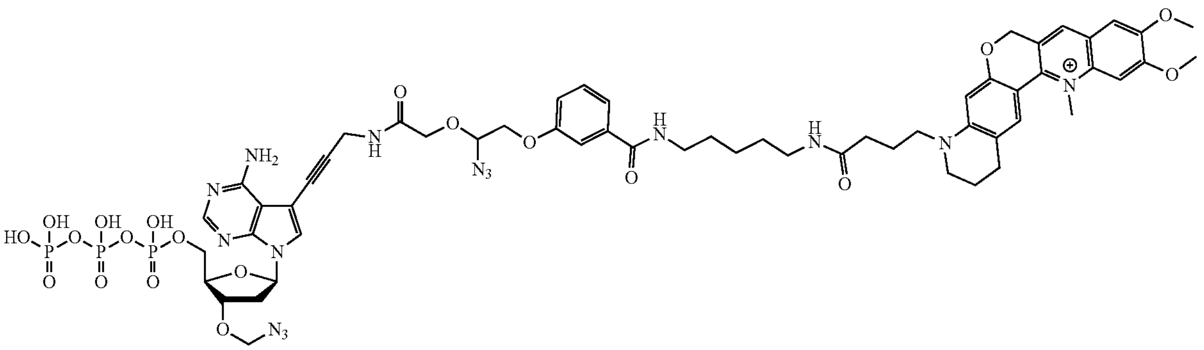

Compound ffA-sPA-LN3-1-4: Yield: 7.8 μmol (78%). LC-MS (ES): (negative ion) m/z 1375 ($M-H^+$), 687 ($M-2H^+$). UV-VIS $\lambda_{max}$=500 nm. Fluorescence em. $\lambda_{max}$=578 nm.

ffA-LN3-I-5

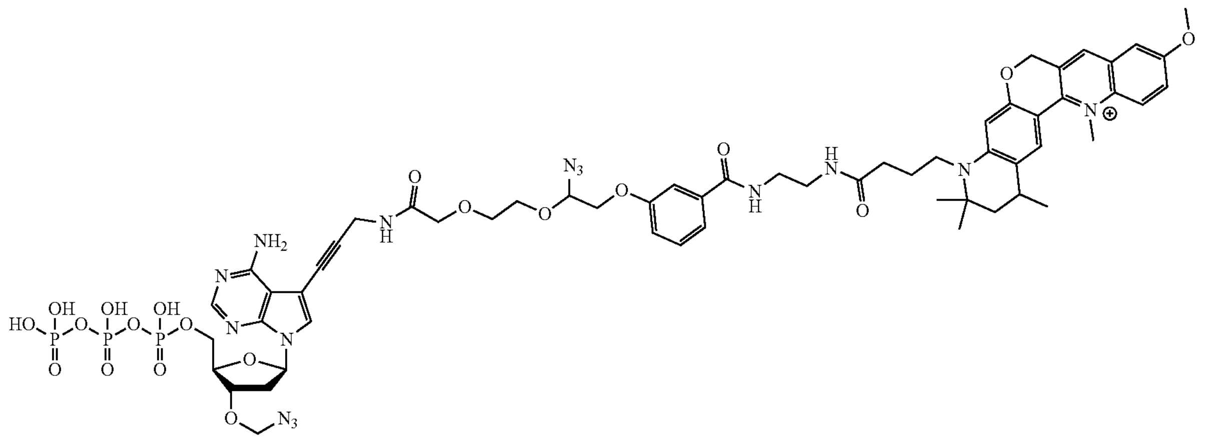

Compound ffA-LN3-I-5: Yield: 7.3 mol (73%). LC-MS (ES): (negative ion) m/z 1388 ($M-H^+$), 694 ($M-2H^+$). UV-VIS $\lambda_{max}$=501 nm. Fluorescence em. $\lambda_{max}$=585 nm.

ffA-LN3-I-6

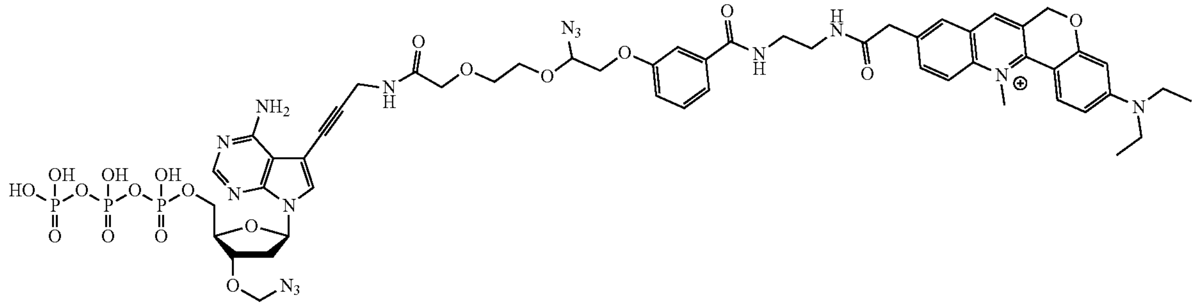

Compound ffA-LN3-I-6: Yield: 3.1 μmol (31%). LC-MS (ES): (negative ion) m/z 1304 ($M-H^+$), 652 ($M-2H^+$). UV-VIS $\lambda_{max}$=495 nm. Fluorescence em. $\lambda_{max}$=574 nm.

ffA-sPA-LN3-I-8

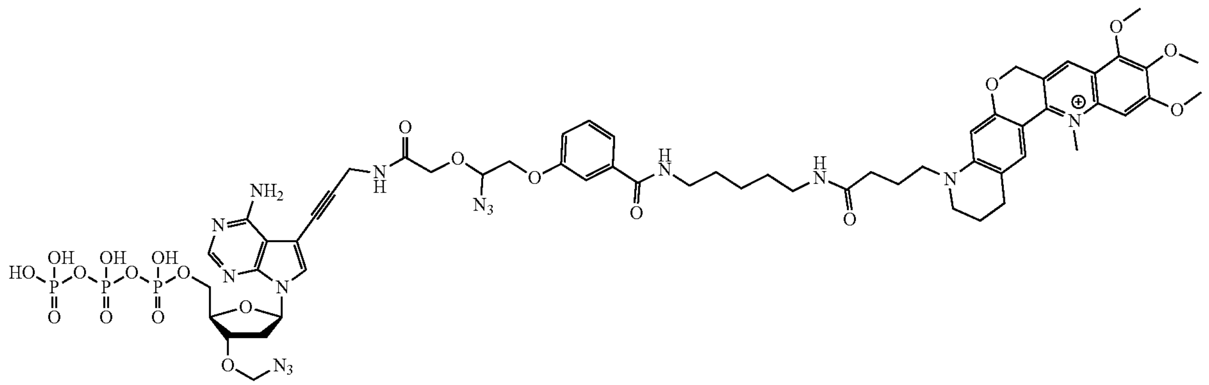

Compound ffA-sPA-LN3-I-8: Yield: 6.9 μmol (69%). LC-MS (ES): (negative ion) m/z 1405 (M−H$^+$), 702 (M−2H$^+$). UV-VIS $\lambda_{max}$=500 nm. Fluorescence em. $\lambda_{max}$=583 nm.

ffA-AOM-AOL-I-4

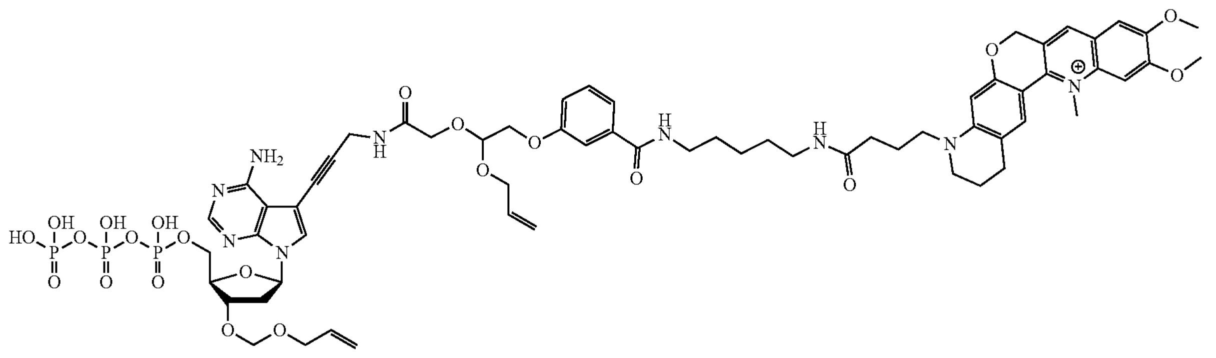

Compound ffA-AOM-AOL-I-4: Yield: 10 μmol (50%). LC-MS (ES): (negative ion) m/z 1405 (M−H$^+$), 702 (M−2H$^+$). UV-VIS $\lambda_{max}$=500 nm. Fluorescence em. $\lambda_{max}$=578 nm.

ffA-(DB)-AOM-AOL-I-4

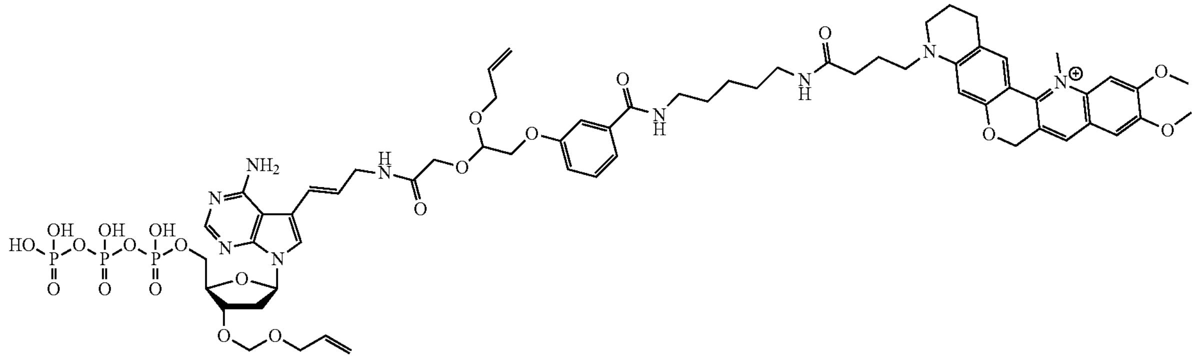

Compound ffA-(DB)-AOM-AOL-I-4: Yield: 2.1 μmol (21%). LC-MS (ES): (negative ion) m/z 1407 (M−H$^+$), 703 (M−2H$^+$). UV-VIS $\lambda_{max}$=500 nm. Fluorescence em. $\lambda_{max}$=578 nm.

Example 3. Spectral Properties of ffA Nucleotides Conjugated with Chromenoquinoline Dyes In this example, the spectral properties of several fully functionalized A nucleotides (ffAs) conjugated with the chromenoquinoline dyes described herein were characterized. FIG. 1 illustrates the fluorescent absorption spectra of ffA nucleotides conjugated with chromenoquinoline dyes I-1 through I-6 and I-8 as a 2 μM solution in Universal Scan Mix (USM, 1 M Tris pH 7.5, 0.05% TWEEN, 20 mM sodium ascorbate, 10 mM ethyl gallate). FIGS. 2A-2D show the fluorescence emission spectra of ffA nucleotide conjugated with chromenoquinoline dyes I-1 through I-6 and I-8 acquired using either 450 nm or 520 nm as excitation wavelengths in USM. The spectra were acquired on an Agilent Cary 100 UV-Vis Spectrophotometer and on a Cary Eclipse Fluorescence Spectrophotometer, using quartz or plastic cuvettes. It was observed that the chromenoquinoline dyes described herein can be excited under both blue and green light sources and also have strong fluorescent emission.

Example 4. Stability of Chromenoquinoline Dye Labeled ffAs

Figure 3A:
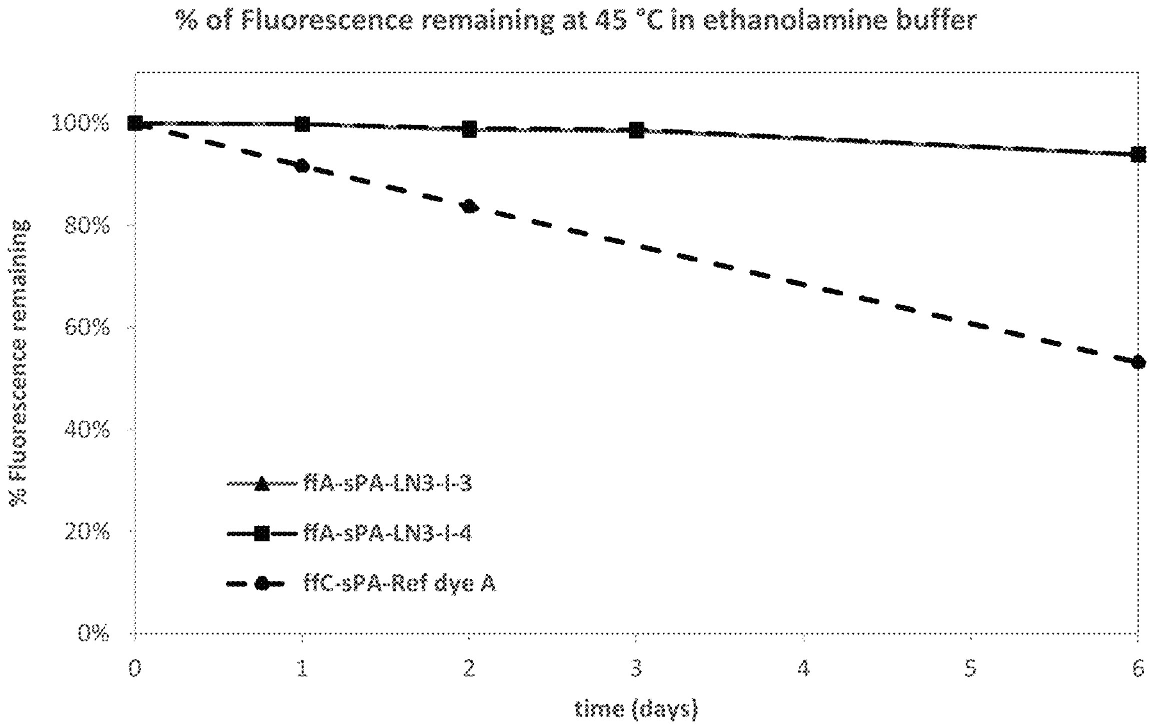
FIG. 3A shows the percent fluorescence remaining of two ffA conjugated with chromenoquinoline dyes I-3 and I-4 at 45° C. in an ethanolamine buffer as compared to that of an ffC conjugated with a coumarin reference dye A at the same condition.
Figure 3B:
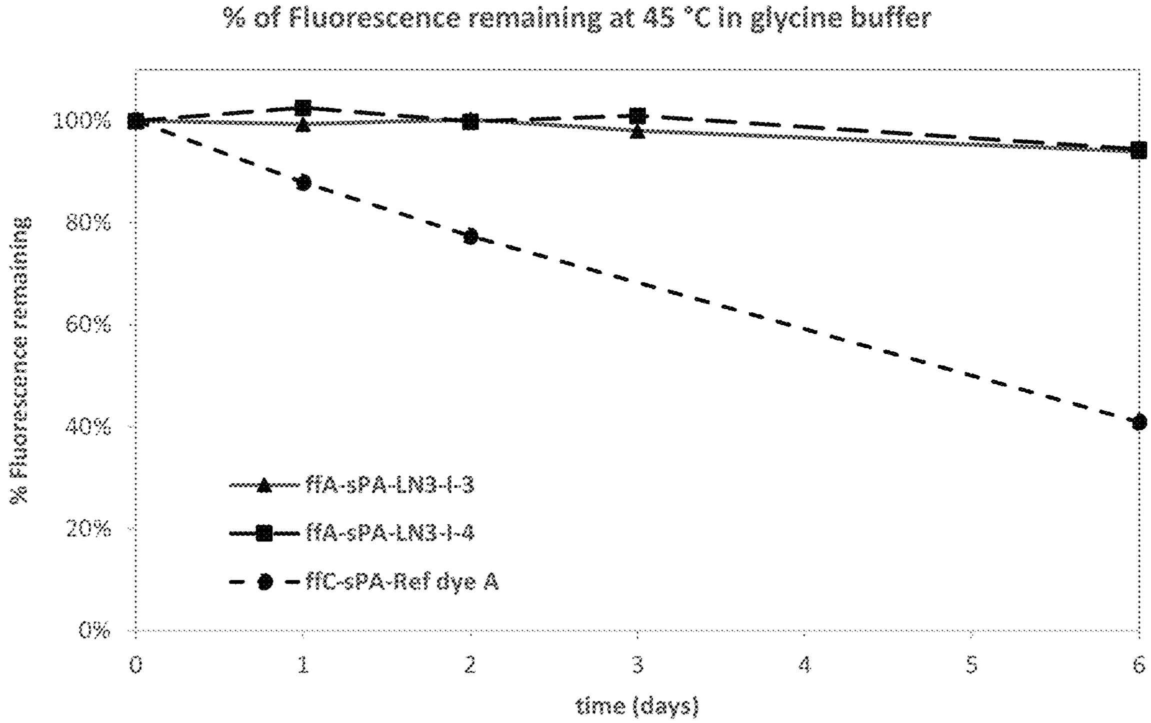
FIG. 3B shows the percent fluorescence remaining of two ffA conjugated with chromenoquinoline dyes I-3 and I-4 at 45° C. in a glycine buffer as compared to that of an ffC conjugated with a coumarin reference dye A at the same condition.

The stability of the compounds ffA-sPA-I-3 and ffA-sPA-I-4 in an aqueous solution at high pH was assessed by incubating a 10 μM solution of the given compound in two buffers: 1) 50 mM ethanolamine buffer, pH 9.6, 50 mM NaCl, 1 mM EDTA, 0.02% CHAPS, 4 mM $MgSO_4$; 2) 50 mM glycine buffer, pH 9.8, 50 mM NaCl, 1 mM EDTA, 0.2% CHAPS, 4 mM $MgSO_4$ at 45° C. in the dark for 6 days. At set time points, the UV-VIS absorption and fluorescence emission of the solutions were measured on an Agilent Cary 100 UV-Vis Spectrophotometer and on a Cary Eclipse Fluorescence Spectrophotometer, using quartz cuvettes. In addition, aliquots of the solutions were taken and analyzed by analytical HPLC. FIG. 3A and FIG. 3B show that the fluorescence emission of ffA-sPA-I-3 and ffA-sPA-I-4 decreased very slowly over time, indicating that the chromenoquinoline dyes I-3 and I-4 are stable under these conditions, as compared to an ffC labeled with a bright coumarin reference dye A under the same condition. The coumarin reference dye A is disclosed in U.S. Publication No. 2018/0094140, having the structure moiety

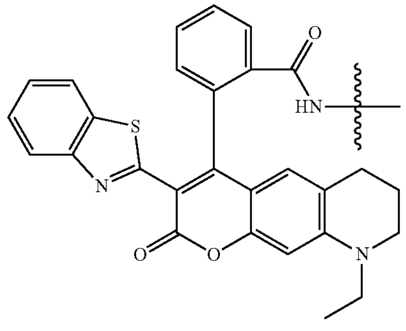 [SMILES: *NC(=O)c1ccccc1-c1c(-c2nc3ccccc3s2)c(=O)oc2cc3c(cc12)CCCN3CC]

when conjugated with the ffC.

Figure 3C:
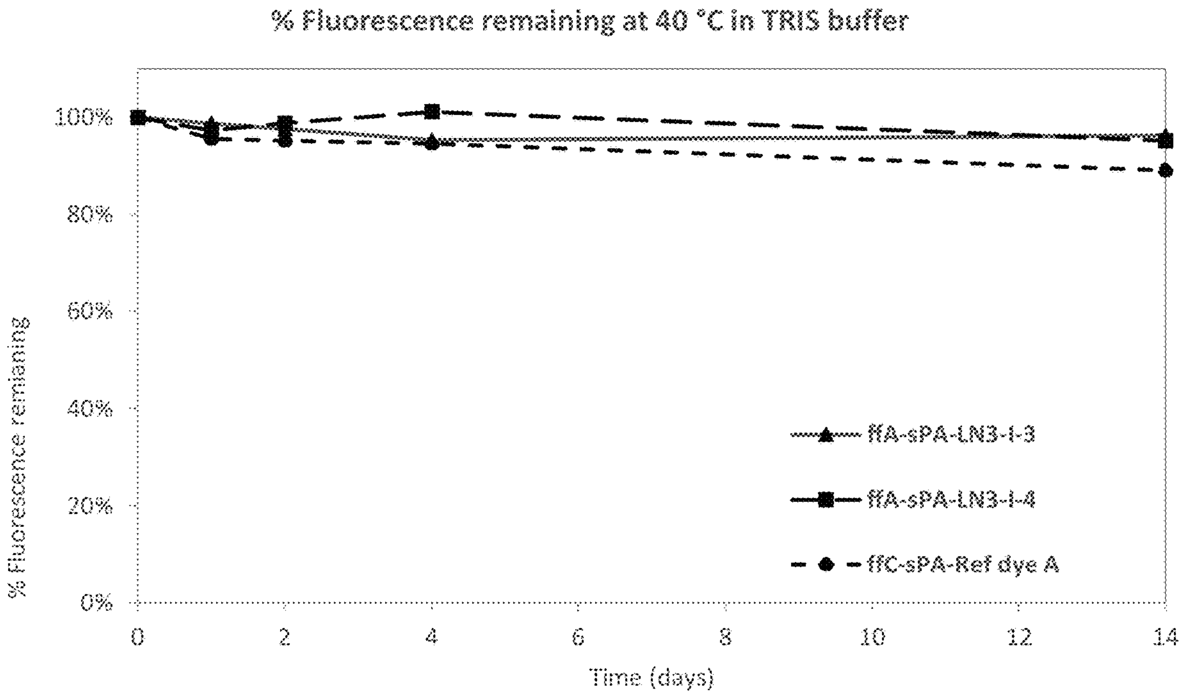
FIG. 3C shows the percent fluorescence remaining of two ffA conjugated with chromenoquinoline dyes I-3 and I-4 at 40° C. in a TRIS buffer as compared to that of an ffC conjugated with a coumarin reference dye A at the same condition.
Figure 3D:
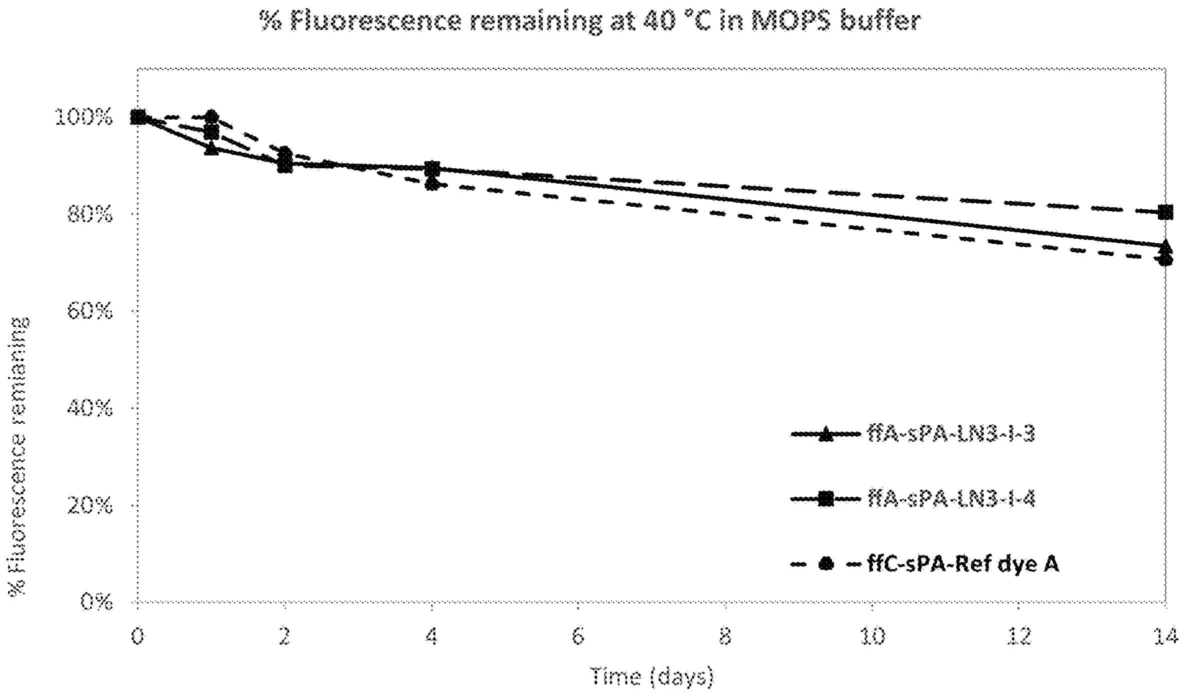
FIG. 3D shows the percent fluorescence remaining of two ffA conjugated with chromenoquinoline dyes I-3 and I-4 at 40° C. in a MOPS buffer as compared to that of an ffC conjugated with a coumarin reference dye A at the same condition.

In addition, the stability of the compounds ffA-sPA-I-3 and ffA-sPA-I-4 in a buffer suitable for nucleotide storage was assessed by incubating a 10 μM solution in two buffers: 1) 10 mM Tris buffer, pH 8.0; 2) 100 mM MOPS buffer, pH 7.0, at 40° C., in the dark for 14 days. At set time points, the UV-VIS absorption and fluorescence emission of the solutions were measured on an Agilent Cary 100 UV-Vis Spectrophotometer and on a Cary Eclipse Fluorescence Spectrophotometer, using quartz cuvettes. In addition, aliquots of the solutions were taken and analyzed by analytical HPLC. FIG. 3C and FIG. 3D show that ffA-sPA-I-3 and ffA-sPA-I-4 retained >90% of their fluorescence after 14 days in Tris pH 8.0 and >75% after 14 days in MOPS pH 7.0, as compared to the coumarin reference dye A at the same condition

Example 5. Sequencing Experiments on Illumina iSeq™ 100 Instrument

Figure 4A:
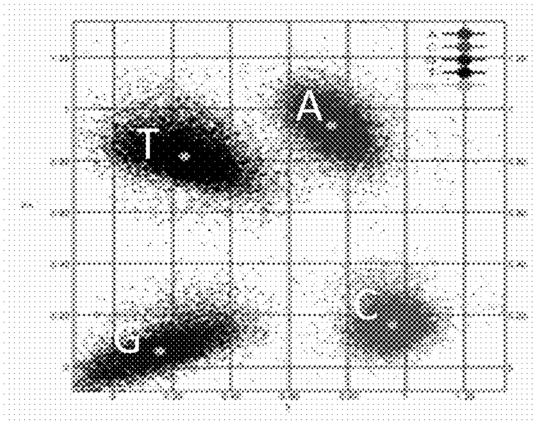
FIGS. 4A-4E show the scatterplots obtained on an Illumina iSeq™ 100 instrument using the incorporation mix with ffA nucleotide labeled with chromenoquinoline dyes I-1, I-2, I-3, I-4 and I-5 respectively.
Figure 4B:
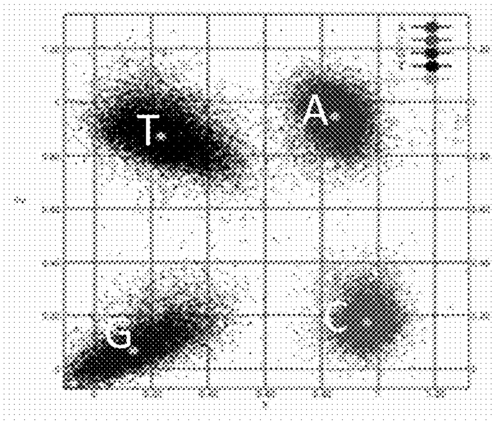
Figure 4C:
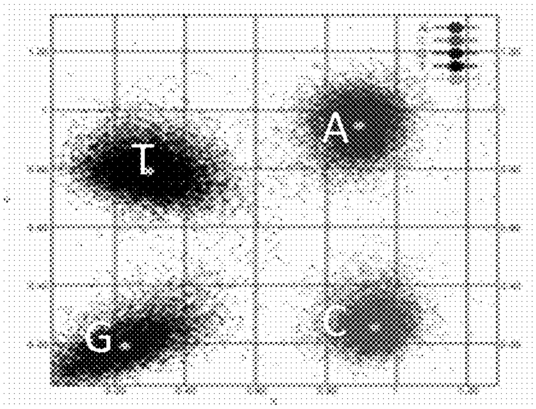
Figure 4D:
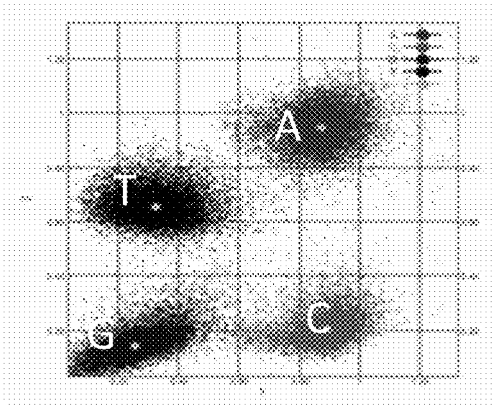
Figure 4E:
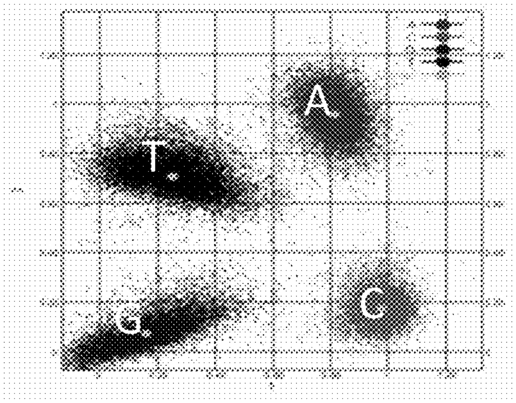
Figure 4F:
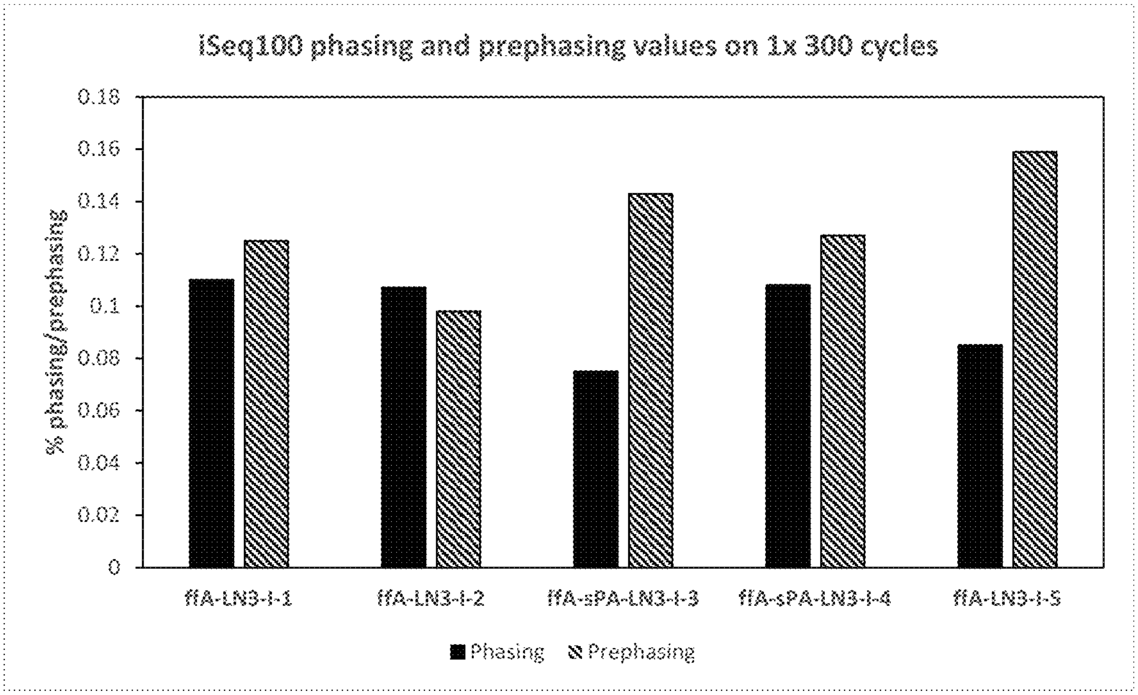
FIG. 4F illustrates the phasing and prephasing metrics on 1×300 cycles using the incorporation mix with ffA nucleotide labeled with chromenoquinoline dyes I-1, I-2, I-3, I-4 and I-5.

The ffAs labeled with the chromenoquinoline dyes described herein were tested on an Illumina iSeq™ 100 instrument, which had been set up to take the first image with a green excitation light (~520 nm) and the second image with a blue excitation light (~450 nm). The sequencing recipe was modified in order to perform a standard SBS cycle (incorporation, followed by imaging, followed by cleavage) for 1×300 cycles. The incorporation mix used in each of these experiments contained the following four ffNs: an ffA labeled with a chromenoquinoline dye of Formula (I), an ffC excitable with blue light at 450 nm (for example ffC-linker-coumarin reference dye A), an ffT excitable with green light (e.g., ffT-linker-NR550s0) and an unlabeled ffG (dark ffG) in 50 mM ethanolamine buffer, pH 9.6, 50 mM NaCl, 1 mM EDTA, 0.2% CHAPS, 4 mM $MgSO_4$ and a DNA polymerase. FIGS. 4A-4E show the scatterplots obtained for the incorporation mix with ffA nucleotide labeled with chromenoquinoline dyes I-1, I-2, I-3, I-4 and I-5 respectively at cycle 26. FIG. 4F illustrates the phasing and prephasing metrics on 1×300 cycles. All ffAs tested showed excellent quality scatterplots and sequencing metrics.

Table 1 shows the phasing, prephasing, PhiX error rates and % Q30 metrics of a 2×300 cycles run on an Illumina iSeq™ 100 instrument, performed with an incorporation mix containing ffA-sPA-LN3-I-4. The instrument was set up to take the first image with a green excitation light and the second image with the blue excitation light, and the recipe was modified in order to perform a standard SBS cycle (incorporation, followed by imaging, followed by cleavage) for 2×300 cycles. The incorporation mix used in these experiments contained the nucleotides ffA-sPA-LN3-I-4, an ffC excitable with blue light at 450 nm (for example ffC-linker-coumarin reference dye A), an ffT excitable with green light (e.g., ffT-linker-NR550s0) and dark ffG in 50 mM ethanolamine buffer pH 9.6, 50 mM NaCl, 1 mM EDTA, 0.2% CHAPS, 4 mM $MgSO_4$ and a DNA polymerase.

TABLE 1 iSeq ™ 100 Sequencing Metrics (2 × 300 cycles) using ffA-sPA-LN3-I-4

| | Phasing | Prephasing | Error Rate (%) | % Q30 | % Q30 (Last 10 Cycles) |
|---|---|---|---|---|---|
| Read 1 | 0.111 | 0.129 | 0.81 | 91.49 | 72.75 |
| Read 2 | 0.11 | 0.141 | 1.01 | 85.57 | 55.56 |

Table 2 shows the phasing, prephasing, PhiX error rates and % Q30 metrics of a 2×150 cycles and a 2×300 cycles runs on an Illumina iSeq™ 100 instrument, performed with an incorporation mix containing ffA-AOM-AOL-I-4. The instrument was set up to take the first image with a green excitation light and the second image with the blue excitation light, and the recipe was modified in order to perform a standard SBS cycle (incorporation, followed by imaging, followed by cleavage) for 2×300 cycles. The incorporation mix used in these experiments contained the nucleotides ffA-AOM-AOL-I-4, an ffC excitable with blue light at 450 nm and cleavable with a palladium complex, an ffT excitable with green light at 520 nm and cleavable with a palladium complex and dark ffG cleavable with a palladium complex, in 50 mM glycine buffer pH 9.8, 50 mM NaCl, 1 mM EDTA, 0.2% CHAPS, 4 mM $MgSO_4$ and a DNA polymerase. The cleavage solution used in these experiments contained 100 mM diethylethanolamine buffer pH 9.5, 100 mM tris(hydroxypropyl)phosphine, 10 mM $[AllylPdCl]_2$, 10 mM sodium ascorbate, 1 M NaCl, 0.1% Tween20.

TABLE 2 iSeq ™ 100 Sequencing Metrics (2 × 150 and 2 × 300 cycles) using ffA-AOM-AOL-I-4

| | N of cycles | Phasing | Preptlasing | Error Rate (%) | % Q30 |
|---|---|---|---|---|---|
| Read 1 | 150 | 0.156 | 0.059 | 0.53 | 92.84 |
| Read 2 | 150 | 0.197 | 0.07 | 0.53 | 91.16 |
| Read 1 | 300 | 0.128 | 0.064 | 0.74 | 93.05 |
| Read 2 | 300 | 0.142 | 0.053 | 0.65 | 90.9 |

What is claimed is:

1. A compound of Formula (I), a salt or a mesomeric form thereof:

(I)

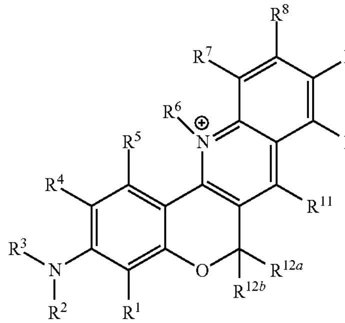

wherein each of $R^1$, $R^4$, $R^5$, $R^7$, $R^8$, $R^9$, $R^{10}$, $R^{11}$, $R^{12a}$ and $R^{12b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy) $C_1$-$C_6$ alkyl, optionally substituted amino, amino ($C_1$-$C_6$ alkyl), halo, cyano, hydroxy, hydroxy ($C_1$-$C_6$ alkyl), nitro, sulfonyl, sulfo, sulfino, sulfonate, S-sulfonamido, or N-sulfonamido;

each of $R^2$ and $R^3$ is independently H, $C_1$-$C_6$ alkyl, or substituted $C_1$-$C_6$ alkyl; and $R^6$ is $C_1$-$C_6$ alkyl or substituted $C_1$-$C_6$ alkyl;

alternatively, $R^1$ and $R^2$ together with the atoms to which they are attached form an optionally substituted 5-10 membered heteroaryl or an optionally substituted 5-10 membered heterocyclyl;

alternatively, $R^3$ and $R^4$ together with the atoms to which they are attached form an optionally substituted 5-10 membered heteroaryl or an optionally substituted 5-10 membered heterocyclyl;

alternatively, $R^8$ and $R^9$ together with the atoms to which they are attached form an optionally substituted C6-C10 aryl, an optionally substituted 3-10 membered carbocyclyl, an optionally substituted 5-10 membered heteroaryl or an optionally substituted 3-10 membered heterocyclyl;

provided that when each of $R^2$ and $R^3$ is ethyl; each of $R^1$, $R^4$, $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl; and provided that when $R^1$ and $R^2$ together with the atoms to which they are attached form a piperidinyl and $R^3$ and $R^4$ together with the atoms to which they are attached form a piperidinyl such that the compound has the structure;

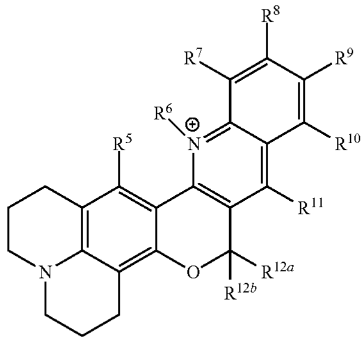

each of $R^5$, $R^7$, $R^8$, $R^{10}$, $R^{11}$, $R^{12a}$ and $R^{12b}$ is H; and $R^6$ is methyl; then $R^9$ is a substituted $C_1$-$C_6$ alkyl comprising a carboxyl;

wherein at least one of $R^2$, $R^3$, $R^6$, $R^7$, $R^8$, $R^9$, $R^{10}$ and $R^{11}$ comprises a carboxyl group.

2. The compound of claim 1, wherein $R^2$ is H and $R^3$ is $C_1$-$C_6$ alkyl or substituted $C_1$-$C_6$ alkyl, or each of $R^2$ and $R^3$ is independently $C_1$-$C_6$ alkyl.

3. The compound of claim 1, wherein the compound of Formula (I) is represented by Formula (Ia), a salt, or a mesomeric form thereof:

(Ia)

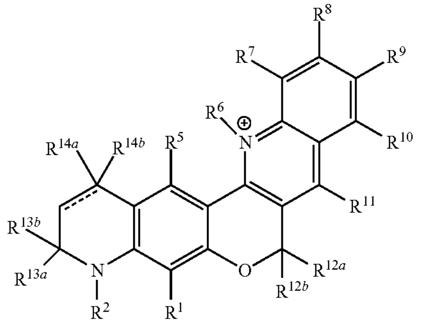

wherein each of $R^{13a}$, $R^{13b}$, $R^{14a}$ and $R^{14b}$ is independently H, $C_1$-$C_6$ alkyl, substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, ($C_1$-$C_6$ alkoxy) $C_1$-$C_6$ alkyl, optionally substituted amino, amino ($C_1$-$C_6$ alkyl), halo, cyano, hydroxy, hydroxy ($C_1$-$C_6$ alkyl), nitro, sulfonyl, sulfo, sulfino, sulfonate, S-sulfonamido, or N-sulfonamido; and the bond represented by a solid and dashed line ------ is selected from the group consisting of a single bond and a double bond, provided that when ------ is a double bond, then $R^{14b}$ is absent.

4. The compound of claim 3, wherein the bond represented by a solid and dashed line ------ is a double bond, and wherein $R^{14a}$ is H or $C_1$-$C_6$ alkyl.

5. The compound of claim 3, wherein the bond represented by a solid and dashed line ------ is a single bond.

6. The compound of claim 5, wherein $R^{14a}$ is H and $R^{14b}$ is $C_1$-$C_6$ alkyl, or each of $R^{14a}$ and $R^{14b}$ is H.

7. The compound of claim 3, wherein each of $R^{13a}$ and $R^{13b}$ is H or $C_1$-$C_6$ alkyl.

8. The compound of claim 3, wherein $R^2$ is $C_1$-$C_6$ alkyl or substituted $C_1$-$C_6$ alkyl.

9. The compound of claim 8, wherein $R^2$ is $C_1$-$C_6$ alkyl substituted with one or more substituents selected from the group consisting of carboxyl (—C(O)OH), carboxylate (—C(O)O$^-$), sulfo (—$SO_3H$), sulfonate (—$SO_3^-$), —C(O)OR$^{15}$, and —C(O)NR$^{16}$R$^{17}$, wherein $R^{15}$ is optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl, and wherein each of $R^{16}$ and $R^{17}$ is independently H, optionally substituted $C_1$-$C_6$ alkyl, optionally substituted $C_6$-$C_{10}$ aryl, optionally substituted 5 to 10 membered heteroaryl, or optionally substituted $C_3$-C7cycloalkyl.

10. The compound of claim 9, wherein $R^2$ is $C_1$-$C_6$ alkyl substituted with carboxyl or —C(O)NR$^{16}$R$^{17}$, and wherein each $R^{16}$ and $R^{17}$ is independently $C_1$-$C_6$ alkyl substituted with carboxyl, carboxylate, —C(O)OR$^{15}$, sulfo or sulfonate.

11. The compound of claim 1, wherein $R^1$ is H.

12. The compound of claim 1, wherein $R^1$ and $R^2$ are joined together with the atoms to which they are attached to form an optionally substituted 6 membered heterocyclyl.

13. The compound of claim 1, wherein each $R^5$ and $R^{11}$ is H.

14. The compound of claim 1, wherein Re is $C_1$-$C_6$ alkyl, or $C_1$-$C_6$ alkyl substituted with carboxyl or —C(O)NR16$R^{17}$, and wherein each $R^{16}$ and $R^{17}$ is independently $C_1$-$C_6$ alkyl substituted with carboxyl, carboxylate, —C(O)$OR^{15}$, sulfo or sulfonate, $R^{15}$ is optionally substituted $C_1$-$C_6$ alkyl, optionally substituted C6-C10 aryl, optionally substituted 5 to 10 membered heteroaryl, or optionally substituted $C_3$-$C_7$ cycloalkyl.

15. The compound of claim 1, wherein at least one of $R^7$, $R^8$, $R^9$ and $R^{10}$ is independently $C_1$-$C_6$ alkyl, $C_1$-$C_6$ alkoxy, or $C_1$-$C_6$ alkyl substituted carboxyl, carboxylate, sulfo, sulfonate, —C(O)$OR^{15}$ or —C(O)NR16$R^{17}$, and wherein each $R^{16}$ and $R^{17}$ is independently H $C_1$-$C_6$ alkyl substituted with or carboxyl, carboxylate, —C(O)$OR^{15}$, sulfo or sulfonate, $R^{15}$ is optionally substituted $C_1$-$C_6$ alkyl, optionally substituted $C_6$-$C_{10}$ aryl, optionally substituted 5 to 10 membered heteroaryl, or optionally substituted $C_3$-$C_7$ cycloalkyl.

16. The compound of claim 1, wherein $R^8$ and $R^9$ together with the atoms to which they are attached form an optionally substituted 5 or 6 membered heterocyclyl.

17. The compound of claim 16, wherein the optionally substituted 5 or 6 membered heterocyclyl is,

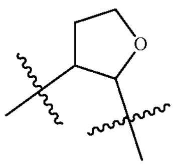
,
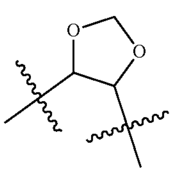
,
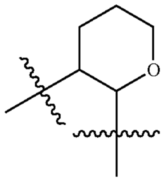
or
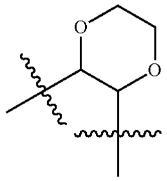
.

18. The compound of claim 1, wherein each of $R^{12a}$ and $R^{12b}$ is H.

19. The compound of claim 1, selected from the group consisting of:

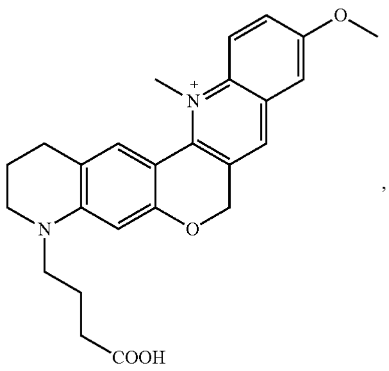
,

-continued

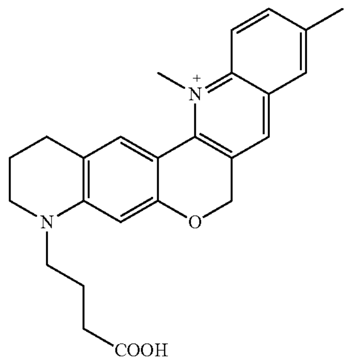
,

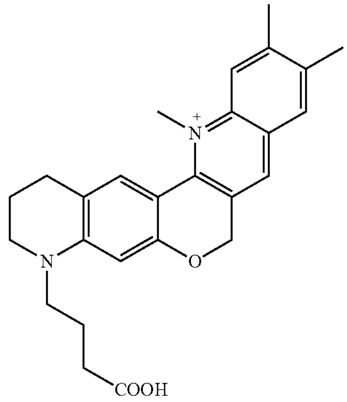
,

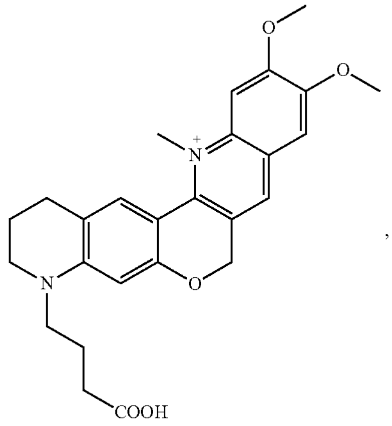
,

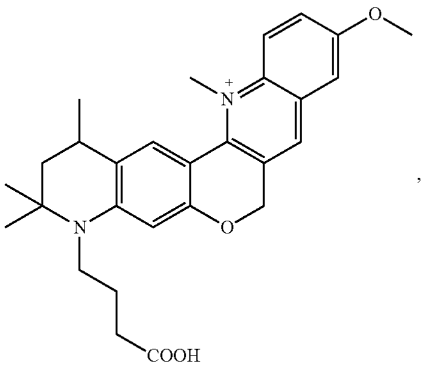
,

-continued

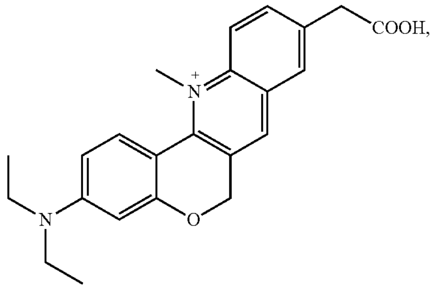

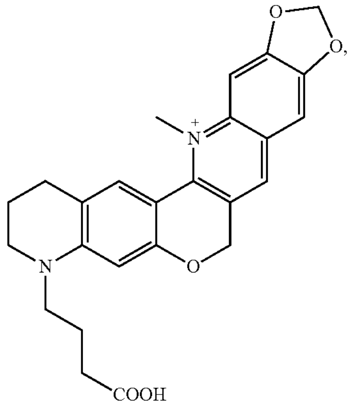

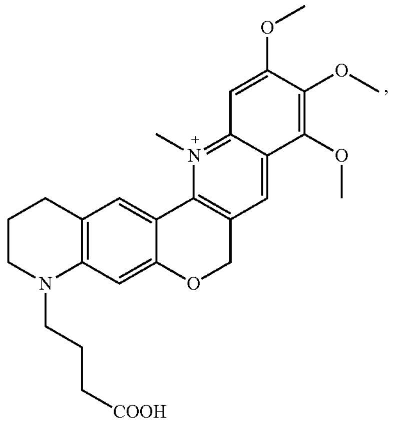

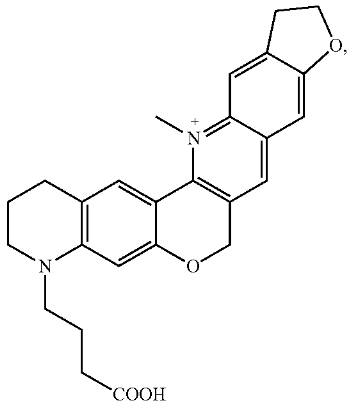

and

-continued

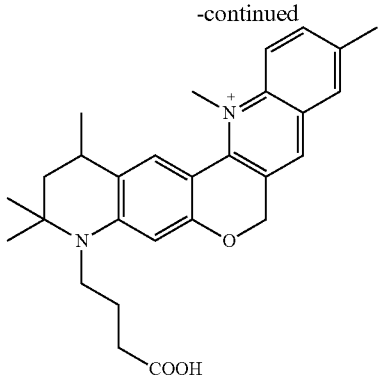

salts and mesomeric forms thereof.

20. A nucleotide or oligonucleotide labeled with a compound according to claim 1.

21. The labeled nucleotide or oligonucleotide of claim 20, wherein the compound is attached to the nucleotide or oligonucleotide via a carboxyl group of $R^2$ or $R^6$ of Formula (I).

22. The labeled nucleotide or oligonucleotide of claim 20, wherein the compound is attached to the nucleotide or oligonucleotide via a carboxyl group of one of $R^7$, $R^8$, $R^9$ and $R^{10}$ of Formula (I).

23. The labeled nucleotide or oligonucleotide of claim 20, wherein the compound is attached to the C5 position of a pyrimidine base or the C7 position of a 7-deaza purine base through a linker moiety.

24. The labeled nucleotide or oligonucleotide of claim 20, further comprising a 3' OH blocking group covalently attached to the ribose or deoxyribose sugar of the nucleotide.

25. The nucleotide or oligonucleotide of claim 20, wherein the nucleotide or oligonucleotide is an oligonucleotide hybridized to at least a portion of a target polynucleotide, wherein the target polynucleotide is immobilized on a solid support, and wherein the solid support comprises an array of a plurality of immobilized target polynucleotides.

26. A kit comprising a first nucleotide labeled with a first compound according to claim 20.

27. The kit of claim 26, further comprising a second nucleotide, wherein the second nucleotide is labeled with a second compound that is different from the first compound of the first labeled nucleotide.

28. The kit of claim 27, wherein the first labeled nucleotide and the second labeled nucleotide are excitable using a first light source wavelength.

29. The kit of claim 28, further comprising a third nucleotide, wherein the third nucleotide is labeled with a third compound that is different from the first and the second compounds, and wherein the first and third labeled nucleotides are excitable using the first light source wavelength.

30. The kit of claim 27, further comprising a third nucleotide, wherein the third nucleotide is labeled with a third compound that is different from the first and the second compounds, and wherein the first and third labeled nucleotides are excitable using a second light source wavelength.

31. The kit of claim 30, further comprising a fourth nucleotide, and wherein the fourth nucleotide is unlabeled (dark).

32. The kit of claim 30, each of the first labeled nucleotide, the second labeled nucleotide and the third labeled nucleotide has an emission spectrum that is detectable in a single detection channel.

33. The kit of claim 26, further comprising a DNA polymerase and one or more buffer compositions.

34. A method of determining the sequence of a target polynucleotide, comprising:

(a) contacting a primer polynucleotide/target polynucleotide complex with one or more different types of labeled nucleotides, wherein at least one type of said nucleotide is a labeled nucleotide of claim 20, each of the one or more different types of labeled nucleotides has a 3' blocking group, and wherein the primer polynucleotide is complementary to at least a portion of the target polynucleotide;

(b) incorporating one type of labeled nucleotide into the primer polynucleotide to produce an extended primer polynucleotide; and (c) performing one or more fluorescent measurements of the extended primer polynucleotide to determine the identity of the incorporated nucleotide.

35. The method of claim 34, wherein the primer polynucleotide/target polynucleotide complex is formed by contacting the target polynucleotide with a primer polynucleotide complementary to at least a portion of the target polynucleotide.

36. The method of claim 34, further comprising (d) removing the label and the 3' blocking group from the nucleotide incorporated into the primer polynucleotide.

37. The method of claim 35, further comprising (e) washing the removed label and the 3' blocking group away from the primer polynucleotide.

38. The method of claim 37, further comprising repeating steps (a) to (e) until a sequence of at least a portion of the template polynucleotide strand is determined.

39. The method of claim 38, wherein the steps (a) to (e) is repeated at least 50 times.

40. The method of claim 34, wherein the label and the 3' blocking group from the nucleotide incorporated into the primer polynucleotide are removed in a single chemical reaction.

41. The method of claim 34, wherein the method is performed on an automated sequencing instrument, and wherein the automated sequencing instrument comprises two light sources operating at different wavelengths, or the automated sequencing instrument comprises a single light source.

42. The method of claim 39, wherein the method is carried out in an array format, wherein a plurality of target polynucleotides are immobilized on a solid support.

* * * * *